(12) United States Patent
Li et al.

(10) Patent No.: US 9,359,298 B2
(45) Date of Patent: Jun. 7, 2016

(54) CAJANINE STRUCTURE ANALOGOUS COMPOUND, PREPARATION METHOD AND USE

(71) Applicant: INSTITUTE OF MEDICINAL BIOTECHNOLOGY, CHINESE ACADEMY OF MEDICAL SCIENCES, Beijing (CN)

(72) Inventors: Zhuorong Li, Beijing (CN); Xingyue Ji, Beijing (CN); Situ Xue, Beijing (CN); Guanghui Zheng, Beijing (CN); Yuhuan Li, Beijing (CN); Peizhen Tao, Beijing (CN); Jiandong Jiang, Beijing (CN)

(73) Assignee: INSTITUTE OF MEDICINAL BIOTECHNOLOGY, CHINESE ACADEMY OF MEDICAL SCIENCES, Beijing (CN)

( * ) Notice: Subject to any disclaimer, the term of this patent is extended or adjusted under 35 U.S.C. 154(b) by 86 days.

(21) Appl. No.: 14/368,066

(22) PCT Filed: Dec. 18, 2012

(86) PCT No.: PCT/CN2012/001711
§ 371 (c)(1),
(2) Date: Jun. 23, 2014

(87) PCT Pub. No.: WO2013/091282
PCT Pub. Date: Jun. 27, 2013

(65) Prior Publication Data
US 2014/0371232 A1    Dec. 18, 2014

(30) Foreign Application Priority Data
Dec. 23, 2011    (CN) .......................... 2011 1 0439374

(51) Int. Cl.
*C07D 213/30*      (2006.01)
*C07D 213/68*      (2006.01)
(Continued)

(52) U.S. Cl.
CPC ............ *C07D 213/30* (2013.01); *C07D 213/55* (2013.01); *C07D 213/64* (2013.01);
(Continued)

(58) Field of Classification Search
CPC .. C07D 213/30; C07D 213/68; C07D 213/55; C07D 213/64; C07D 213/65; C07D 213/69
See application file for complete search history.

(56) References Cited

U.S. PATENT DOCUMENTS 4,745,120 A * 5/1988 Wess .................... C07D 213/30
514/277
2002/0058707 A1    5/2002 Hopp et al.

FOREIGN PATENT DOCUMENTS

| CN | 101204418 | 6/2008 |
|---|---|---|
| CN | 101485649 | 7/2009 |
| CN | 101569654 | 11/2009 |

OTHER PUBLICATIONS

International Search Report (ISR) PCT/CN2012/001711, Mar. 11, 2013, 6 pages.

*Primary Examiner* — Matthew Coughlin
(74) *Attorney, Agent, or Firm* — Rankin, Hill & Clark LLP

(57) ABSTRACT

Provided are cajanine structure analogous compounds, synthesis method and pharmacological effects thereof, the compounds of the present invention having the structure as represented by general formulas I, II, III, IV and V. Also provided are pharmaceutical compositions containing the compounds as active ingredient, and uses thereof; the compounds of the present invention having the pharmacological activities such as anti-virus, anti-virus-infection, nerve protection, anti-metabolic-diseases and the like. Also provided is a chemical total synthesis preparation method of the natural products cajanine, cajanine A and cajanine C. The present invention lays a foundation for the in-depth study and development of the compounds as clinical drugs in the future.

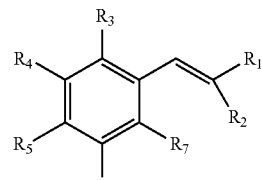

I

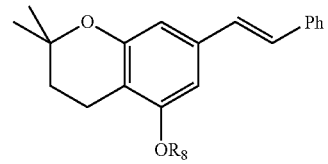

II

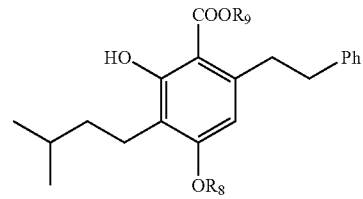

III

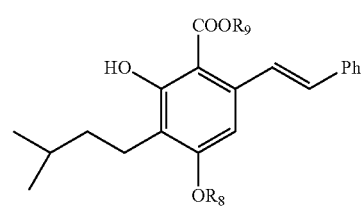

IV

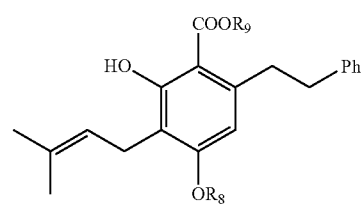

V

19 Claims, 1 Drawing Sheet

(51) Int. Cl.
  C07D 213/55 (2006.01)
  C07D 213/64 (2006.01)
  C07D 213/65 (2006.01)
  C07D 213/69 (2006.01)
  *C07C 65/28* (2006.01)
  *C07C 69/92* (2006.01)
  *C07C 51/09* (2006.01)
  *C07C 65/105* (2006.01)
  *C07C 65/19* (2006.01)
  *C07C 43/215* (2006.01)
  *C07C 43/23* (2006.01)
  *C07D 213/80* (2006.01)
  *C07D 311/58* (2006.01)
  *C07C 275/00* (2006.01)
  *C07C 275/54* (2006.01)
  *C07C 279/22* (2006.01)
  *C07C 281/02* (2006.01)
  *C07D 333/16* (2006.01)
  *C07D 333/24* (2006.01)
  *C07D 233/60* (2006.01)
  *C07D 233/90* (2006.01)
  *C07C 217/20* (2006.01)
  *C07C 217/22* (2006.01)
  *C07D 241/04* (2006.01)
  *C07C 229/08* (2006.01)
  *C07C 235/46* (2006.01)
  *C07C 235/62* (2006.01)
  *C07C 235/64* (2006.01)
  *C07D 207/16* (2006.01)
  *C07D 211/58* (2006.01)
  *C07C 69/157* (2006.01)
  *C07C 69/36* (2006.01)
  *C07C 39/21* (2006.01)
  *C07C 51/353* (2006.01)
  *C07C 51/36* (2006.01)
  *C07C 41/18* (2006.01)
  *C07C 67/30* (2006.01)
  *C07C 231/12* (2006.01)

(52) U.S. Cl.
  CPC .......... *C07D213/65* (2013.01); *C07D 213/68* (2013.01); *C07D 213/69* (2013.01); *C07C 39/21* (2013.01); *C07C 41/18* (2013.01); *C07C 43/215* (2013.01); *C07C 43/23* (2013.01); *C07C 51/09* (2013.01); *C07C 51/353* (2013.01); *C07C 51/36* (2013.01); *C07C 65/105* (2013.01); *C07C 65/19* (2013.01); *C07C 65/28* (2013.01); *C07C 67/30* (2013.01); *C07C 69/157* (2013.01); *C07C 69/36* (2013.01); *C07C 69/92* (2013.01); *C07C 217/20* (2013.01); *C07C 217/22* (2013.01); *C07C 229/08* (2013.01); *C07C 231/12* (2013.01); *C07C 235/46* (2013.01); *C07C 235/62* (2013.01); *C07C 235/64* (2013.01); *C07C 275/00* (2013.01); *C07C 275/54* (2013.01); *C07C 279/22* (2013.01); *C07C 281/02* (2013.01); *C07C 2101/02* (2013.01); *C07C 2101/14* (2013.01); *C07D 207/16* (2013.01); *C07D 211/58* (2013.01); *C07D 213/80* (2013.01); *C07D 233/60* (2013.01); *C07D 233/90* (2013.01); *C07D 241/04* (2013.01); *C07D 311/58* (2013.01); *C07D 333/16* (2013.01); *C07D 333/24* (2013.01)

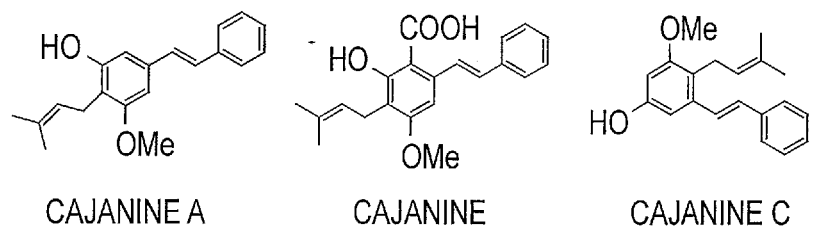

CAJANINE STRUCTURE ANALOGOUS COMPOUND, PREPARATION METHOD AND USE

CROSS REFERENCES TO RELATED APPLICATIONS

This application is a US national stage application filed under 35 USC §371 from PCT/CN2012/001711 filed Dec. 18, 2012, which claims priority upon Chinese application CN201110439374.X filed Dec. 23, 2011.

TECHNICAL FIELD

The present invention describes herein relates to cajanine structure analogous compounds, and the preparations method thereof, also relates to the application of the compounds for anti-viral and anti-bacterial infections, neuroprotection as well as anti-metabolic diseases (e.g., osteoporosis, hyperlipidemia, hyperglycemia), as well as the pharmaceutical compositions containing such compounds as active ingredients, and uses thereof. The present invention also relates to the total chemical synthesis method of natural products cajanine, cajanine A and C.

BACKGROUND

Pigeonpea (*Cajanus cajan* L.) is a pigeon pea plants (*Leguminosae* sp), with a wide range of medicinal value. Main function of pigeonpea seeds is the treatment of liver and kidney edema, blood strangury, hemorrhoids leading to hematockezia, etc. Pigeon pea root has the functions of detoxification, removing dampness, and hemostasis, acesodyne, as well as disinsection, mainl used for the treatment of sore throat, hemorrhoids leading to hematockezia, blood strangury and edema, dysuria and so on. Pigeon pea leaves have the function of detoxification and detumescence, mainly used for the treatment of pediatric chickenpox, ulcers and so on. Pigeon pea leaves contain large amounts of stilbene-type compounds, such as cajanine, cajanine A, cajanine C (chemical structure shown in FIG. 1), these compounds have a wide range of pharmacological effects, such as anti-osteoporosis. Stilbene-type extracts, can effectively promote bone cell formation and inhibitbone cell absorption (Refer to Pharmaceutical Journal, 2007, 42 (4): 386-391). In the treatment of hyperlipidemia, stilbene-type extract from pigeon pea leavesis demonstrated to significantly lower abnormally elevated serum levels of TC, TG and LDL-C levels (see CN101204418A, 2008.6.25.). In addition, stilbene-type extract from pigeon pea leaves also has anti-hypoxic ischemic brain damage, it has the protection effect on the stability of brain microvascular membranes and brain cell membranes under cerebral ischemic conditions (Refer to Traditional Chinese Drug Research & Clinical Pharmacology, 2006, 17 (3): 172-174).

American scholars (see David C. Hopp et al. US20020058707 A1) also studied the hypoglycemic effect of structure analogous compounds of cajanine, cajanine A, and C, etc. (FIG. 1), the results showed that these compounds had good hypoglycemic effect, yet side effects were all small. The anti-inflammatory and analgesic effects of pigeon pea crude extract has also been demonstrated experimentally (see Sun shaomei et al., Chinese herbs, 1995, 26 (3:147-148), the experimental results showed that the cajanine preparation experimental samples had significant anti-inflammatory effect stronger than salicylic acid, and the effect was in a dose-dependent manner as well. Cajanine preparation signifi- cantly reduced vascular permeability compared with the control: inhibition rate of cajanine preparations was 38.96%. Moreover, study on the effect of cajanine preparation on the pain threshold in mice showed that, compared with that of the mice prior to administration, both by drenching high- and low doses of cajanine formulations (200, 120 mg/kg), the prolongation of the threshold was shown to extend more than twice, indicating that cajanine preparation had significant analgesic effect.

Results of the research on pharmacological effects of natural products showed cajanine and stilbene extracts from pigeon pea leaves had extensive pharmacological effect on a variety of human diseases with a strong pharmacological activity (such as osteoporosis, hyperglycemia, hyperlipoidemia, inflammation, tumors). In particular, they were shown to have a function of regulating mechanism on the balance of bone metabolism similar to estrogen (to promote bone formation while inhibiting bone resorption), and their toxic side effect were low, these studies are more in-depth in China.

However, the current domestic and international chemical researches concerning pigeonpea stilbene compounds are still limited to the natural medicinal chemistry level, such as: extraction of natural products, their isolation and structural identification. The number of the resulting structures of analogous compounds with definitely known structures is very limited. Moreover, owing to the restricted source of the related drugs, in-depth study of the pharmacological effects of natural product cajanine is difficult to develop. The inventor of this patent applied No. 201010256856.7 patent in China, was the first to complete the total synthesis of cajanine and cajanine A, thereby providing the chemical means and laying foundation for further expanding the diversity of the molecular structures of this type of compounds.

SUMMARY OF THE INVENTION

The present invention expands the diversity of molecular structures of cajanine-type compounds by chemical means, synthesize and optimize the structures of natural products for the first time; This invention proposes methods of synthesizing a large number of novel compounds having a stilbene skeleton structure, and showing the results of screening the pharmacological activities of the cajanine-type derivatives synthesized. The researches revealed the structure-activity relationship of these compounds; and found that these compounds had a wide range of strong anti-viral activity (such as anti-HIV, HCV, influenza and Cox, etc.) for the first time. Meanwhile, this invention provides the results of the researches on the functions of the above mentioned compounds in neuroprotection, anti-metabolic diseases (such as osteoporosis, hyperlipidemia, hyperglycemia) etc., thereby laying the foundation for realization of optimizing natural products leading to final achievement of active medicines.

The present invention also completed the first total synthesis of cajanine C; in the meantime, on the basis of patent 201010256856.7, another new full synthetic scheme of cajanine was also proposed.

To attain the above object, the present invention adopts the following technical schemes:

The present invention provides the cajanine structure analogous compounds in general formulas I, II, III, IV, V, and pharmaceutically acceptable salt thereof,

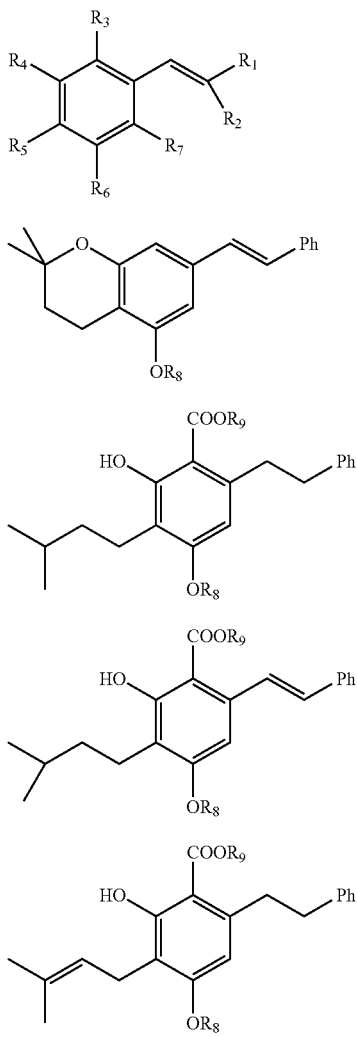

wherein R₁ represents H, a substituted or unsubstituted aryl, a substituted or unsubstituted heteroaryl, substituted or unsubstituted alkyl, a substituted or unsubstituted aryl residue, a substituted or unsubstituted alkoxycarbonyl or a carboxyl group. Preferably, R₁ is selected from substituted phenyl, benzyl, phenethyl and styryl.

R₂ represents H, a substituted or unsubstituted aryl, a substituted or unsubstituted heteroaryl, a substituted or unsubstituted alkyl, a substituted or unsubstituted aryl residue, a substituted or unsubstituted alkoxycarbonyl group or a carboxyl. Preferably, R₂ is selected from substituted phenyl, benzyl, phenethyl, styryl.

R₃ represents H, a carboxyl group, a substituted or unsubstituted alkoxyformyl, a substituted or unsubstituted carbamoyl, a substituted or unsubstituted formyl group.

R₄ represents H, hydroxy, a substituted or unsubstituted alkoxyl, a substituted or unsubstituted formyloxy group, a substituted or unsubstituted amino group or a halogen, or isoureido group.

R₅ represents H, a saturated or unsaturated alkyl, a substituted or unsubstituted aryl, an unsaturated alkyl substituted with aryl ring. Preferably, R₅ is selected from styryl, isopentenyl, isopentyl, allyl or 3',7'-dimethyloctadien-2',6'-yl.

R₆ represents H, hydroxy, a substituted or unsubstituted alkoxy, a substituted or unsubstituted amino group, a halogen, a mercapto or an alkylthio group.

R₇ represents H, isopentenyl, isopentyl, 3',7'-dimethyl octadien-2',6'-yl, a substituted or unsubstituted aryl, an allyl, a halogen, a substituted or an unsubstituted amino group.

R₈ and R₉ may be identical or different, they may represent H, an alkyl containing 1-18 carbons, respectively.

In the above definitions:

"Substituted" may be, but is not limited to substituted by halogen, alkoxy, hydroxyl, alkyl, amino group and alkylamino group. For example, a "substituted phenyl" may be, but is not limited to a phenyl substituted by halogen, alkoxy, hydroxyl, alkyl, amino and substituted amino groups in various positions of the group.

A "heteroaryl ring" may be, but is not limited to a pyridine ring, a thiophene ring, a furan ring, etc.

An "alkyl" may be, but is not limited to Straight-chain or branched-chain alkyl or cycloalkyl which contains 1 to 18 carbon atoms, e.g., methyl, ethyl, isopropyl, n-propyl, n-butyl, isobutyl, sec-butyl, tert-butyl, n-pentyl, isopentyl, n-hexyl, isohexyl, etc., or a corresponding cycloalkyl. More preferably it is selected from C1-C6 lower alkyl.

An "Alkoxyl" may be, but is not limited to an alkoxy group containing 1 to 18 carbon, such as methoxyl, ethoxyl, isopropoxyl, n-propoxyl, n-butoxyl, isobutoxyl, butoxyl, sec-butoxyl, tert-butoxyl, n-pentyloxy, isopentoxy, n-hexyloxyl, isohexyloxy. More preferably it is selected from C1-C6 lower alkoxy group.

An "Acyl group" may be, but is not limited to that with a substitution of alkyl containing 1-18 carbons or aryl, such as formyl, acetyl, isopropylcarbonyl, n-propylcarbonyl, allylcarbonyl, a cyclopropylcarbonyl, n-butylcarbonyl, is obutylcarbonyl, sec-butylcarbonyl, tert-butylcarbonyl, n-pentylcarbonyl, isopentylcarbonyl, n-hexylcarbonyl, isohexylcarbonyl, phenylcarbonyl, tolylcarbonyl and the like.

An "alkoxycarbonyl" or "ester group" may be, but is not limited to substitution of analkyl having 1-18 carbons on to an acyloxy (or unsubstituted acylox, i.e. formylox) or an aryloxy group, e.g., formyloxy, acetoxy, isopropionyloxy, n-propionyloxy, acryloyloxy, cyclopropylcarbonylox, n-butylcarbonylox, isobutylcarbonylox, sec-butylcarbonytox, tert-butylcarbonylox, n-pentylcarbonylox, isopentylcarbonylox, n-hexylcarbonylox, isohexylcarbonylox, benzoyloxy, toluoylox, etc.

"Aminoacyl" or "carbamoyl" may be acarbamoyl whose amino group is substituted by 1 or 2 alkyls having 1 to 18 carbons, or an arylcarbamoyl amino group whose amino group is substituted by the abovementioned alkyl, e.g., N-methylcarbamoyl, N-ethylcarbamoyl, N-isopropylcarbamoyl, N-n-propylcarbamoyl, N-allylcarbamoyl, N-cyclopropylcarbamoyl, N-n-butylcarbamoyl, N-sec-butylcarbamoyl, N-tert-butylcarbamoyl, N-n-pentylcarbamoyl, N-isopentylcarbamoyl, N-n-hexylcarbamoyl, N-isohexylcarbamoyl, N-phenylcarbamoyl, N-tolylcarbamoyl, etc.

"Halo" or "halogen" may be fluoro, chloro, bromo or iodo.

The present invention also provides a method for the synthesis of cajanine structure analogous compounds, as shown in the general formulas I, II, III, IV, V, as follows.

The present invention provides a method of synthesizing the compound represented by the general formula I:

When R₃ is a carboxyl group, R₄ is hydroxy, R₆ is an alkoxy, R₇ is H, and the remaining groups are as defined in general formula I, the synthesis methods are as shown in the Scheme 1 below:

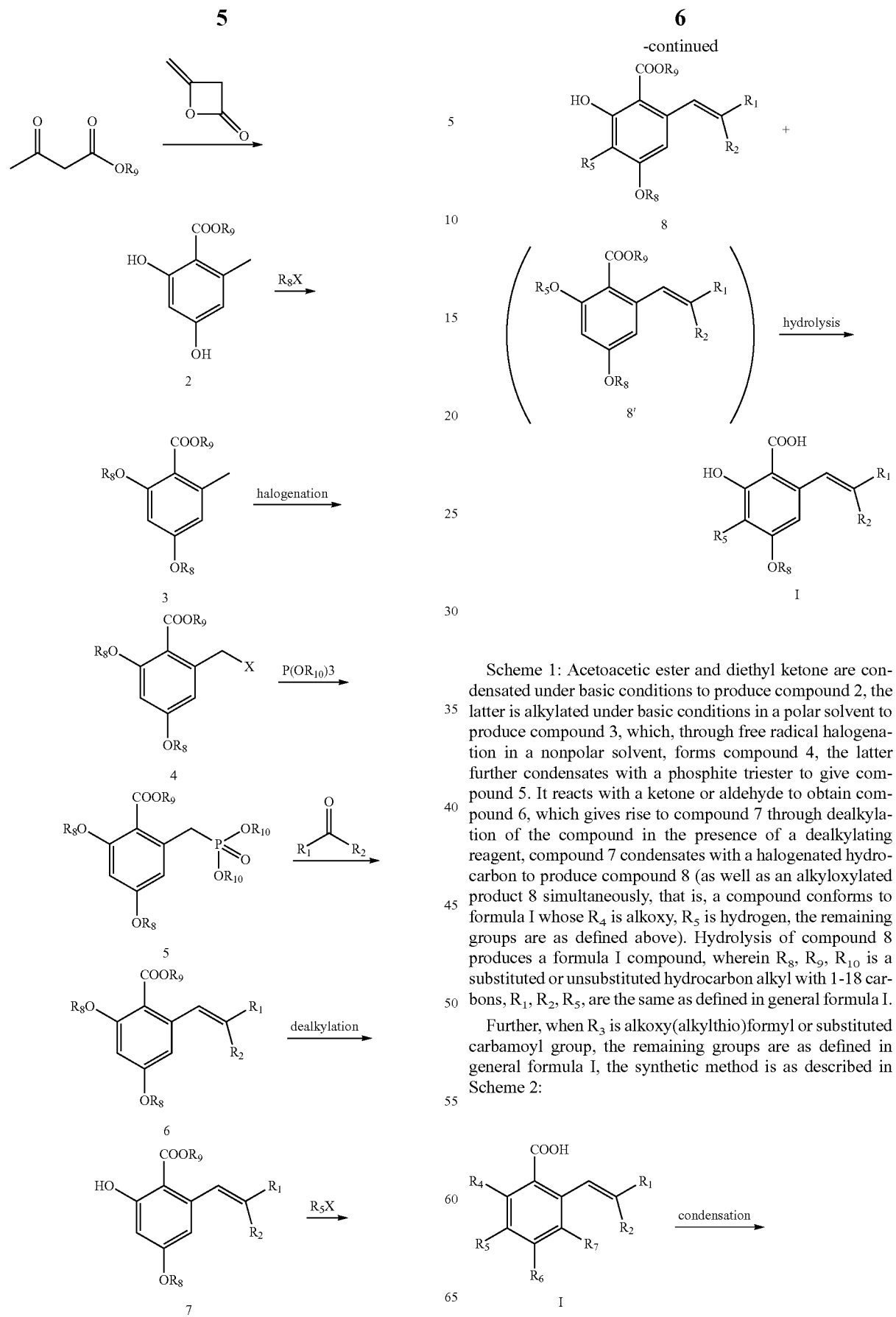

Scheme 1: Acetoacetic ester and diethyl ketone are condensated under basic conditions to produce compound 2, the latter is alkylated under basic conditions in a polar solvent to produce compound 3, which, through free radical halogenation in a nonpolar solvent, forms compound 4, the latter further condensates with a phosphite triester to give compound 5. It reacts with a ketone or aldehyde to obtain compound 6, which gives rise to compound 7 through dealkylation of the compound in the presence of a dealkylating reagent, compound 7 condensates with a halogenated hydrocarbon to produce compound 8 (as well as an alkyloxylated product 8 simultaneously, that is, a compound conforms to formula I whose $R_4$ is alkoxy, $R_5$ is hydrogen, the remaining groups are as defined above). Hydrolysis of compound 8 produces a formula I compound, wherein $R_8$, $R_9$, $R_{10}$ is a substituted or unsubstituted hydrocarbon alkyl with 1-18 carbons, $R_1$, $R_2$, $R_5$, are the same as defined in general formula I.

Further, when $R_3$ is alkoxy(alkylthio)formyl or substituted carbamoyl group, the remaining groups are as defined in general formula I, the synthetic method is as described in Scheme 2:

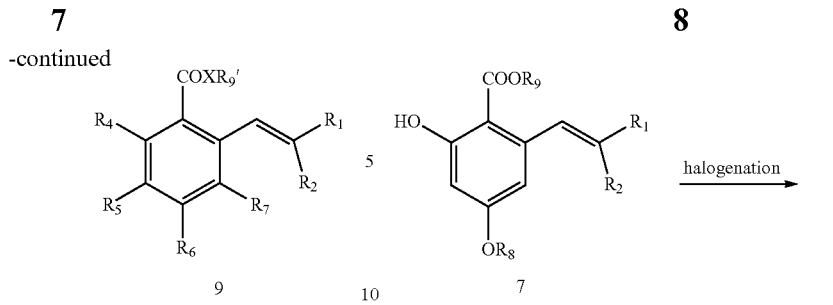

Scheme 2: In the presence of a condensation reagent, a general formula I compound condensates with one of various R$_9$XH (X=O, S, N, etc.) compounds to produce compound 9, or, a general formula I compound reacts with an acylating agent to obtain an acyl chloride, which, in the presence of an acid binding agent, condensates with various R$_9$XH to produce compound 9, wherein R$_1$, R$_2$, R$_4$, R$_5$, R$_6$, R$_7$ are the same as previously defined, R$_9$ is a substituted or unsubstituted alkyl containing 1-18 carbons, a substituted or unsubstituted aryl or heteroaryl;

wherein said condensation agent may be, but is not limited to DIC, DCC; or ether solution of various inorganic acids, such as HCl, H$_2$SO$_4$, BF$_3$, or other Lewis acids; said acylating reagent may be, but is not limited to SOCl$_2$, oxalyl chloride, etc.; said acid-binding reagent may be, but is not limited to organic bases such as DMAP, Et$_3$N, or various inorganic bases such as NaOH, KOH, Na$_2$CO$_3$, K$_2$CO$_3$.

Further, the present invention also provides a method for the preparation of cajanine A, as shown in Scheme 3:

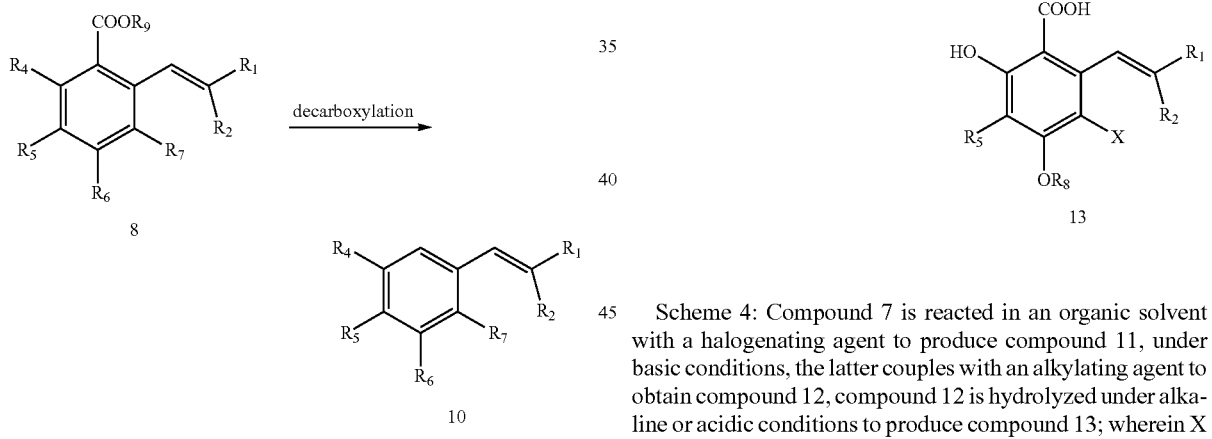

Scheme 3: The method for the synthesis of cajanine A (R$_1$=Ph, R$_2$=H, R$_4$=OH, R$_5$=isopentenyl, R$_6$=OME, R$_7$=H, compound 10 is cajanine A), under alkaline or acidic conditions and with the aid of microwave, compound 8 decarboxylates to give compound 10, wherein R$_1$, R$_2$, R$_4$, R$_5$, R$_6$, R$_7$, R$_9$ are as defined above;

said base may be, but is not limited to one of the inorganic bases, such as KOH, NaOH, K$_2$CO$_3$, Na$_2$CO$_3$ etc., said acid may be, but is not limited to one of the inorganic acids, such as HCl, H$_2$SO$_4$, H$_3$PO$_4$, the solvent may be, but is not limited to one of the polar protic solvents, such as water, various alcohols, or polar aprotic solvents such as DMSO, DMF etc.

Further, when R$_3$ is carboxyl, R$_4$ is hydroxyl, R$_6$ is an alkoxy group, R$_7$ is a halogen, and the remaining groups are as defined above, the synthesis of the corresponding compound is described in Scheme 4:

Scheme 4: Compound 7 is reacted in an organic solvent with a halogenating agent to produce compound 11, under basic conditions, the latter couples with an alkylating agent to obtain compound 12, compound 12 is hydrolyzed under alkaline or acidic conditions to produce compound 13; wherein X is F or Cl or Br; R$_1$, R$_2$, R$_5$, R$_8$, R$_9$ are as described above;

in the preparation of compound 11: said halogenating reagent may be, but is not limited to one of the following: SO$_2$Cl$_2$, NCS (N-chlorosuccinimide), NBS (N-bromosuccinimide), Br$_2$, said solvents may be, but not limited to one of the following halogenated hydrocarbon solvents: CH$_2$Cl$_2$, CHCl$_3$, CCl$_4$ etc, or one of the following polar protic solvent: MeOH, EtOH, AcOH, propanol, isopropanol, n-butanol, t-butanol, or one of the polar aprotic solvents, such as acetonitrile, DMF etc.;

in the preparation of Compound 12: said alkylating agent may be, but is not limited to one of various halogenated hydrocarbon, or a sulfonic acid ester of an alcohol, said base used may be, but is not limited to, one of the following: sodium hydride, potassium hydride, calcium hydride, sodium metal, inorganic bases such as potassium hydroxide, sodium hydroxide or an organic base such as sodium alkoxide, potassium tert-butoxide; the solvent used may be, but is not limited to an ether or an aromatic hydrocarbon solvent;

in the preparation of Compound 13: said base may be, but is not limited to an inorganic bases such as potassium carbonate, sodium hydroxide, potassium hydroxide and the like, or one of the following: amines, sodium alkoxide, potassium alkoxide and other organic bases; the acid used may be, but not limited to an inorganic acid, such as hydrochloric acid, sulfuric acid, an organic acid, such as acetic acid, etc.; the solvent used is water, an alcohol or a mixed solvent containing an active hydrogen, and the like.

Further, when $R_3$ is carboxyl, $R_4$ and $R_6$ are alkoxy, $R_7$ is H, the remaining groups are as defined above, synthesis of the compound is described in Scheme 5:

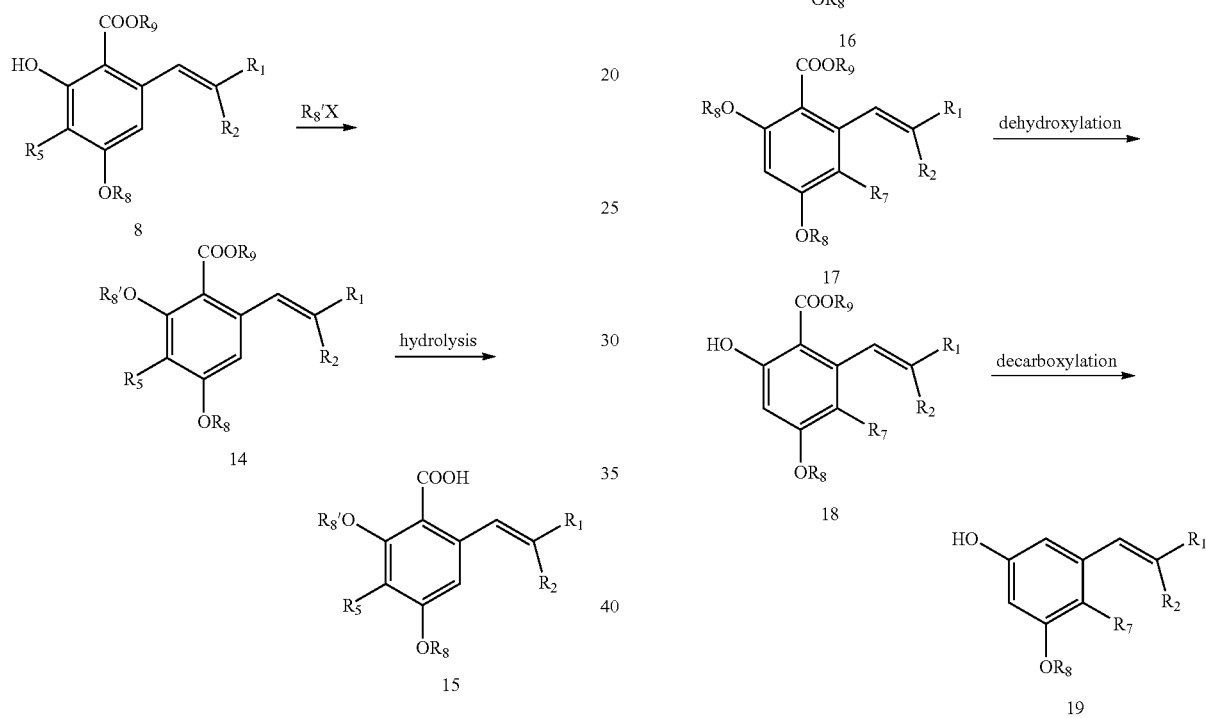

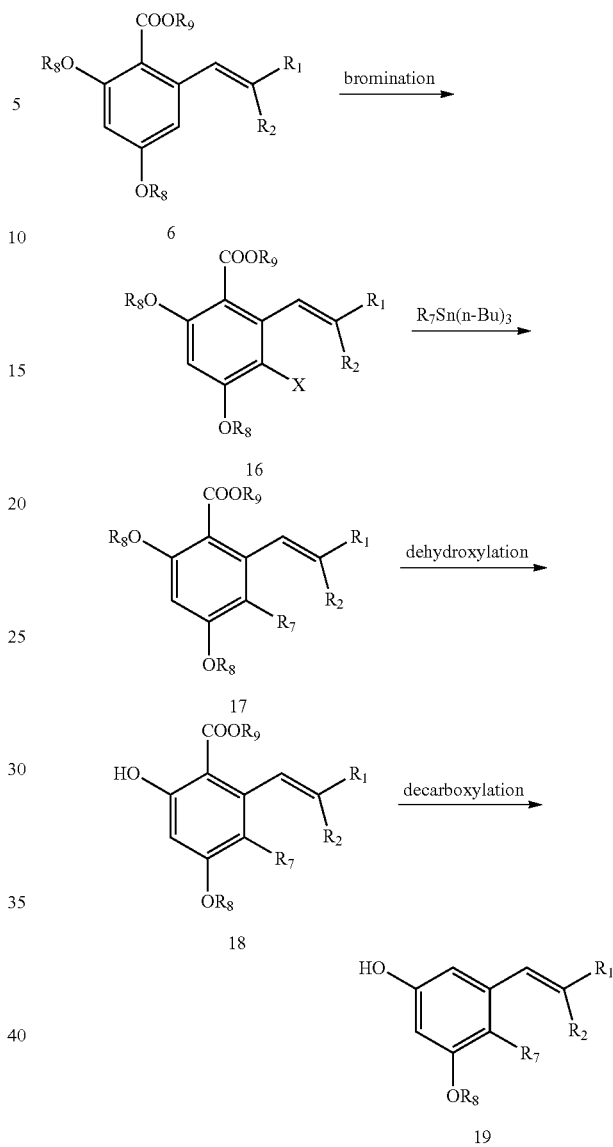

Scheme 5: Under basic conditions compound 8 reacts with an alkylating agent to obtain compound 14, subsequently, compound 14 hydrolyzed under basic or acidic conditions to produce compound 15; wherein $R_1$, $R_2$, $R_5$, $R_8$, $R_9$ are the same as defined above, $R_8$ is an alkyl group with 1-18 carbons;

in the preparation of compounds 14: said alkylating agent may be, but is not limited to one of various halogenated hydrocarbons, or sulfonate of one of various alcohols, the base used may be, but is not limited to one of the following: inorganic bases such as sodium hydride, potassium hydride, calcium hydride, sodium metal, potassium hydroxide, sodium hydroxide, potassium carbonate, sodium carbonate or an organic base such as sodium alkoxide, potassium tert-butoxide; solvent used may be, but is not limited to polar aprotic solvent or water, or a polar protic solvent of alcohol type;

the hydrolysis condition in the preparation of compound 15 is the same as stated in the method in Scheme 4.

Further, the present invention also provides a method for the total synthesis of cajanine C, as shown in Scheme 6:

Scheme 6 is the route of total synthesis of cajanine C($R_7$=isopentenyl, $R_8$=Me, $R_2$=H, $R_1$=Ph, Compound 19 is cajanine C): After halogenation of compound 6, compound 16 is obtained, in the presence of a catalyst for coupling reaction, compound 17 is prepared, it subsequently reacts with dealkylation reagent to produce compound 18, then it decarboxylates to obtain compound 19; wherein $R_1$, $R_2$, $R_7$, $R_8$, $R_9$ are consistent with the above definition;

The hydrolysis condition in the preparation of compound 16 is the same as stated in the method of Scheme 4;

in the preparation of compound 17: said coupling agent may be, but is not limited to one of the following: various trialkyl (saturated or unsaturated) tin reagent, organoboric acid, organometallic compound (RLi, RMgX, RZnX etc.); said catalyst may be but not limited to the Pd-type catalyst such as Pd(OAc)$_2$, Pd(dpPf)$_2$, Pd(PPh$_3$)$_4$, Pd$_2$(dba)$_3$, PdCl$_2$ and Pd(CH$_3$CN)$_2$; solvent used may be, but is not limited to an aprotic polar solvent such as DMF, CH$_3$CN, or an aromatic hydrocarbon solvents such as benzene, toluene, xylene, and chlorobenzene;

in the preparation of compound 18: said dealkylation reagent may be a Lewis acid reagent (e.g., boron tribromide, boron trichloride, aluminum chloride, trimethylsilyl iodide, trimethylsilyl bromide, etc.), the solvent may, but is not limited to a hydrocarbon solvent, the reaction temperature is between −80 to 25° C.;

in the preparation of compound 19, the decarboxylation method is the same as stated in Scheme 3.

Further, when $R_3$ is carboxyl, $R_4$, $R_5$=OH, the remaining groups are defined as above, the synthesis method is shown in Scheme 7:

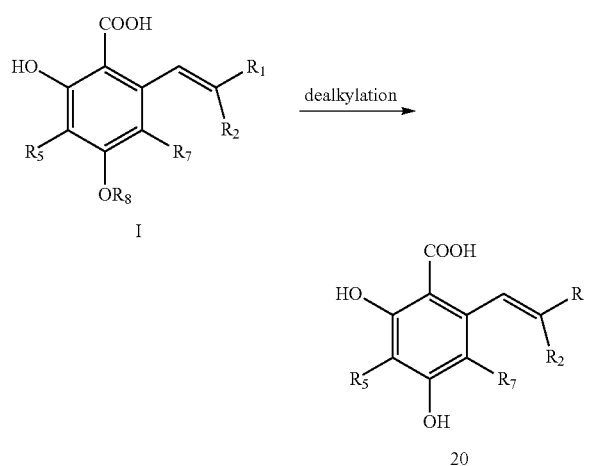

Scheme 7: One of formula I compound reacts with a dealkylation reagent to obtain the target compound 20; wherein $R_1$, $R_2$, $R_5$, $R_7$, $R_8$ are the same as defined above. Said dealkylation agents can be, but is not limited to one of protonic acids such as HI, HBr etc., or a Lewis acid such as $AlX_3$, $BX_3$, the solvent may be, but is not limited to a halogenated hydrocarbon solvent, the reaction temperature is between −80 to 25° C.

Further, when $R_3$=$R_5$=$R_7$=H, the remaining groups are defined as above, synthesis of the compound is shown in Scheme 8:

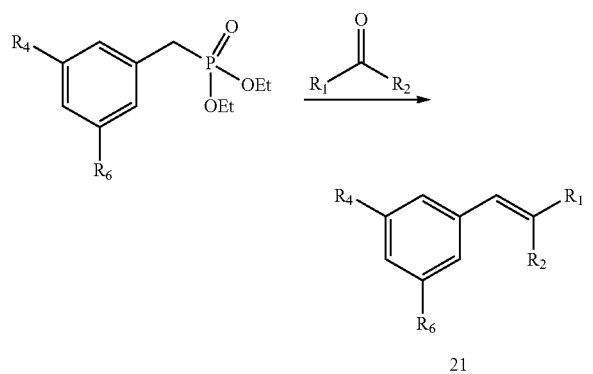

Scheme 8: the substituted benzyl phosphonate condensates with a ketone to produce the desired target product 21, wherein $R_1$, $R_2$, $R_4$, $R_6$ are the same as defined above, the reaction conditions are consistent with that in the preparation of compound 6.

Further, when $R_3$=(1H-imidazol-1-yl)formyl group, the remaining groups are as defined above, its synthetic method is described in Scheme 9:

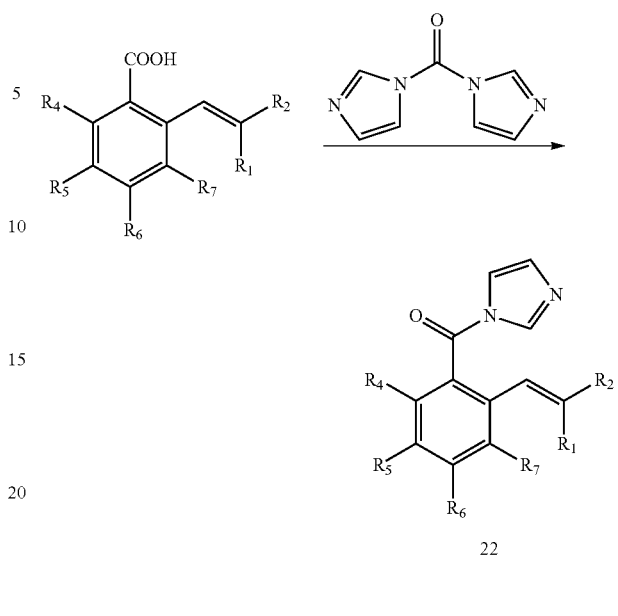

Scheme 9: in an organic solvent, 1-carboxyl derivative condensates with carbonyl diimidazole to produce the target product 22, wherein $R_1$, $R_2$, $R_4$, $R_5$, $R_6$, $R_7$ are the same as defined above, said organic solvent may be, but is not limited to one of the polar aprotic solvents, such as acetone, DMF, DMSO etc., or a halogenated hydrocarbon solvent.

Further, when $R_3$=N-(carbamoyl)carbamoyl or N-(methylamidino)carbamoyl, the remaining groups are as defined above, synthesis of the compound is described in Scheme 10:

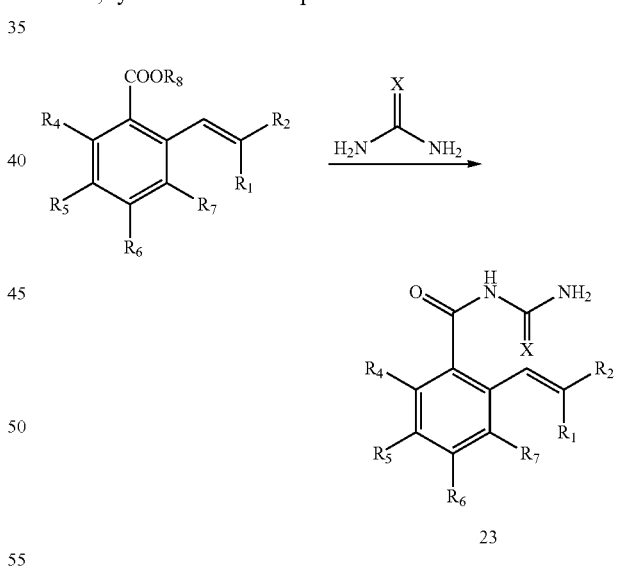

Scheme 10: in an organic solvent, a 1-alkoxycarbonyl derivative condensates with urea (X=O) or guanidine (X=NH) to produce the target product 23, wherein X=O or NH, $R_1$, $R_2$, $R_4$, $R_5$, $R_6$, $R_7$ are the same as defined above, said organic solvent may be, but is not limited to one of the alkanol solvents, such as methanol, ethanol, isopropanol.

Further, when $R_4$=substituted formyloxy, the remaining groups are defined above, synthesis of the compound is described in Scheme 11:

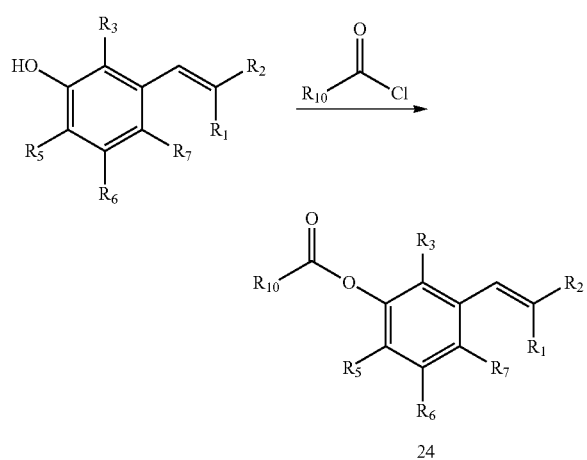

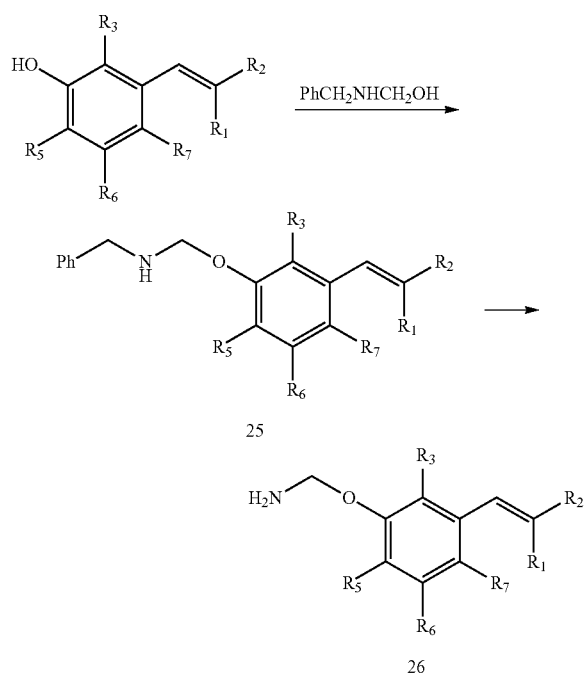

Scheme 11: under basic conditions, 2-hydroxyl derivatives condensates with an acyl chloride to produce target product 24, wherein $R_1$, $R_2$, $R_3$, $R_5$, $R_6$, $R_7$ are defined above, $R_{10}$ is a substituted or unsubstituted alkyl, a substituted or unsubstituted heteroaryl, a substituted or unsubstituted amino group, said base may be, but is not limited to, an organic base such as triethylamine, pyridine, diethylamine, or an inorganic base such as anhydrous potassium carbonate, sodium carbonate, KOH, NaOH etc.

Further, when $R_4$=aminomethoxy group, or piperazin-2-ylmethoxy group, the remaining groups are as defined above, synthesis of the compound is described in Scheme 12 (aminomethoxy group is taken as an example showing below, the description applies when $R_4$ is piperazinyl- or triazin-2-ylmethoxy):

Scheme 12: in the presence of a condensating reagent, 2-hydroxy derivative condensates with N-benzylaminoethanol to produce compound 25, then it reacts with a debenzylation reagent to obtain the target product 26, wherein $R_1$, $R_2$, $R_3$, $R_5$, $R_6$, $R_7$ are the same as defined above;

in the preparation of Compound 25, the said condensating reagent may be, but is not limited to condensating reagents such as diethyl azodicarboxylate+triphenylphosphine, diisopropyl azodicarboxylate+triphenylphosphine etc.;

in the preparation of Compound 26, said debenzylation reagent may be, but is not limited to Zn+ammonium formate, Mg+ammonium formate and the like.

Further, when $R_4$=isoureido group, the remaining groups are as defined above, the method of synthesis are described in Scheme 13:

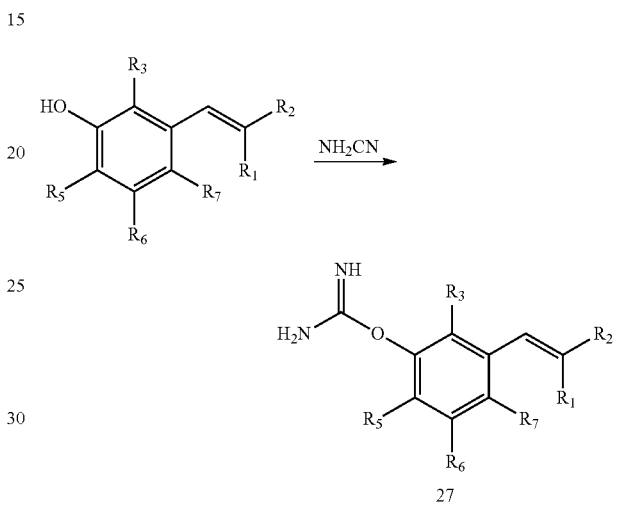

Scheme 13: under acidic conditions, a 2-hydroxyl derivative reacts with aminocyanide to produce the target compound 27, wherein $R_1$, $R_2$, $R_3$, $R_5$, $R_6$, $R_7$ are the same as defined above, said acidic conditions may be, but is not limited to, one of the inorganic acids such as hydrochloric acid, sulfuric acid, phosphoric acid, or one of the organic acids such as methanesulfonic acid or trifluoroacetic acid, etc.

Further, when $R_4$=hydrazino formyloxy, the remaining groups are as defined above, synthesis of the compound is described in Scheme 14:

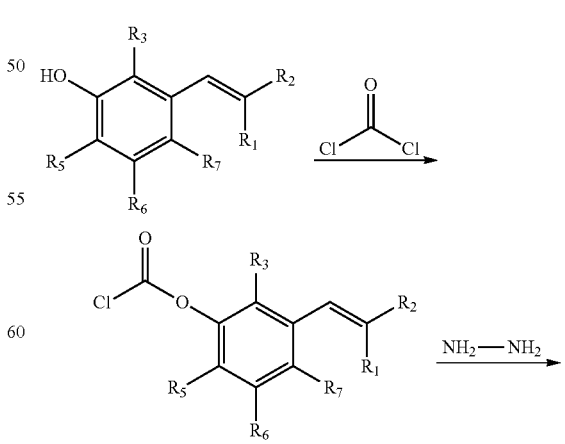

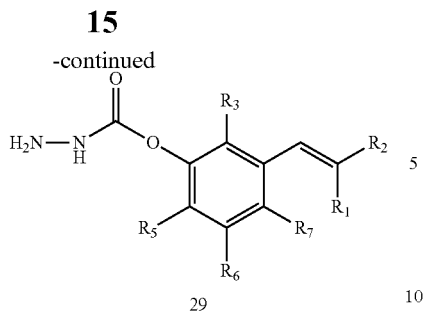

Scheme 14: under alkaline conditions, 2-hydroxyl derivative reacts with phosgene to produce compound 28, compound 28 condensates with hydrozine under basic conditions to obtain the target product 29, wherein $R_1$, $R_2$, $R_3$, $R_5$, $R_6$, $R_7$ is the same as defined above;
in the preparation of compound 28, said base may be, but is not limited to one of the organic amines, such as pyridine, triethylamine, N,N-dimethyl pyridine, or one of the inorganic bases, such as potassium carbonate, sodium carbonate, potassium hydroxide and the like;
in the preparation of compound 29, the conditions are similar to those stated in the preparation of compound 28.

Further, when the group $R_4$=carboxyl carboxyloxy, the remaining groups are as defined above, synthesis of the compound is described in Scheme 15:

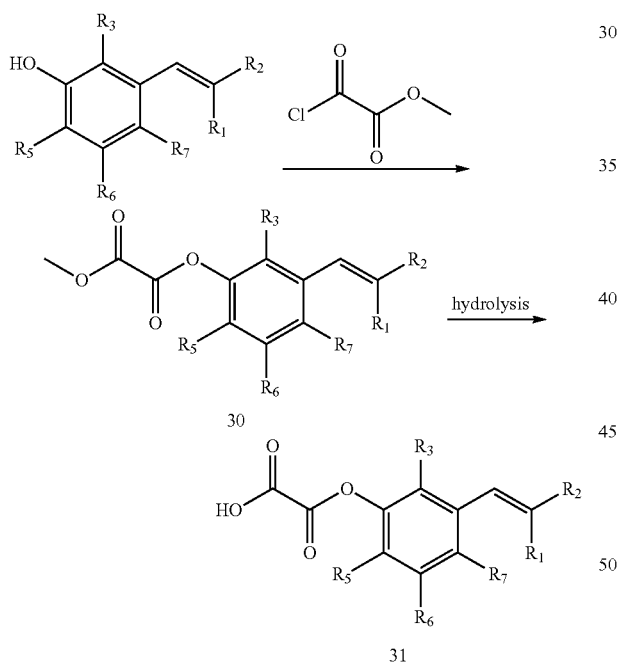

Scheme 15: under basic conditions, 2-hydroxyl derivative condensates with methyl 2-chloroglyoxylate to produce compound 30, it is further hydrolyzed to obtain the target product 31, wherein $R_1$, $R_2$, $R_3$, $R_5$, $R_6$, $R_7$ are the same as defined above;
conditions for the preparation of compound 30 is consistent with those described in the preparation of compound 28;
conditions for the preparation of compound 31 is consistent with those described in the preparation of compound 1.

Further, when $R_3$=carbamoyl, the remaining groups are as defined above, synthesis of the compound is described in Scheme 16:

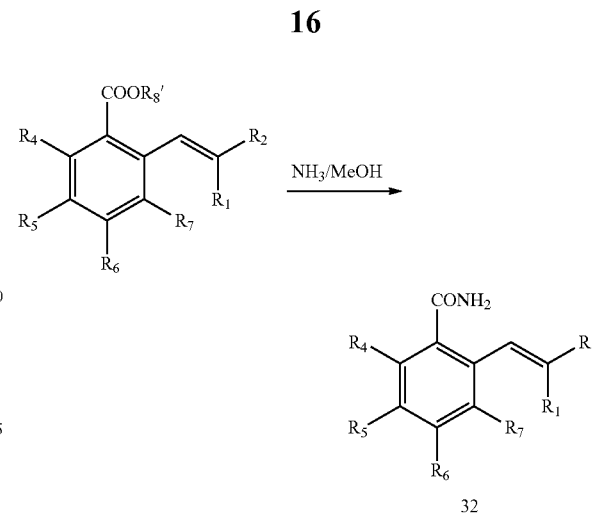

Scheme 16: in an organic solvent solution, 1-alkoxyformyl substituted benzene derivative is aminolyzed to produce the desired target product 32, wherein, $R_1$, $R_2$, $R_4$, $R_5$, $R_6$, $R_7$ are the same as defined above, $R_8$ is an alkyl group having 1-18 carbons, said organic solvent may be, but is not limited to one of the following alkanols: methanol, ethanol, isopropyl alcohol, or a halogenated hydrocarbon solvent.

Further, the present invention also provides a method to synthesize a compound having formula II structure, wherein $R_8$ is methyl, as described in Scheme 17:

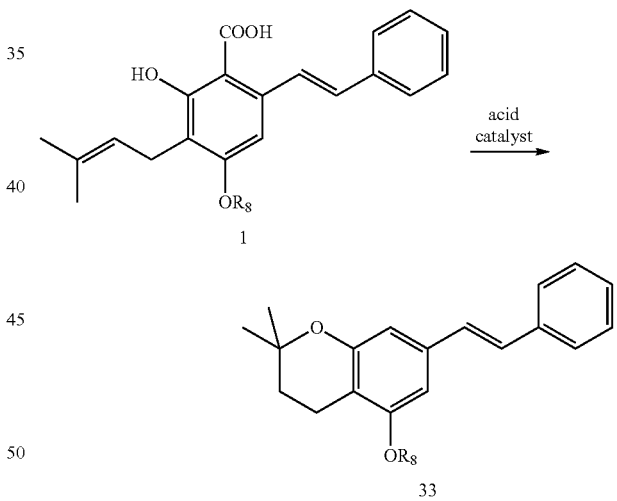

Scheme 17: In the presence of an acid catalyst, the compound decarboxylates to obtain intramolecular addition product 33;
said acid catalyst may be, but is not limited to one of the Lewis acids such as $AlCl_3$, $BCl_3$, $BBr_3$, $SiMe_3I$, the solvent may be, but is not limited to one of the halogenated hydrocarbons such as dichloromethane, chloroform, chlorobenzene; the reaction temperature is between 0 to 80° C.

Further, the present invention also provides a method to synthesize a compound having Formula III structure, wherein $R_9$ is H, $R_8$ is consistent with above definition, as described in Scheme 18.

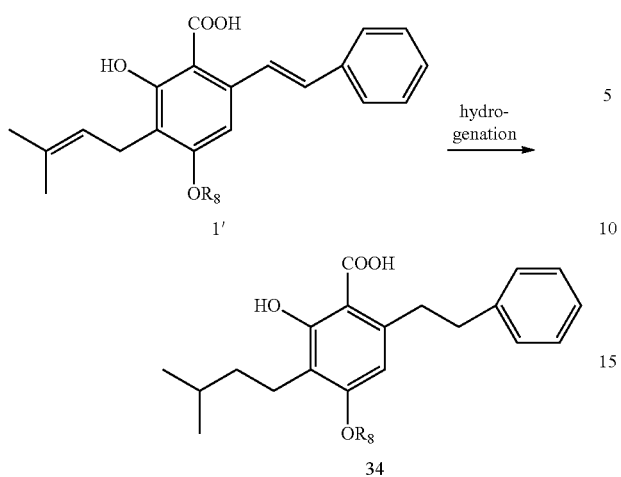

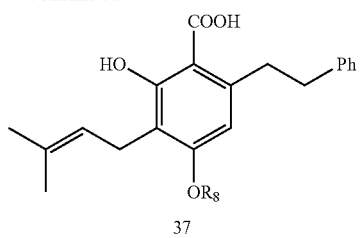

Scheme 18: under the catalytic effect of a Pd-type catalyst, cajanine analogous compound 1 is hydrogenated to obtain a product with all of the double bond reduced;

said Pd-type catalyst can be, but is not limited to Pd/C, Pd/BaSO$_4$. The reaction temperature is between 0 to 50° C., the reaction pressure is between 0 to 100 psi, the solvent may be, but not limited to one of an alkanol solvents such as methanol, ethanol, propanol or one of a acidic solvents such as acetic acid, or one of an aromatic hydrocarbon solvents such as toluene, benzene, xylene, etc.

Further, the present invention also provides a method to synthesize a compound having formula IV structure, wherein R$_8$, R$_9$ are consistent with those defined above, as described in Scheme 19:

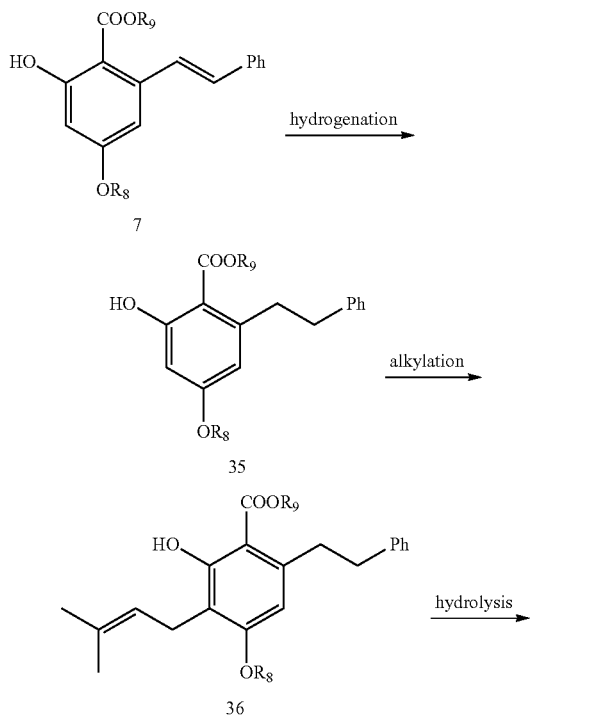

Scheme 19: through catalytic hydrogenation, compound 7 is reduced into compound 35, then it is isopentenylized to produce compound 36, and finally the latter is hydrolyzed to obtain compound 37;

the method to prepare compound 35 is consistent with that described in Scheme 18, the conditions for preparing compound 36 are consistent with those in the alkylation step in Scheme 5, the conditions for preparing compound 37 are consistent with those in hydrolysis step in Scheme 4.

Further, the present invention also provides a method of synthesizing a compound having Formula V structure, wherein R$_8$, R$_9$, R$_{10}$ are alkyl groups having 1-18 carbons, the procedure is shown in Scheme 20:

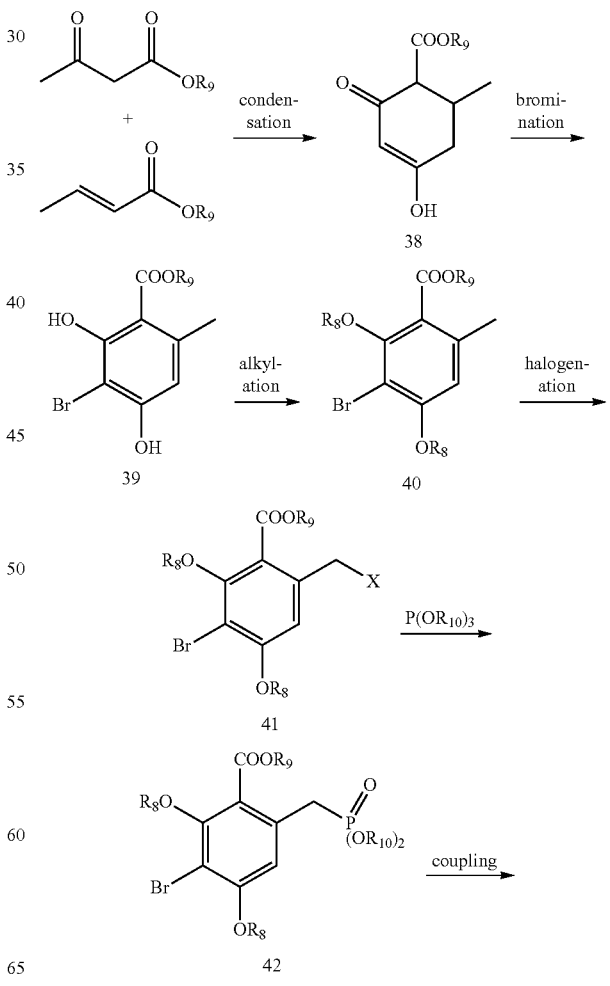

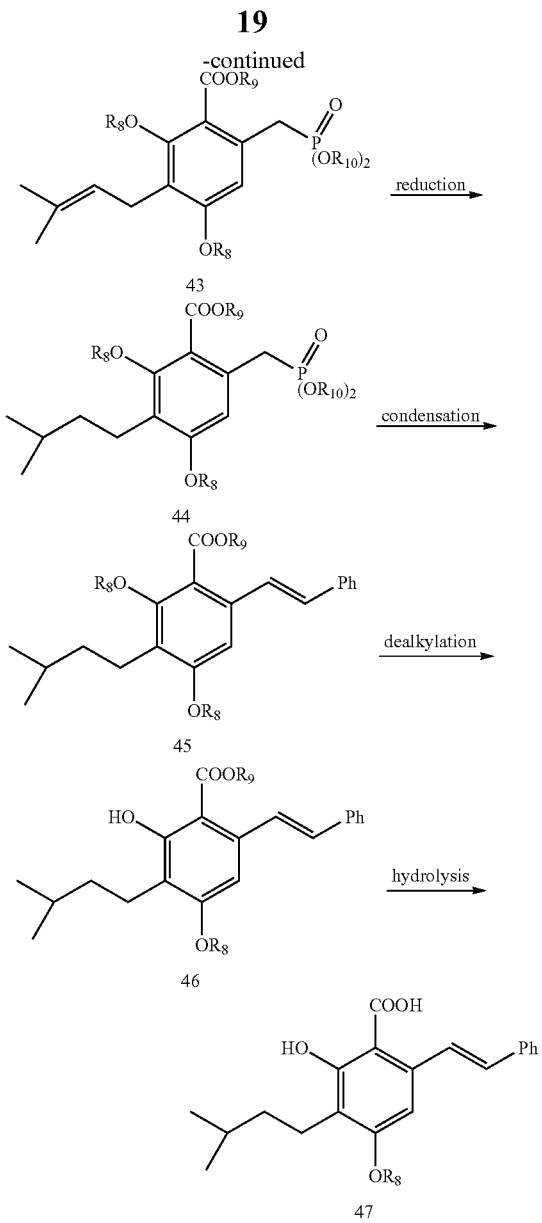

Scheme 20: Under basic conditions, acetoacetate ester and crotonic condensate to obtain compound 38, it subsequently arylizes after bromination to produce compound 39, the latter is then alkylated to obtain Compound 40, then by free radical halogenation with a halogenating reagent to result in compound 41, which condensates with an organic phosphonae reagent to obtain compound 42, and from the latter, the alkylated product compound 43 is obtained by coupling reaction, then compound 43 is hydrogenated to obtain compounds 44, and it further condensates with benzaldehyde under basic conditions to give compound 45, after dealkylation (obtaining compound 46) and hydrolysis, compound 47 is finally obtained;

in the preparation of Compound 38, said alkaline condition can be, but is not limited to, one of the organic bases such as sodium methoxide, sodium ethoxide, sodium tert-butoxide, potassium tert-butoxide, or one of the inorganic bases such as KOH, NaOH, and $K_2CO_3$; solvent used may be, but not limited to, one of alkanols such as methanol, ethanol and the like, also may be one of the polar aprotic solvents, such as DMF, $CH_3CN$ and the like;

in the preparation of Compound 39: bromination agents may be, but is not limited to liquid bromine, NBS, etc. The solvent used may be, but is not limited to one of the aprotic polar solvents such as ethanol, acetic acid, methanol and the like, the reaction temperature is between 0 to 100° C.;

in the preparation of Compound 40, the conditions are consistent with those used in the alkylation step in Scheme 5;

in the preparation of Compound 41, The halogenating agent may be, but is not limited to the mixture of N-bromosuccinimide (NBS) and dibenzoyl peroxide (BPO) or liquid bromine, or a mixture of sulfuryl chloride and BPO, or a mixture of sulfuryl chloride and azobisisobutyronitrile (AIBN), a mixture of N-chlorosuccinimide (NCS) and BPO or AIBN, etc., the solvent used, may be, but is not limited to one of the non polar solvents such as petroleum ether, carbon tetrachloride, etc., or one of the aprotic polar solvents such as acetonitrile or chloroform; the reaction temperature is 0° C. to the reflux temperature of the selected solvent, preferably at the reflux temperature of the solvent;

in the preparation of compound 42: said organic reagent is trialkyl phosphite or triaryl phosphorus, etc., condensation reaction is carried out at the reflux temperature of the solvent or a lower temperature, but does not rule out doing at high temperature and pressure;

in the preparation of compound 43, the conditions are consistent with stated in the preparation of compound 17 following Scheme 6;

in the preparation of compound 44, the conditions are consistent with those described in Scheme 18;

in the preparation 45: The reaction solvent may be, but is not limited to, one of ether-type solvents, or various polar aprotic solvent, the basic catalyst may be, but is not limited to, one of the inorganic bases such as sodium hydride, or potassium carbonate, or one of the organic bases such as triethylamine, sodium methoxide, sodium ethoxide, potassium tert-butoxide, lithium diisopropylamide; the reaction temperature is between −10 to 100° C., preferably, the reflux temperature of the solvent;

in the preparation of Compound 46, the conditions are consistent with those stated in the preparation of compound 18 following Scheme 6;

in the preparation of Compound 47, the conditions are consistent with those stated in the hydrolysis step following Scheme 6.

Further, the present invention also provides a new synthetic Scheme for the preparation cajanine, as described in Scheme 21:

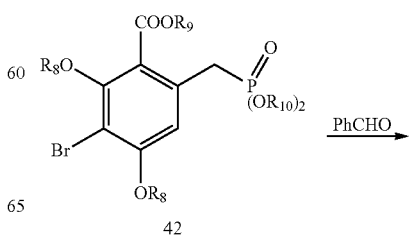

-continued

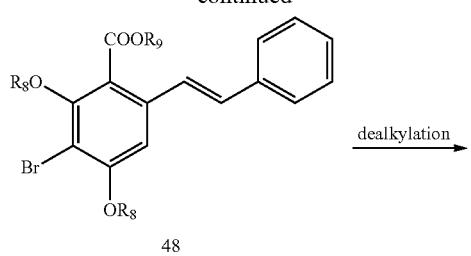

48

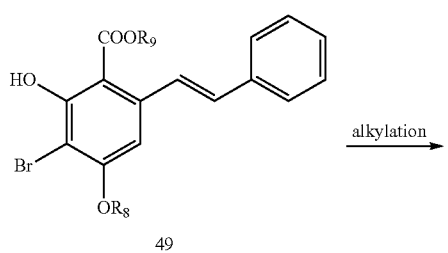

49

8

1

Scheme 21: $R_8$, $R_9$, $R_{10}$ is an alkyl group having 1-18 carbons, when $R_8$=Me, the compound is cajanine; the preparation of compound 42 is consistent with that described in Scheme 20. It condensates with benzaldehyde under alkaline condition to obtain compound 48, the latter dealkylated to obtain compound 49, after alkylation and hydrolysis, compound 1 is obtained from compound 49;

the method to prepare compound 48 is consistent with that for the preparation of compound 42 following Scheme 20, the method to prepare compound 49 is consistent with that for the preparation of compound 18 following Scheme 6, the method to prepare compound 8 is consistent with that for the preparation of compound 17 following Scheme 6, the method to prepare compound 1 is consistent with that described in the hydrolysis step following Scheme 42.

EFFECT OF THE INVENTION

According to the above described Schemes and methods, the present invention synthesized of a large number of novel cajanine analogues, completed the total chemical synthesis of cajanine C for the first time, also proposed another total new cajanine synthetic scheme. The present invention also measured for the first time the antiviral, neuroprotective, anti-metabolic diseases (such as osteoporosis, hyperlipidemia, hyperglycemia) as well as other pharmacological activities of cajanine derivatives and cajanine, cajanine A, cajanine C etc, synthesized. The activities of a part of the compounds tested exceed those of the lead compound cajanine. The structures and the results of the measurements on the pharmacological activities of the compounds proposed in this invention are shown in Table 1, Table 2, respectively.

From the result of anti-viral activity screening using cell culture method to the compounds proposed in the invention, it is found that these compounds showed a strong effect against respiratory viruses (Table 1). Among them, it is found that the anti-influenza virus activities of compound 1f, 1h, 1k, 1l, 1q, 1t, 1u, 1w, 1a, 1d, 8e, 8f, 8h, 8o, 8x, 8a, 9d, 9e, 9f, 9h, 10, 10e, 10h, 10k, 10l, 10m, 10q, 10w, 10x, 10y, 10z, 10a, 10c, 10f, 10e, 10f, 10h, 20, 21k, 23a, 23b, 24d, 24e, 24f, 24 g, 24i, 26f, 29c, 31a, 31b, 31c, 32, 46, and 47 were significantly stronger than the lead compound cajanine, what is more, in comparison with the clinical drug Tamiflu, the antiviral activities of some of the compounds proposed in this invention corresponded, or even were stronger than Oseltamivir-phosphate.

TABLE 1

The structure and the anti-viral activity of the compounds proposed in this invention

| No. | Chemical Structure | Influenza A virus (hanfang359/95) $IC_{50}$ (μg/ml) | COX-B6 $IC_{50}$ (μg/ml) |
|---|---|---|---|
| 1 | (cajanine) | 8.90 | 0.90 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 1a | [structure: 4-F phenyl stilbene with COOH, HO, OMe, prenyl] | >0.69 | >0.69 |
| 1b | [structure: 2-Cl phenyl stilbene with COOH, HO, OMe, prenyl] | >18.51 | >1.03 |
| 1c | [structure: 4-OMe phenyl stilbene with COOH, HO, OMe, prenyl] | >2.06 | 1.60 |
| 1d | [structure: 2,6-diOMe phenyl stilbene with COOH, HO, OMe, prenyl] | >0.23 | >2.06 |
| 1e | [structure: 2-Me phenyl stilbene with COOH, HO, OMe, prenyl] | >2.47 | 3.26 |
| 1f | [structure: 3-Me phenyl stilbene with COOH, HO, OMe, prenyl] | 0.48 | 4.65 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 1g | 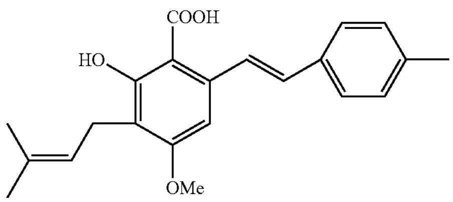 [SMILES: COc1cc(/C=C/c2ccc(C)cc2)c(C(=O)O)c(O)c1CC=C(C)C] | >0.82 | 4.25 |
| 1h | 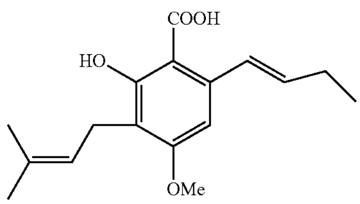 [SMILES: CC/C=C/c1cc(OC)c(CC=C(C)C)c(O)c1C(=O)O] | 1.92 | 15.30 |
| 1i | 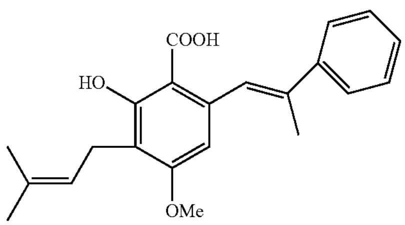 [SMILES: COc1cc(/C=C(\C)c2ccccc2)c(C(=O)O)c(O)c1CC=C(C)C] | >0.82 | 6.25 |
| 1j | 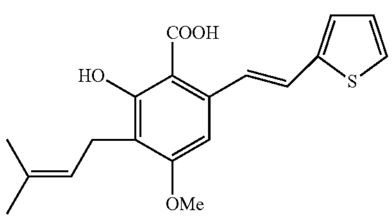 [SMILES: COc1cc(/C=C/c2cccs2)c(C(=O)O)c(O)c1CC=C(C)C] | >0.27 | 2.13 |
| 1k | 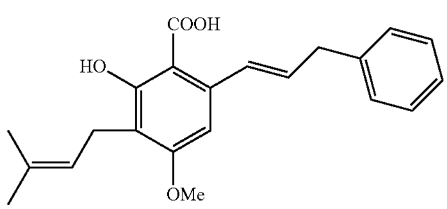 [SMILES: COc1cc(/C=C/Cc2ccccc2)c(C(=O)O)c(O)c1CC=C(C)C] | 2.05 | >2.06 |
| 1l | 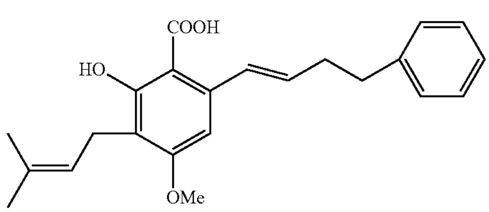 [SMILES: COc1cc(/C=C/CCc2ccccc2)c(C(=O)O)c(O)c1CC=C(C)C] | 0.36 | >2.06 |
| 1m | 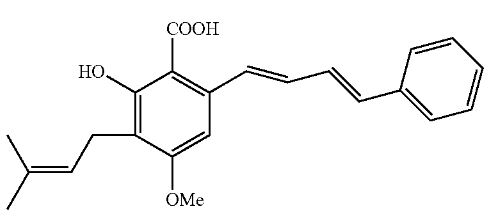 [SMILES: COc1cc(/C=C/C=C/c2ccccc2)c(C(=O)O)c(O)c1CC=C(C)C] | 6.17 | >2.06 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 1n | 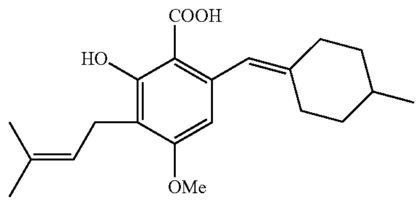 [SMILES: COc1cc(C=C2CCC(C)CC2)c(C(=O)O)c(O)c1CC=C(C)C] | >6.17 | >0.69 |
| 1o | 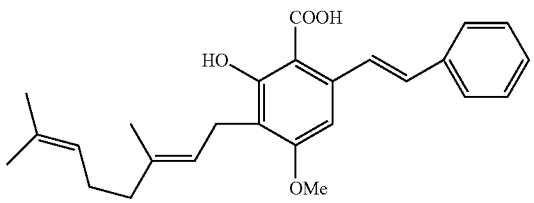 [SMILES: COc1cc(/C=C/c2ccccc2)c(C(=O)O)c(O)c1C/C=C(\C)CCC=C(C)C] | >2.47 | 1.36 |
| 1p | 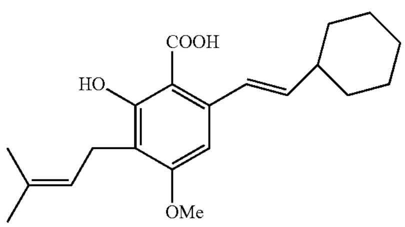 [SMILES: COc1cc(/C=C/C2CCCCC2)c(C(=O)O)c(O)c1CC=C(C)C] | 8.62 | >2.06 |
| 1q | 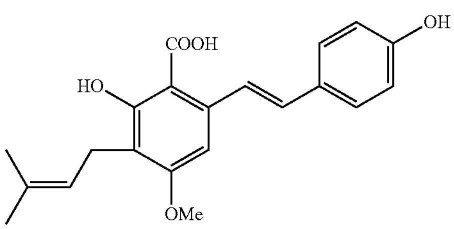 [SMILES: COc1cc(/C=C/c2ccc(O)cc2)c(C(=O)O)c(O)c1CC=C(C)C] | 2.35 | 0.86 |
| 1r | 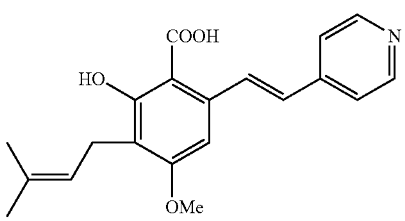 [SMILES: COc1cc(/C=C/c2ccncc2)c(C(=O)O)c(O)c1CC=C(C)C] | 6.36 | 6.35 |
| 1s | 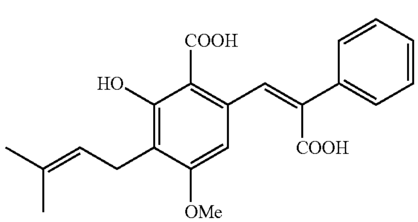 [SMILES: COc1cc(/C=C(\C(=O)O)c2ccccc2)c(C(=O)O)c(O)c1CC=C(C)C] | 0.54 | 0.85 |
| 1t | 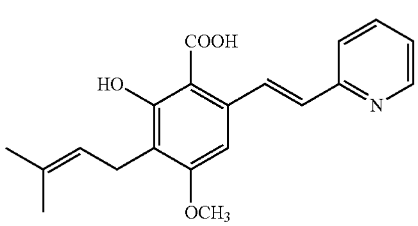 [SMILES: COc1cc(/C=C/c2ccccn2)c(C(=O)O)c(O)c1CC=C(C)C] | 0.34 | 0.61 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 1u | 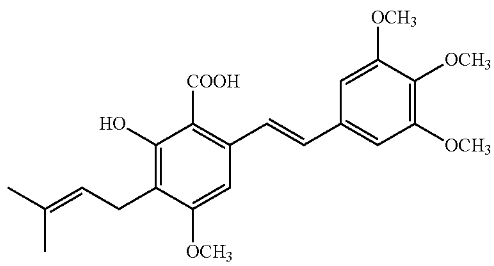 [SMILES: COc1cc(/C=C/c2cc(OC)c(OC)c(OC)c2)c(C(=O)O)c(O)c1CC=C(C)C] | 0.21 | 0.14 |
| 1v | 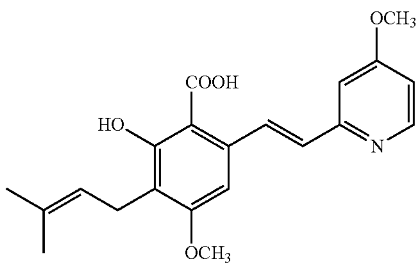 [SMILES: COc1ccnc(/C=C/c2cc(OC)c(CC=C(C)C)c(O)c2C(=O)O)c1] | 2.31 | 1.25 |
| 1w | 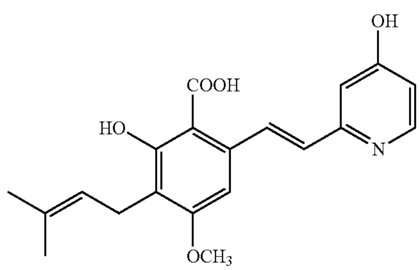 [SMILES: COc1cc(/C=C/c2cc(O)ccn2)c(C(=O)O)c(O)c1CC=C(C)C] | 0.19 | 0.54 |
| 1x | 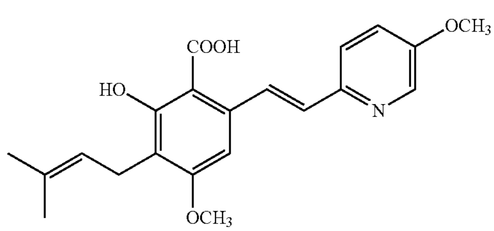 [SMILES: COc1ccc(/C=C/c2cc(OC)c(CC=C(C)C)c(O)c2C(=O)O)nc1] | 2.68 | 4.56 |
| 1y | 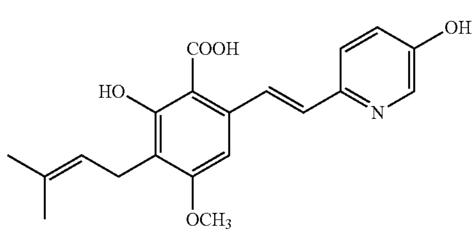 [SMILES: COc1cc(/C=C/c2ccc(O)cn2)c(C(=O)O)c(O)c1CC=C(C)C] | 4.25 | 5.84 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 1z | 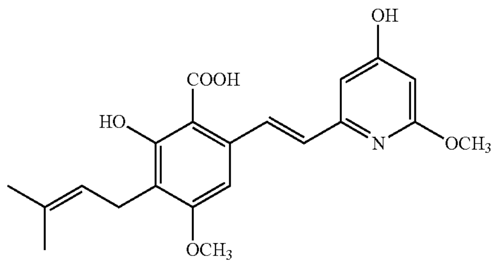 [SMILES: COc1cc(O)cc(/C=C/c2cc(OC)c(CC=C(C)C)c(O)c2C(=O)O)n1] | 1.65 | 4.89 |
| 1a' | 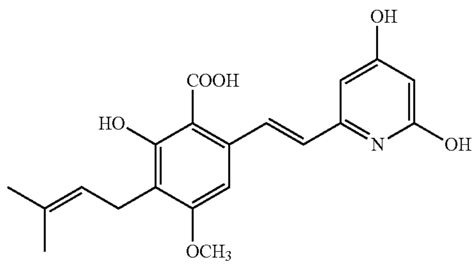 [SMILES: COc1cc(/C=C/c2cc(O)cc(O)n2)c(C(=O)O)c(O)c1CC=C(C)C] | 0.19 | 0.36 |
| 1b' | 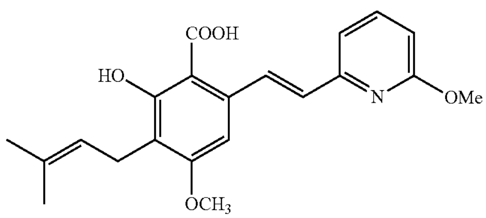 | 4.62 | 5.98 |
| 1c' | 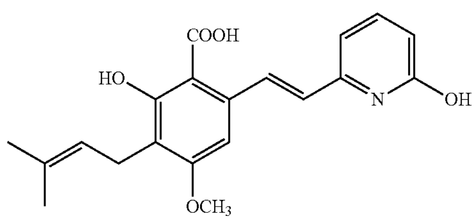 [SMILES: COc1cc(/C=C/c2cccc(O)n2)c(C(=O)O)c(O)c1CC=C(C)C] | 1.34 | 2.56 |
| 1d' | 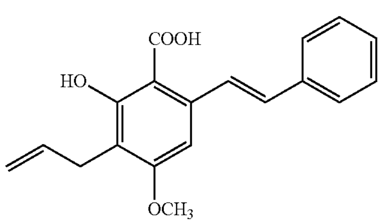 [SMILES: C=CCc1c(OC)cc(/C=C/c2ccccc2)c(C(=O)O)c1O] | 0.24 | 0.64 |
| 6 | 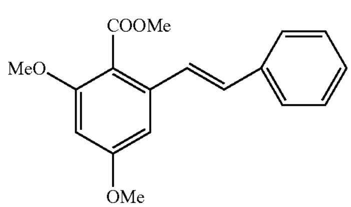 [SMILES: COC(=O)c1c(/C=C/c2ccccc2)cc(OC)cc1OC] | >2.05 | >2.06 |

TABLE 1-continued

The structure and the anti-viral activity of the compounds proposed in this invention

| No. | Chemical Structure | Influenza A virus (hanfang359/95) $IC_{50}$ (μg/ml) | COX-B6 $IC_{50}$ (μg/ml) |
|---|---|---|---|
| 7 | (structure: methyl 2-hydroxy-4-methoxy-6-styrylbenzoate) | >0.69 | >6.17 |
| 8 | (structure: methyl 2-hydroxy-4-methoxy-3-prenyl-6-styrylbenzoate) | 0.69 | 3.56 |
| 8a | (structure: 4-F styryl analog) | >0.69 | >18.52 |
| 8b | (structure: 2-Cl styryl analog) | >6.17 | >18.52 |
| 8c | (structure: 4-OMe styryl analog) | >2.06 | 4.79 |
| 8d | (structure: 2,6-diOMe styryl analog) | >6.17 | >9.26 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 8e | 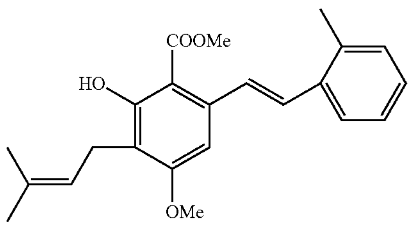 | 0.82 | 6.35 |
| 8f | 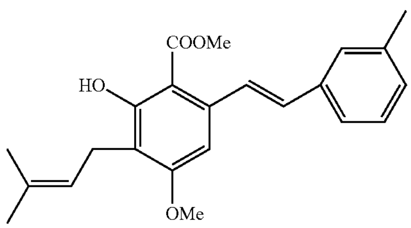 [SMILES: COC(=O)c1c(/C=C/c2cccc(C)c2)cc(OC)c(CC=C(C)C)c1O] | 0.21 | 8.26 |
| 8g | 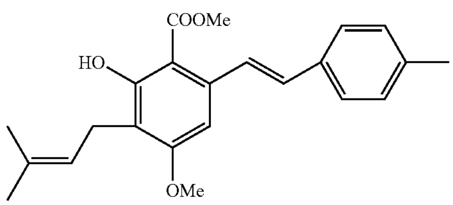 [SMILES: COC(=O)c1c(/C=C/c2ccc(C)cc2)cc(OC)c(CC=C(C)C)c1O] | >0.82 | 7.34 |
| 8h | 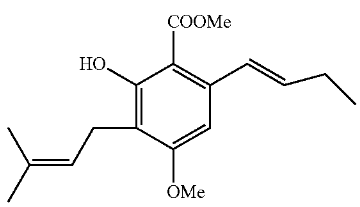 [SMILES: CC/C=C/c1cc(OC)c(CC=C(C)C)c(O)c1C(=O)OC] | 1.92 | >2.06 |
| 8i | 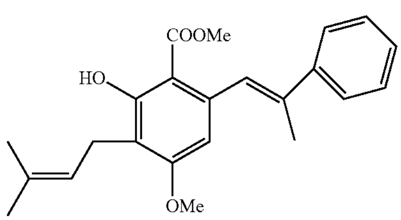 [SMILES: COC(=O)c1c(/C=C(\C)c2ccccc2)cc(OC)c(CC=C(C)C)c1O] | >2.47 | 6.89 |
| 8j | 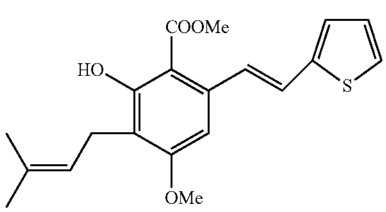 [SMILES: COC(=O)c1c(/C=C/c2cccs2)cc(OC)c(CC=C(C)C)c1O] | >0.09 | 6.68 |
| 8l | 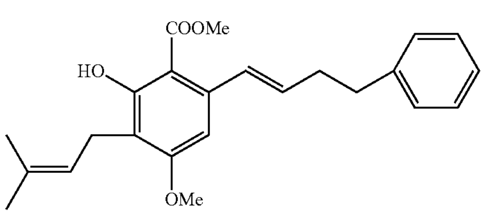 [SMILES: COC(=O)c1c(/C=C/CCc2ccccc2)cc(OC)c(CC=C(C)C)c1O] | 5.75 | >6.17 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 8m | 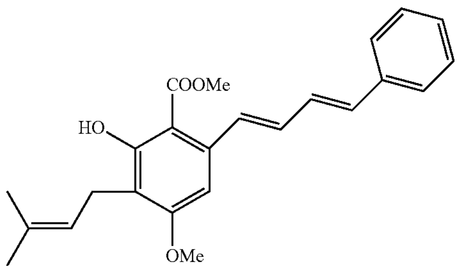 [SMILES: COC(=O)c1c(/C=C/C=C/c2ccccc2)cc(OC)c(CC=C(C)C)c1O] | 4.28 | >6.17 |
| 8n | 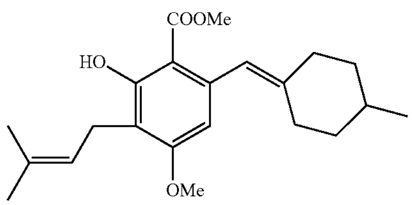 [SMILES: COC(=O)c1c(C=C2CCC(C)CC2)cc(OC)c(CC=C(C)C)c1O] | >2.06 | >6.17 |
| 8o | 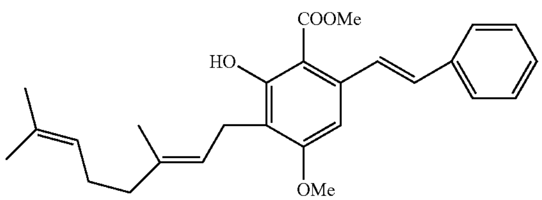 [SMILES: COC(=O)c1c(/C=C/c2ccccc2)cc(OC)c(C/C=C(\C)CCC=C(C)C)c1O] | 0.82 | 2.36 |
| 8p | 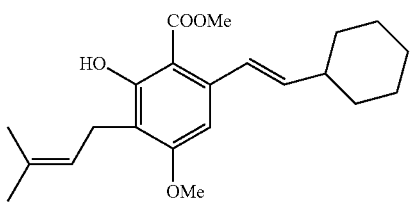 [SMILES: COC(=O)c1c(/C=C/C2CCCCC2)cc(OC)c(CC=C(C)C)c1O] | 10.35 | >2.06 |
| 8q | 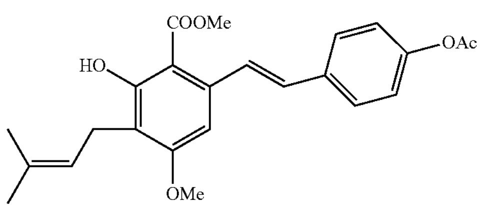 [SMILES: COC(=O)c1c(/C=C/c2ccc(OC(C)=O)cc2)cc(OC)c(CC=C(C)C)c1O] | 8.23 | 5.23 |
| 8r | 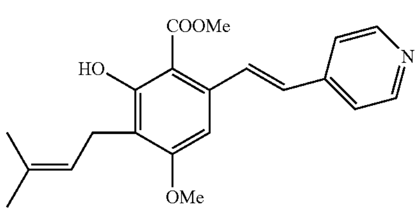 [SMILES: COC(=O)c1c(/C=C/c2ccncc2)cc(OC)c(CC=C(C)C)c1O] | 4.65 | 6.43 |
| 8s | 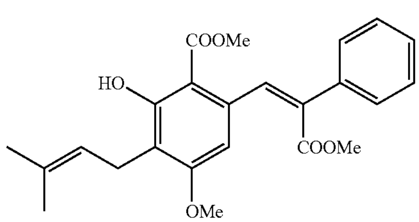 [SMILES: COC(=O)/C(=C\c1cc(OC)c(CC=C(C)C)c(O)c1C(=O)OC)c1ccccc1] | 0.24 | 3.52 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 8t | 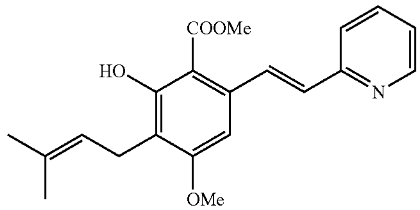 [SMILES: COC(=O)c1c(/C=C/c2ccccn2)cc(OC)c(CC=C(C)C)c1O] | 0.12 | 1.32 |
| 8u | 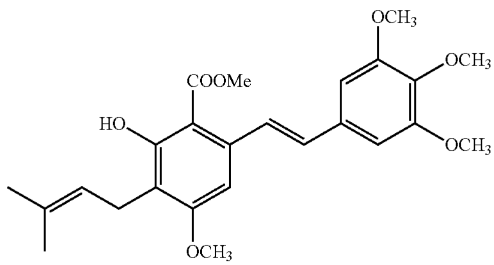 [SMILES: COC(=O)c1c(/C=C/c2cc(OC)c(OC)c(OC)c2)cc(OC)c(CC=C(C)C)c1O] | 0.11 | 1.65 |
| 8v | 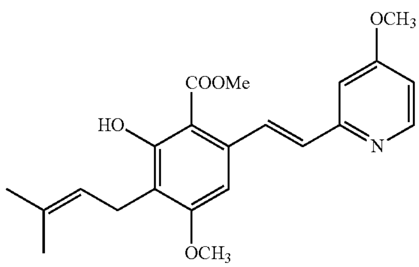 [SMILES: COC(=O)c1c(/C=C/c2cc(OC)ccn2)cc(OC)c(CC=C(C)C)c1O] | 0.87 | 2.68 |
| 8w | 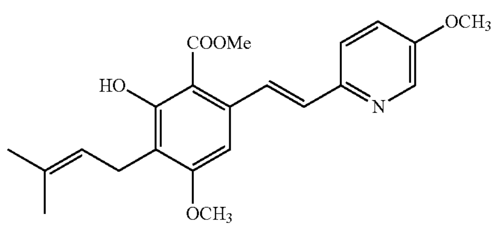 [SMILES: COC(=O)c1c(/C=C/c2ccc(OC)cn2)cc(OC)c(CC=C(C)C)c1O] | 1.32 | 5.68 |
| 8x | 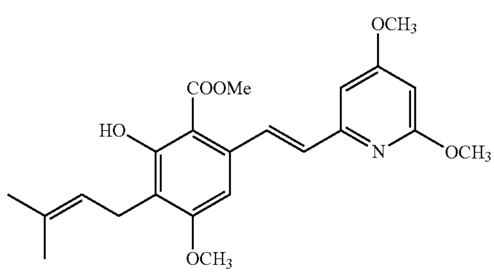 [SMILES: COC(=O)c1c(/C=C/c2cc(OC)cc(OC)n2)cc(OC)c(CC=C(C)C)c1O] | 0.65 | 4.58 |
| 8y | 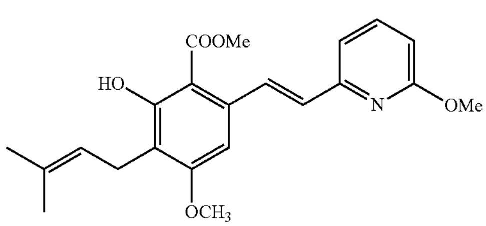 [SMILES: COC(=O)c1c(/C=C/c2cccc(OC)n2)cc(OC)c(CC=C(C)C)c1O] | 2.14 | 7.12 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 8a' | (structure with COOMe, HO, OCH$_3$, allyl, styryl) | 0.15 | 1.64 |
| 9a | (structure with COOEt, HO, OMe, prenyl, styryl) | >2.47 | 4.32 |
| 9b | (structure with COOPr, HO, OMe, prenyl, styryl) | >22.22 | 5.32 |
| 9c | (structure with COOt-Bu, HO, OMe, prenyl, styryl) | >66.67 | 5.64 |
| 9d | (structure with cyclopropyl amide, HO, OMe, prenyl, styryl) | 1.92 | 2.31 |
| 9e | (structure with glyceryl ester, HO, OCH$_3$, prenyl, styryl) | 0.10 | 0.21 |

TABLE 1-continued

The structure and the anti-viral activity of the compounds proposed in this invention

| No. | Chemical Structure | Influenza A virus (hanfang359/95) IC$_{50}$ (µg/ml) | COX-B6 IC$_{50}$ (µg/ml) |
|---|---|---|---|
| 9f | 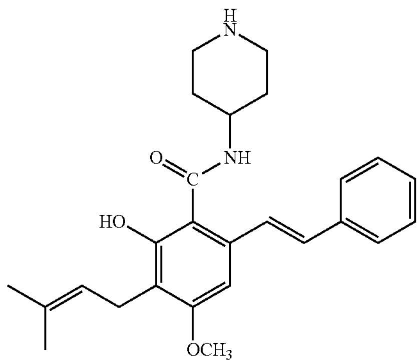 [SMILES: COc1cc(/C=C/c2ccccc2)c(C(=O)NC2CCNCC2)c(O)c1CC=C(C)C] | 0.31 | 0.24 |
| 9g | 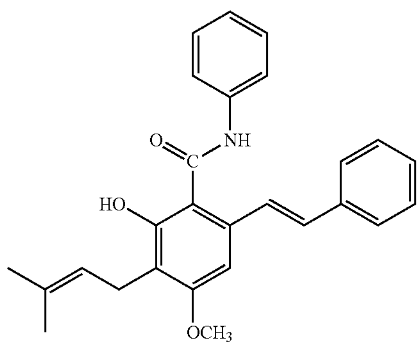 [SMILES: COc1cc(/C=C/c2ccccc2)c(C(=O)Nc2ccccc2)c(O)c1CC=C(C)C] | 0.84 | 1.59 |
| 9h | 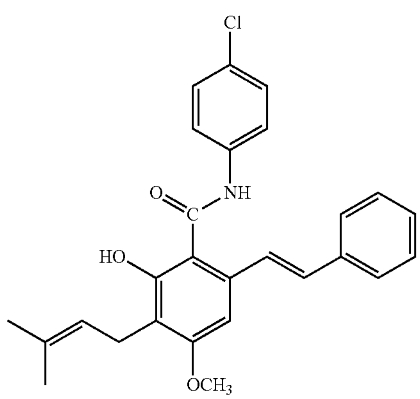 [SMILES: COc1cc(/C=C/c2ccccc2)c(C(=O)Nc2ccc(Cl)cc2)c(O)c1CC=C(C)C] | 0.47 | 2.98 |
| 10 | 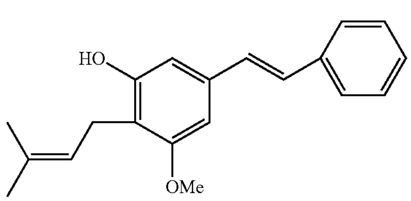 [SMILES: COc1cc(/C=C/c2ccccc2)cc(O)c1CC=C(C)C] | 0.27 | 0.69 |
| 10a | 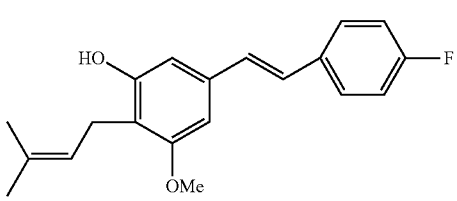 [SMILES: COc1cc(/C=C/c2ccc(F)cc2)cc(O)c1CC=C(C)C] | >0.69 | 6.32 |

TABLE 1-continued

The structure and the anti-viral activity of the compounds proposed in this invention

| No. | Chemical Structure | Influenza A virus (hanfang359/95) IC$_{50}$ (µg/ml) | COX-B6 IC$_{50}$ (µg/ml) |
|---|---|---|---|
| 10b | 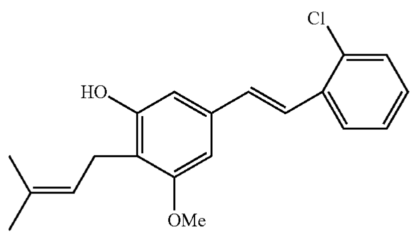 [SMILES: COc1cc(/C=C/c2ccccc2Cl)cc(O)c1CC=C(C)C] | >0.23 | 6.38 |
| 10c | 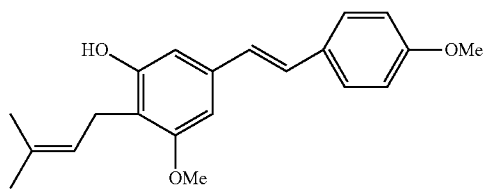 [SMILES: COc1ccc(/C=C/c2cc(O)c(CC=C(C)C)c(OC)c2)cc1] | >6.17 | 2.35 |
| 10d | 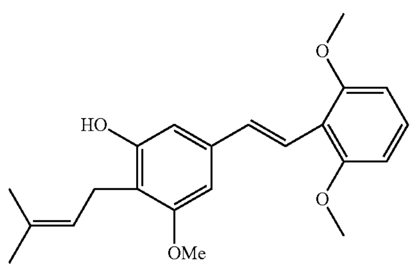 [SMILES: COc1cccc(OC)c1/C=C/c1cc(O)c(CC=C(C)C)c(OC)c1] | >6.17 | >2.05 |
| 10e | 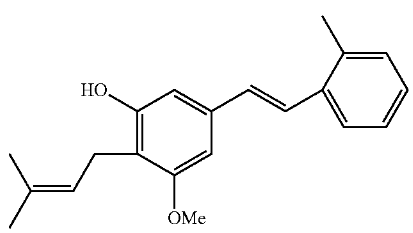 [SMILES: COc1cc(/C=C/c2ccccc2C)cc(O)c1CC=C(C)C] | 1.92 | 2.35 |
| 10f | 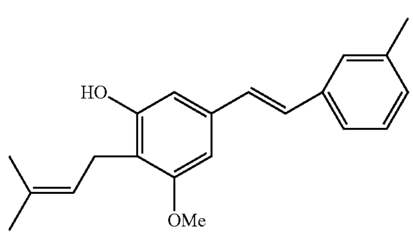 [SMILES: COc1cc(/C=C/c2cccc(C)c2)cc(O)c1CC=C(C)C] | 0.89 | 1.26 |
| 10g | 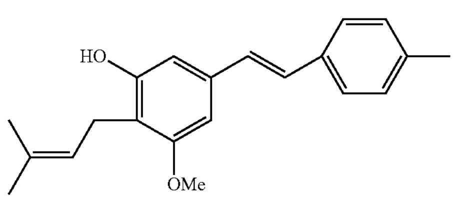 [SMILES: COc1cc(/C=C/c2ccc(C)cc2)cc(O)c1CC=C(C)C] | >6.19 | 1.18 |
| 10h | 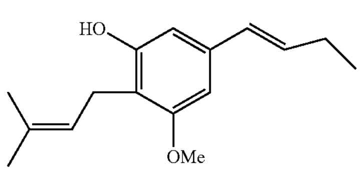 [SMILES: CC/C=C/c1cc(O)c(CC=C(C)C)c(OC)c1] | 0.74 | >2.06 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 10i | 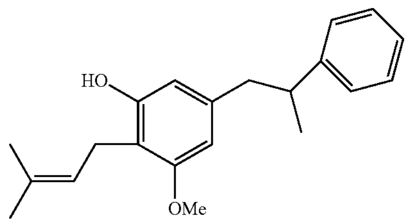 [SMILES: COc1cc(CC(C)c2ccccc2)cc(O)c1CC=C(C)C] | >0.23 | 3.26 |
| 10j | 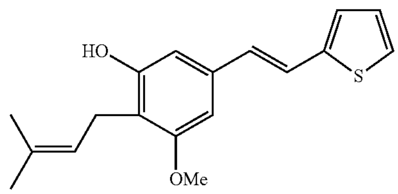 [SMILES: COc1cc(/C=C/c2cccs2)cc(O)c1CC=C(C)C] | >18.50 | 1.56 |
| 10k | 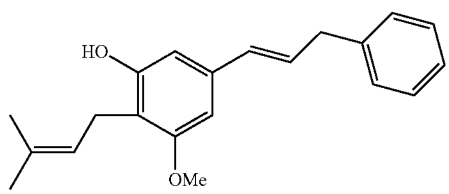 [SMILES: COc1cc(/C=C/Cc2ccccc2)cc(O)c1CC=C(C)C] | 0.89 | >2.06 |
| 10l | 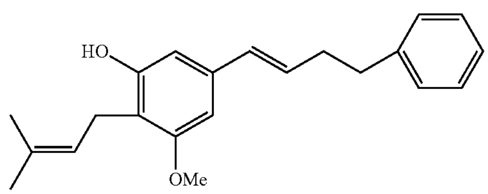 [SMILES: COc1cc(/C=C/CCc2ccccc2)cc(O)c1CC=C(C)C] | 0.65 | >18.20 |
| 10m | 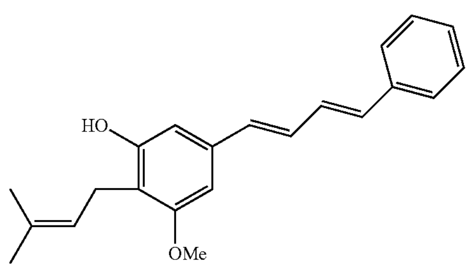 [SMILES: COc1cc(/C=C/C=C/c2ccccc2)cc(O)c1CC=C(C)C] | 2.35 | 6.12 |
| 10n | 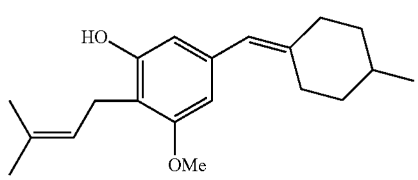 [SMILES: COc1cc(C=C2CCC(C)CC2)cc(O)c1CC=C(C)C] | >0.69 | >2.05 |
| 10o | 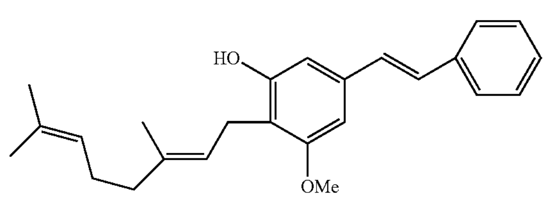 [SMILES: COc1cc(/C=C/c2ccccc2)cc(O)c1C/C=C(\C)CCC=C(C)C] | >2.06 | 0.96 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 10p | 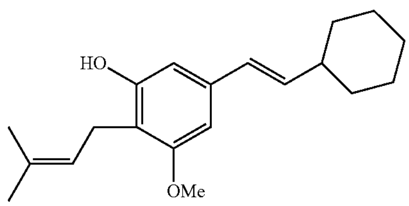 [SMILES: COc1cc(/C=C/C2CCCCC2)cc(O)c1CC=C(C)C] | 2.65 | >6.19 |
| 10q | 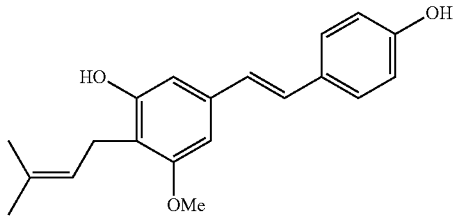 [SMILES: COc1cc(/C=C/c2ccc(O)cc2)cc(O)c1CC=C(C)C] | 1.39 | 2.35 |
| 10r | 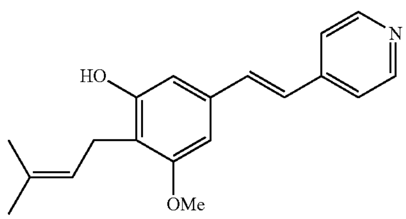 [SMILES: COc1cc(/C=C/c2ccncc2)cc(O)c1CC=C(C)C] | >0.69 | 3.23 |
| 10s | 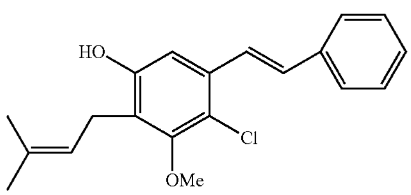 [SMILES: COc1c(Cl)c(/C=C/c2ccccc2)cc(O)c1CC=C(C)C] | >6.17 | 4.35 |
| 10t | 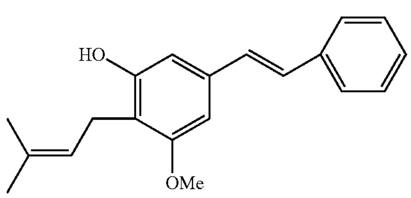 [SMILES: COc1cc(/C=C/c2ccccc2)cc(O)c1CC=C(C)C] | >0.69 | >2.06 |
| 10u | 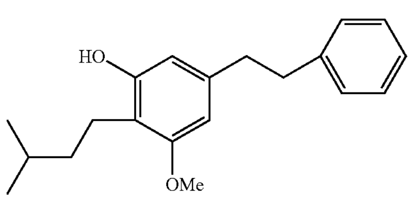 [SMILES: COc1cc(CCc2ccccc2)cc(O)c1CCC(C)C] | >2.06 | >6.19 |
| 10v | 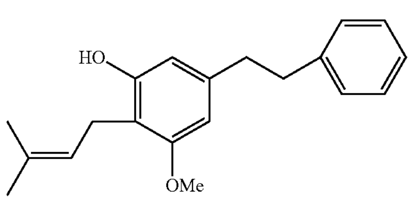 [SMILES: COc1cc(CCc2ccccc2)cc(O)c1CC=C(C)C] | >0.69 | >6.19 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 10w | 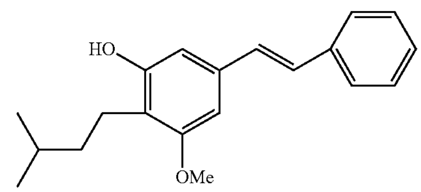 [SMILES: COc1cc(/C=C/c2ccccc2)cc(O)c1CCC(C)C] | 0.53 | 2.45 |
| 10x | 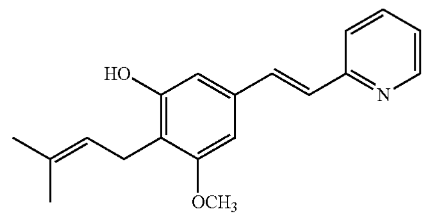 [SMILES: COc1cc(/C=C/c2ccccn2)cc(O)c1CC=C(C)C] | 0.09 | 0.42 |
| 10y | 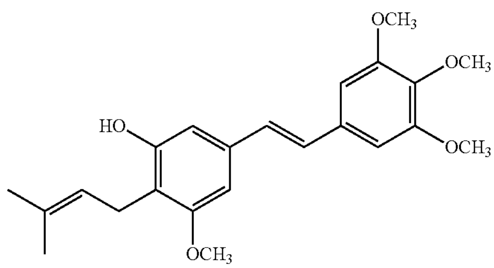 [SMILES: COc1cc(/C=C/c2cc(OC)c(OC)c(OC)c2)cc(O)c1CC=C(C)C] | 0.13 | 2.58 |
| 10z | 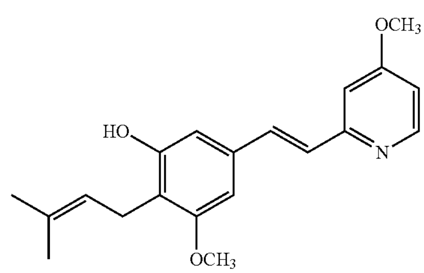 [SMILES: COc1ccnc(/C=C/c2cc(O)c(CC=C(C)C)c(OC)c2)c1] | 0.32 | 0.84 |
| 10a' | 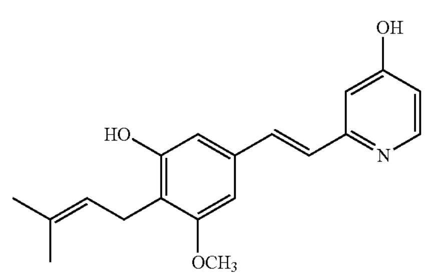 [SMILES: COc1cc(/C=C/c2cc(O)ccn2)cc(O)c1CC=C(C)C] | 0.17 | 0.41 |
| 10b' | 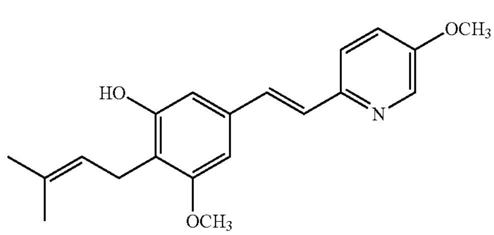 [SMILES: COc1ccc(/C=C/c2cc(O)c(CC=C(C)C)c(OC)c2)nc1] | 0.65 | 1.04 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 10c' | 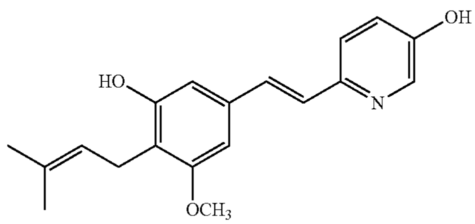 [SMILES: COc1cc(/C=C/c2ccc(O)cn2)cc(O)c1CC=C(C)C] | 0.31 | 2.31 |
| 10d' | 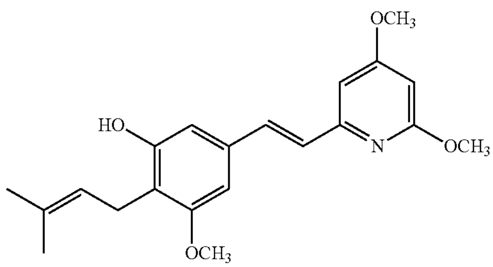 [SMILES: COc1cc(/C=C/c2cc(O)c(CC=C(C)C)c(OC)c2)nc(OC)c1] | 0.14 | 0.35 |
| 10e' | 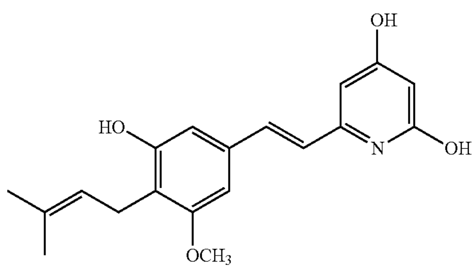 [SMILES: COc1cc(/C=C/c2cc(O)cc(O)n2)cc(O)c1CC=C(C)C] | 0.21 | 1.21 |
| 10f' | 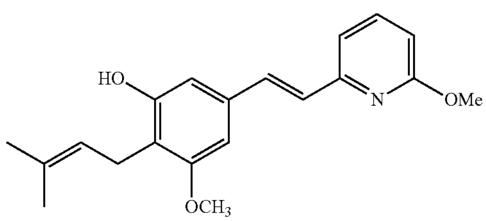 [SMILES: COc1cccc(/C=C/c2cc(O)c(CC=C(C)C)c(OC)c2)n1] | 0.23 | 2.31 |
| 10g' | 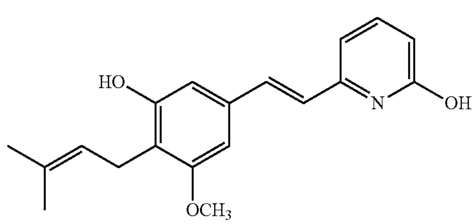 [SMILES: COc1cc(/C=C/c2cccc(O)n2)cc(O)c1CC=C(C)C] | 0.87 | 0.12 |
| 10h' | 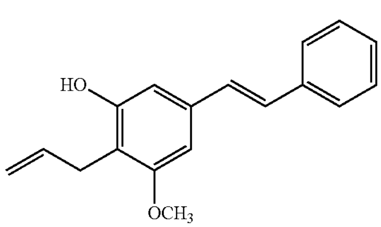 [SMILES: C=CCc1c(O)cc(/C=C/c2ccccc2)cc1OC] | 0.09 | 0.54 |

TABLE 1-continued
The structure and the anti-viral activity of the compounds proposed in this invention
| No. | Chemical Structure | Influenza A virus (hanfang359/95) IC$_{50}$ (μg/ml) | COX-B6 IC$_{50}$ (μg/ml) |
|---|---|---|---|
| 12 | 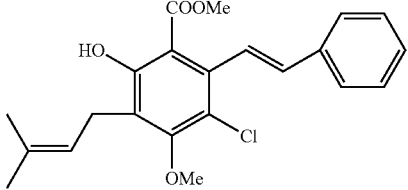 [SMILES: COC(=O)c1c(O)c(CC=C(C)C)c(OC)c(Cl)c1/C=C/c1ccccc1] | 6.17 | >6.17 |
| 13 | 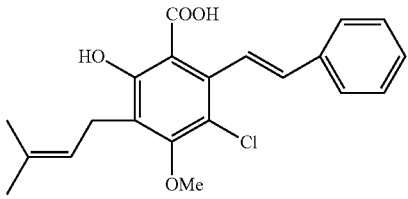 [SMILES: COc1c(Cl)c(/C=C/c2ccccc2)c(C(=O)O)c(O)c1CC=C(C)C] | >6.17 | 6.17 |
| 14 | 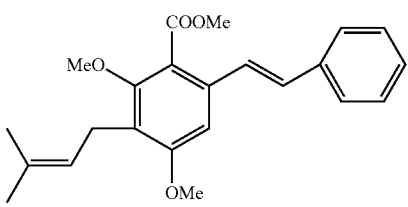 [SMILES: COc1cc(/C=C/c2ccccc2)c(C(=O)O)c(OC)c1CC=C(C)C] | >2.06 | 1.60 |
| 15 | 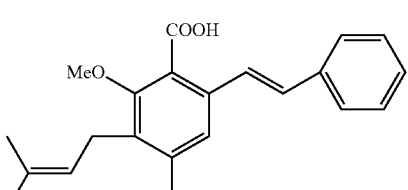 | >0.23 | >2.06 |
| 18 | 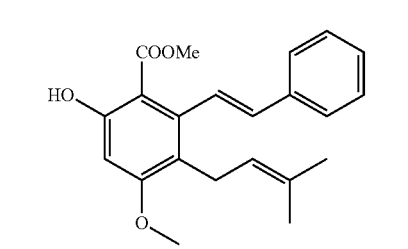 [SMILES: COC(=O)c1c(O)cc(OC)c(CC=C(C)C)c1/C=C/c1ccccc1] | >18.51 | >6.17 |
| 19 | 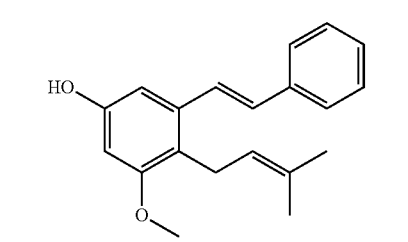 [SMILES: COc1cc(O)cc(/C=C/c2ccccc2)c1CC=C(C)C] | 14.37 | >2.06 |
| 20 | 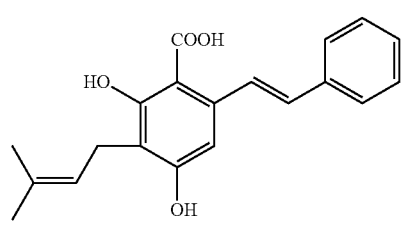 [SMILES: CC(C)=CCc1c(O)cc(/C=C/c2ccccc2)c(C(=O)O)c1O] | 0.21 | 4.65 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 21a | H$_3$CO-, OCH$_3$ stilbene structure | 1.32 | 4.23 |
| 21b | HO-, OH stilbene structure | 2.54 | 3.26 |
| 21d | H$_3$CO-, OCH$_3$ / OH, OCH$_3$ stilbene | 5.42 | 7.98 |
| 21e | HO-, OH / OH, OH stilbene | 2.38 | 4.86 |
| 21g | H$_3$CO-, OCH$_3$ / OH, OH methylstilbene | 4.25 | 6.84 |
| 21h | HO-, OH / OH, OH methylstilbene | 5.84 | 6.98 |

TABLE 1-continued

The structure and the anti-viral activity of the compounds proposed in this invention

| No. | Chemical Structure | Influenza A virus (hanfang359/95) IC$_{50}$ (µg/ml) | COX-B6 IC$_{50}$ (µg/ml) |
|---|---|---|---|
| 21j | 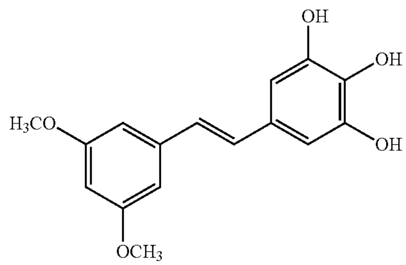 [SMILES: COc1cc(/C=C/c2cc(O)c(O)c(O)c2)cc(OC)c1] | 0.98 | 1.34 |
| 21k | 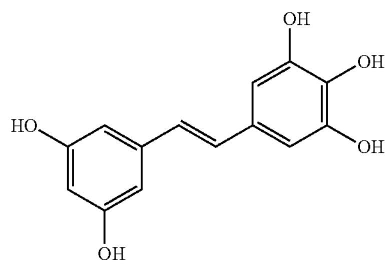 [SMILES: Oc1cc(O)cc(/C=C/c2cc(O)c(O)c(O)c2)c1] | 0.54 | 0.78 |
| 22 | 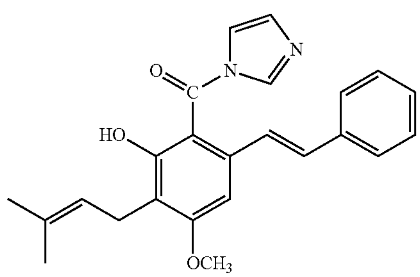 [SMILES: COc1cc(/C=C/c2ccccc2)c(C(=O)n2ccnc2)c(O)c1CC=C(C)C] | 1.25 | 2.37 |
| 23a | 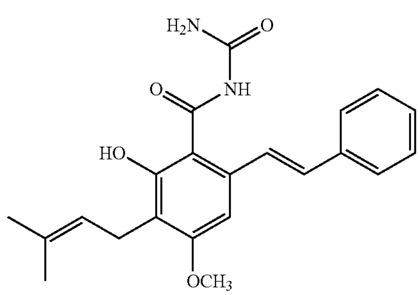 [SMILES: COc1cc(/C=C/c2ccccc2)c(C(=O)NC(N)=O)c(O)c1CC=C(C)C] | 0.09 | 0.32 |
| 23b | 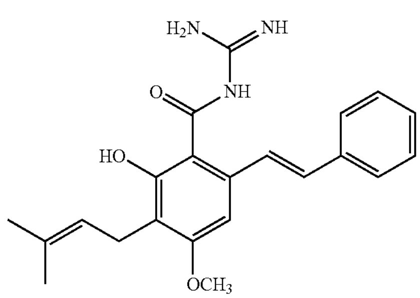 [SMILES: COc1cc(/C=C/c2ccccc2)c(C(=O)NC(=N)N)c(O)c1CC=C(C)C] | 0.13 | 0.24 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 24a | 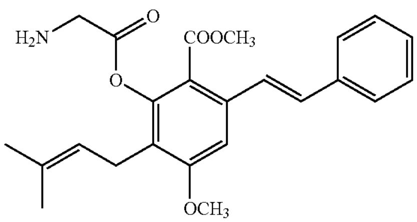 [SMILES: COC(=O)c1c(/C=C/c2ccccc2)cc(OC)c(CC=C(C)C)c1OC(=O)CN] | 2.31 | 3.21 |
| 24b | 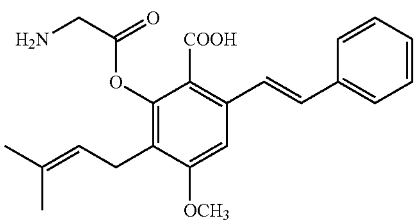 [SMILES: COc1cc(/C=C/c2ccccc2)c(C(=O)O)c(OC(=O)CN)c1CC=C(C)C] | 4.25 | 1.24 |
| 24c | 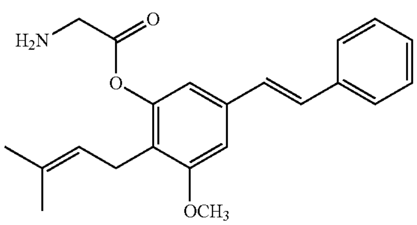 [SMILES: COc1cc(/C=C/c2ccccc2)cc(OC(=O)CN)c1CC=C(C)C] | 1.24 | 0.98 |
| 24d | 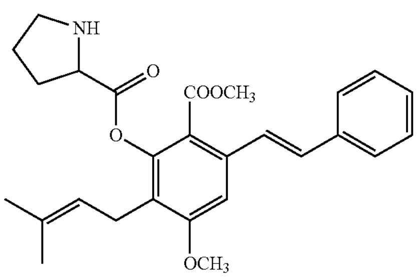 [SMILES: COC(=O)c1c(/C=C/c2ccccc2)cc(OC)c(CC=C(C)C)c1OC(=O)C1CCCN1] | 0.12 | 0.45 |
| 24e | 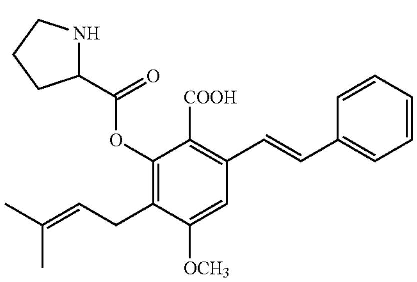 [SMILES: COc1cc(/C=C/c2ccccc2)c(C(=O)O)c(OC(=O)C2CCCN2)c1CC=C(C)C] | 0.42 | 0.13 |
| 24f | 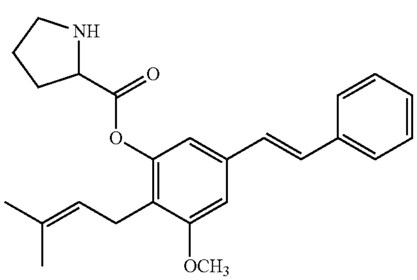 [SMILES: COc1cc(/C=C/c2ccccc2)cc(OC(=O)C2CCCN2)c1CC=C(C)C] | 0.13 | 0.21 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 24g | 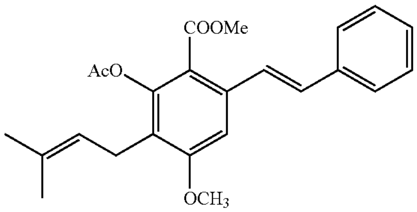 [SMILES: COC(=O)c1c(/C=C/c2ccccc2)cc(OC)c(CC=C(C)C)c1OC(C)=O] | 0.25 | 1.65 |
| 24h | 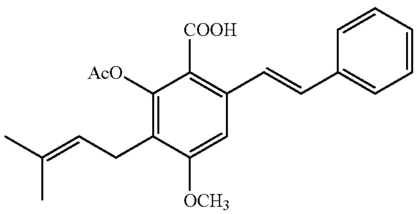 | 0.45 | 1.21 |
| 24i | 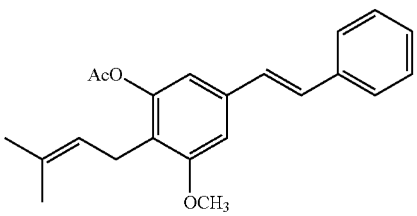 | 0.15 | 0.92 |
| 24j | 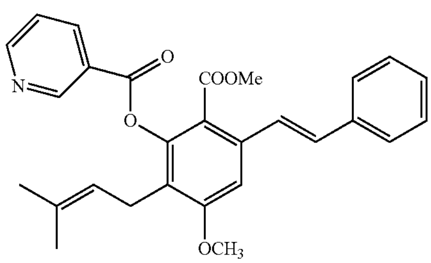 [SMILES: COC(=O)c1c(/C=C/c2ccccc2)cc(OC)c(CC=C(C)C)c1OC(=O)c1cccnc1] | 2.36 | 3.61 |
| 24k | 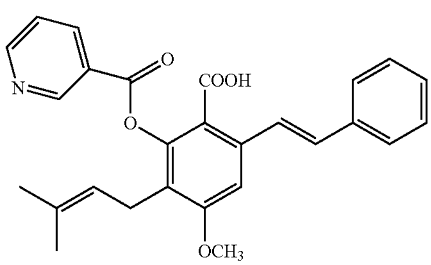 | 3.55 | 1.36 |
| 24l | 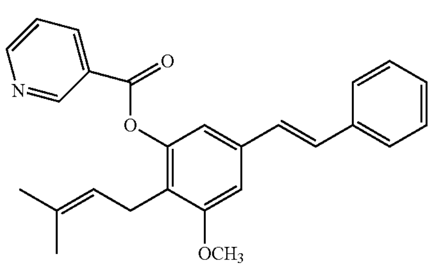 [SMILES: COc1cc(/C=C/c2ccccc2)cc(OC(=O)c2cccnc2)c1CC=C(C)C] | 1.04 | 0.95 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 24m | 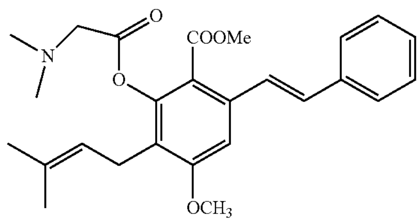 [SMILES: COC(=O)c1c(/C=C/c2ccccc2)cc(OC)c(CC=C(C)C)c1OC(=O)CN(C)C] | 6.52 | 3.46 |
| 24n | 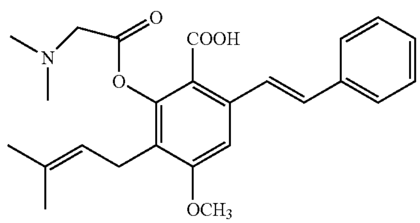 [SMILES: COc1cc(/C=C/c2ccccc2)c(C(=O)O)c(OC(=O)CN(C)C)c1CC=C(C)C] | 7.21 | 1.35 |
| 24o | 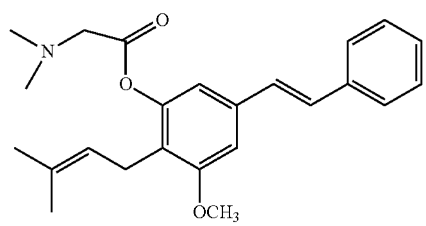 [SMILES: COc1cc(/C=C/c2ccccc2)cc(OC(=O)CN(C)C)c1CC=C(C)C] | 2.31 | 1.21 |
| 24p | 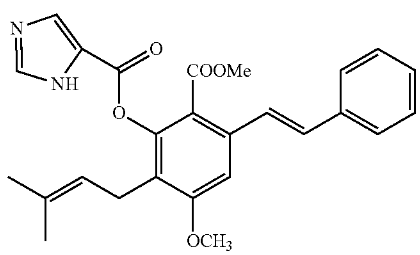 | 1.32 | 2.36 |
| 24q | 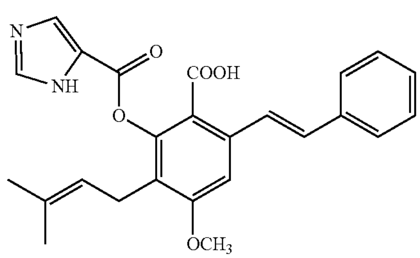 [SMILES: COC(=O)c1c(/C=C/c2ccccc2)cc(OC)c(CC=C(C)C)c1OC(=O)c1cnc[nH]1] | 1.98 | 1.35 |
| 24r | 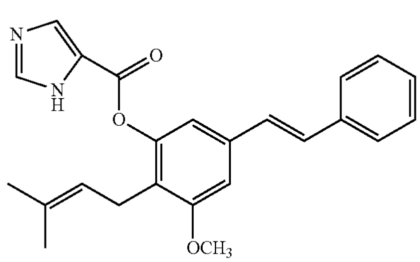 [SMILES: COc1cc(/C=C/c2ccccc2)cc(OC(=O)c2cnc[nH]2)c1CC=C(C)C] | 0.98 | 0.68 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 26a | 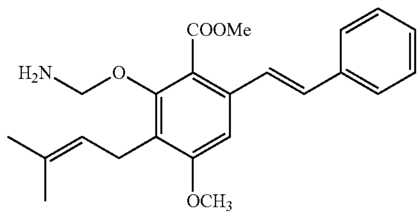 [SMILES: COC(=O)c1c(/C=C/c2ccccc2)cc(OC)c(CC=C(C)C)c1OCN] | 2.31 | 6.54 |
| 26b | 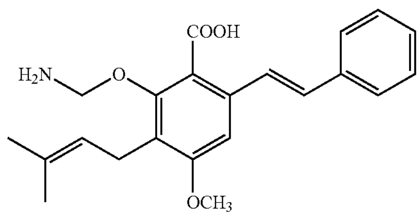 [SMILES: COc1cc(/C=C/c2ccccc2)c(C(=O)O)c(OCN)c1CC=C(C)C] | 3.65 | 3.54 |
| 26c | 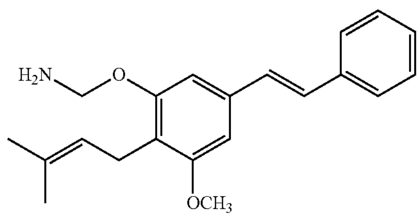 [SMILES: COc1cc(/C=C/c2ccccc2)cc(OCN)c1CC=C(C)C] | 1.35 | 2.64 |
| 26d | 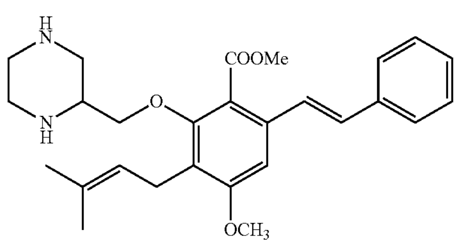 [SMILES: COC(=O)c1c(/C=C/c2ccccc2)cc(OC)c(CC=C(C)C)c1OCC1CNCCN1] | 1.36 | 2.75 |
| 26e | 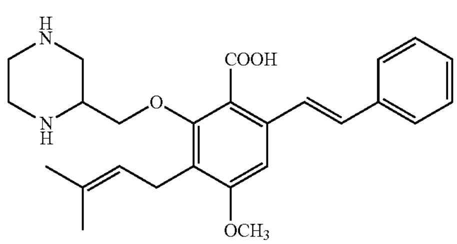 | 2.31 | 1.32 |
| 26f | 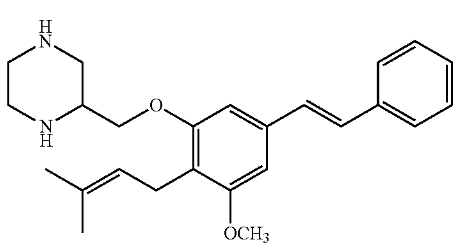 [SMILES: COc1cc(/C=C/c2ccccc2)cc(OCC2CNCCN2)c1CC=C(C)C] | 0.68 | 0.98 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 27a | 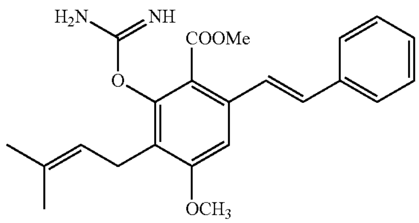 | 1.32 | 2.34 |
| 27b | 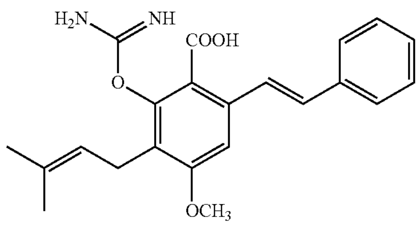 [SMILES: COc1cc(/C=C/c2ccccc2)c(C(=O)O)c(OC(=N)N)c1CC=C(C)C] | 2.14 | 1.24 |
| 27c | 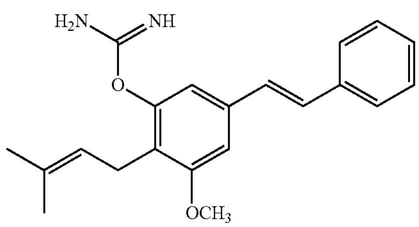 [SMILES: COc1cc(/C=C/c2ccccc2)cc(OC(=N)N)c1CC=C(C)C] | 0.54 | 0.92 |
| 29a | 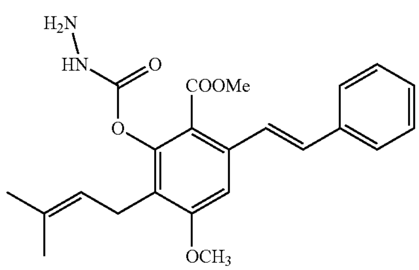 [SMILES: COC(=O)c1c(/C=C/c2ccccc2)cc(OC)c(CC=C(C)C)c1OC(=O)NN] | 0.98 | 1.36 |
| 29b | 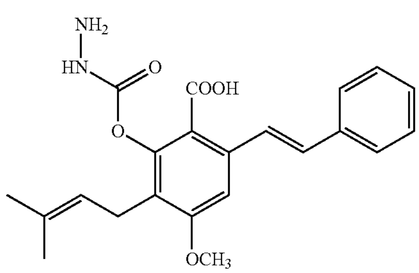 [SMILES: COc1cc(/C=C/c2ccccc2)c(C(=O)O)c(OC(=O)NN)c1CC=C(C)C] | 1.21 | 0.67 |
| 29c | 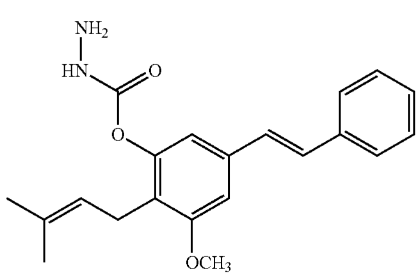 [SMILES: COc1cc(/C=C/c2ccccc2)cc(OC(=O)NN)c1CC=C(C)C] | 0.24 | 0.36 |

TABLE 1-continued

The structure and the anti-viral activity of the compounds proposed in this invention

| No. | Chemical Structure | Influenza A virus (hanfang359/95) IC$_{50}$ (μg/ml) | COX-B6 IC$_{50}$ (μg/ml) |
|---|---|---|---|
| 31a | 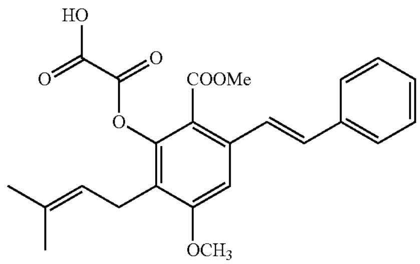 [SMILES: COC(=O)c1c(/C=C/c2ccccc2)cc(OC)c(CC=C(C)C)c1OC(=O)C(=O)O] | 0.14 | 2.31 |
| 31b | 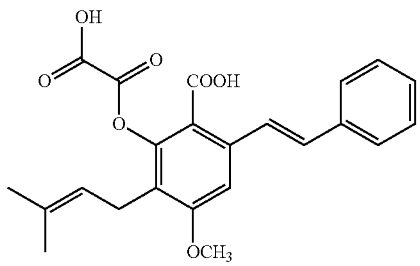 [SMILES: COc1cc(/C=C/c2ccccc2)c(C(=O)O)c(OC(=O)C(=O)O)c1CC=C(C)C] | 0.54 | 1.21 |
| 31c | 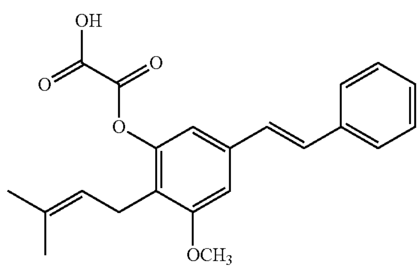 [SMILES: COc1cc(/C=C/c2ccccc2)cc(OC(=O)C(=O)O)c1CC=C(C)C] | 0.08 | 0.67 |
| 32 | 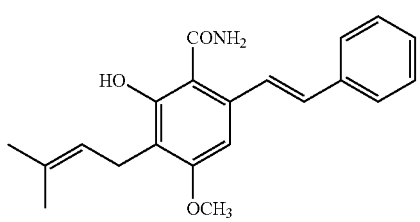 [SMILES: COc1cc(/C=C/c2ccccc2)c(C(N)=O)c(O)c1CC=C(C)C] | 0.21 | 0.54 |
| 33 | 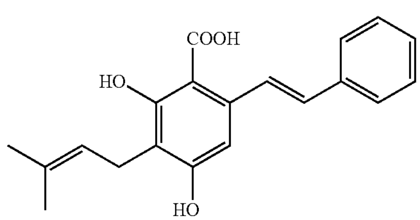 [SMILES: CC(C)=CCc1c(O)cc(/C=C/c2ccccc2)c(C(=O)O)c1O] | 2.35 | 2.31 |
| 34 | 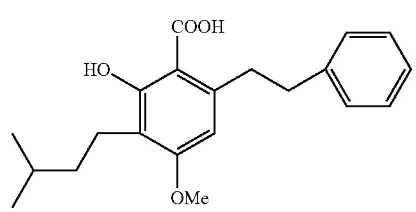 [SMILES: COc1cc(CCc2ccccc2)c(C(=O)O)c(O)c1CCC(C)C] | >6.17 | >2.06 |

TABLE 1-continued

The structure and the anti-viral activity of the compounds proposed in this invention

| No. | Chemical Structure | Influenza A virus (hanfang359/95) IC$_{50}$ (µg/ml) | COX-B6 IC$_{50}$ (µg/ml) |
|---|---|---|---|
| 36 | [structure: benzene ring with COOMe, HO, prenyl, OMe, phenethyl substituents] | >2.46 | >2.46 |
| 37 | [structure: benzene ring with COOH, HO, prenyl, OMe, phenethyl substituents] | >22.22 | >2.05 |
| 46 | [structure: benzene ring with COOMe, HO, isopentyl, OMe, styryl substituents] | 0.48 | 3.56 |
| 47 | [structure: benzene ring with COOH, HO, isopentyl, OMe, styryl substituents] | 2.47 | 2.13 |
| Oseltamivirphosphate | | 0.22 | NA |
| RBV | | 0.59 | 412.26 |

NA indicates no activity be detected.

The present invention also relates to the application of the compounds in inhibiting HIV, HCV viruses, the results are shown in Table 2, wherein the compound 1, 1a, 1b, 1c, 1E, 1f, 1i, 1j, 1l, 1s, 1u, 1x, 1y, 1z, 1a', 1b', 8, 8a, 8e, 8f, 8j, 8s, 8t, 8u, 8v, 8w, 9e, 10, 10b, 10h, 10i, 10j, 10l, 10m, 10o, 10q, 10t, 23a, 23b, 29a, 31b, 31c, 46 and so on showed stronger anti-HIV, HCV viral activities.

TABLE 2

The activities of the said compounds in inhibiting HIV, HCV viruses in vitro

| No. | HCV EC$_{50}$ (µg/ml) | HIV IC$_{50}$ (µg/ml) |
|---|---|---|
| 1 | 1.21 | 0.27 |
| 1a | 1.04 | 1.01 |
| 1b | 0.67 | 1.22 |
| 1c | 2.69 | 1.64 |
| 1d | 3.31 | 1.86 |
| 1e | 0.47 | 2.70 |
| 1f | 0.53 | 1.45 |
| 1g | 1.43 | 0.68 |
| 1h | 2.60 | 2.39 |
| 1i | 0.59 | 1.31 |
| 1j | 0.77 | 1.02 |
| 1k | 1.03 | 2.40 |
| 1l | 0.65 | 1.64 |
| 1m | 6.17 | 1.07 |
| 1n | 2.61 | 0.99 |
| 1o | 1.47 | 1.76 |
| 1p | 8.62 | 1.06 |
| 1q | 2.30 | 1.86 |
| 1r | 6.79 | 6.53 |
| 1s | 0.84 | 0.75 |
| 1t | 1.58 | 1.07 |
| 1u | 0.84 | 0.16 |
| 1v | 1.25 | 1.48 |
| 1w | 2.06 | 2.87 |
| 1x | 0.84 | 0.35 |
| 1y | 0.86 | 0.63 |
| 1z | 3.53 | 2.64 |
| 1a' | 0.94 | 1.38 |

TABLE 2-continued

The activities of the said compounds in inhibiting HIV, HCV viruses in vitro

| No. | HCV EC$_{50}$ (μg/ml) | HIV IC$_{50}$ (μg/ml) |
|---|---|---|
| 1b' | 0.88 | 3.19 |
| 1c' | 1.30 | 1.61 |
| 6 | >12.25 | >2.06 |
| 7 | >2.06 | >6.38 |
| 8 | 0.79 | 1.06 |
| 8a | 1.09 | 1.64 |
| 8b | 5.18 | 0.52 |
| 8c | 3.06 | 1.99 |
| 8d | 5.17 | 0.86 |
| 8e | 0.72 | 1.35 |
| 8f | 0.88 | 1.16 |
| 8g | 1.32 | 2.34 |
| 8h | 1.42 | 2.66 |
| 8i | 3.47 | 3.80 |
| 8j | 0.83 | 0.68 |
| 8l | 5.95 | 5.17 |
| 8m | 2.28 | 3.17 |
| 8n | 1.06 | 2.17 |
| 8o | 0.92 | 2.96 |
| 8p | 11.37 | 21.11 |
| 8q | 7.63 | 2.10 |
| 8r | 3.14 | 4.01 |
| 8s | 0.84 | 0.52 |
| 8t | 0.64 | 0.60 |
| 8u | 0.67 | 1.49 |
| 8v | 2.39 | 1.01 |
| 8w | 0.60 | 1.09 |
| 8x | 1.87 | 0.79 |
| 8y | 4.33 | 6.80 |
| 9a | 1.47 | 4.02 |
| 9b | 10.01 | 4.37 |
| 9c | 16.19 | 5.60 |
| 9d | 1.22 | 2.01 |
| 9e | 0.66 | 0.73 |
| 9f | 6.09 | 0.14 |
| 9g | 5.10 | 0.79 |
| 9h | 1.33 | 3.38 |
| 10 | 0.56 | 0.21 |
| 10a | 1.60 | 2.02 |
| 10b | 0.59 | 0.30 |
| 10c | 7.17 | 0.35 |
| 10d | 2.37 | 1.05 |
| 10e | 1.90 | 1.33 |
| 10f | 0.87 | 0.46 |
| 10g | 3.09 | 1.18 |
| 10h | 0.74 | 0.96 |
| 10i | 0.69 | 0.26 |
| 10j | 0.87 | 0.66 |
| 10k | 0.99 | 1.06 |
| 10l | 0.95 | 2.20 |
| 10m | 1.75 | 2.33 |
| 10n | 0.89 | 1.43 |
| 10o | 1.32 | 0.96 |
| 10p | 2.95 | 7.19 |
| 10q | 0.89 | 2.38 |
| 10r | 1.71 | 1.73 |
| 10s | 5.17 | 2.75 |
| 10t | 0.61 | 2.36 |
| 10u | 4.06 | 6.39 |
| 10v | 1.73 | 1.36 |
| 10w | 2.59 | 0.75 |
| 10x | 0.93 | 1.09 |
| 10y | 1.39 | 1.66 |
| 10z | 1.19 | 2.83 |
| 10a' | 1.41 | 1.33 |
| 10b' | 1.27 | 2.34 |
| 10c' | 0.82 | 1.39 |
| 10d' | 0.65 | 1.30 |
| 10e' | 1.87 | 0.71 |
| 10f' | 0.61 | 1.04 |
| 10g' | 2.30 | 3.93 |
| 12 | 6.87 | 8.17 |
| 13 | 3.11 | 6.76 |
| 14 | 1.77 | 1.32 |
| 15 | 0.83 | 1.43 |
| 18 | 8.51 | 0.34 |
| 19 | 10.37 | 9.03 |
| 20 | 0.72 | 0.39 |
| 21a | 2.83 | 1.10 |
| 21b | 1.47 | 0.88 |
| 21d | 3.37 | 0.63 |
| 21e | 2.06 | 6.33 |
| 21g | 0.90 | 1.27 |
| 21h | 4.46 | 5.28 |
| 21j | 1.33 | 1.04 |
| 21k | 8.36 | 10.32 |
| 22 | 0.68 | 0.35 |
| 23a | 0.66 | 0.74 |
| 23b | 0.53 | 3.90 |
| 24a | 0.98 | 1.79 |
| 24b | 1.68 | 2.01 |
| 24c | 0.94 | 2.78 |
| 24d | 0.87 | 0.81 |
| 24e | 1.48 | 0.69 |
| 24f | 0.69 | 1.01 |
| 24g | 0.83 | 0.33 |
| 24h | 2.39 | 1.33 |
| 24i | 0.99 | 2.09 |
| 24j | 1.35 | 2.65 |
| 24k | 4.87 | 2.17 |
| 24l | 1.60 | 1.40 |
| 24m | 0.80 | 2.60 |
| 24n | 1.97 | 3.12 |
| 24o | 1.34 | 0.69 |
| 24p | 0.77 | 0.31 |
| 24q | 1.54 | 2.85 |
| 24r | 1.05 | 2.31 |
| 26a | 2.09 | 1.73 |
| 26b | 5.66 | 7.83 |
| 26c | 2.07 | 3.18 |
| 26d | 1.53 | 1.36 |
| 26e | 2.28 | 2.77 |
| 26f | 1.39 | 1.61 |
| 27a | 1.34 | 2.48 |
| 27b | 1.83 | 4.91 |
| 27c | 1.26 | 2.03 |
| 29a | 0.51 | 0.43 |
| 29b | 1.36 | 1.88 |
| 29c | 0.89 | 0.60 |
| 31a | 0.71 | 1.30 |
| 31b | 0.99 | 2.80 |
| 31c | 0.77 | 0.29 |
| 32 | 1.37 | 0.16 |
| 33 | 1.55 | 2.01 |
| 34 | 8.27 | 0.72 |
| 36 | 3.86 | 1.06 |
| 37 | 12.20 | 2.09 |
| 46 | 0.77 | 2.51 |
| 47 | 1.47 | 1.13 |

The present invention also relates to the application of said compounds in neural protection (effects on PC12 cell injury), this invention measured the protective effect of said compounds on PC12 cells from serum-deprived injury, as well as rotenone injury (results shown in Table 3). Compounds proposed in this invention showed significant protective effect on serum-deprived injury to PC12 cells and rotenone injury to PC12 cells, wherein the compound 1p, 1r, 1u, 1w, 1z, 1a, 1b, 1d, 8d, 8m, 8p, 8q, 8w, 9e, 9 g, 10c, 10j, 10k, 10l, 10m, 10o, 10p, 10t, 10u and 10v, 10c, 10d, 21d, 24b, 24k, 24q, 27b, 32, etc. showed the strongest activities.

TABLE 3

Neuroprotective effect of the said compounds

| No. | serum-deprived | rotenone |
|---|---|---|
| Control | 100.0 ± 9.2 | 100.0 ± 8.9 |
| ModEl | 69.3 ± 4.1 | 73.2 ± 7.8 |
| 1 | 19.3 ± 1.6 | 72.3 ± 5.9 |
| 1a | 16.7 ± 0.6 | 62.4 ± 3.8 |
| 1b | 15.7 ± 0.3 | 68.2 ± 8.0 |
| 1c | 16.1 ± 0.7 | 77.2 ± 0.6 |
| 1d | 37.8 ± 2.4 | 70.8 ± 2.4 |
| 1e | 30.6 ± 12.0 | 55.6 ± 9.9 |
| 1f | 31.7 ± 10.3 | 58.0 ± 4.5 |
| 1g | 59.8 ± 11.4 | 77.7 ± 12.9 |
| 1h | 43.8 ± 8.8 | 70.0 ± 7.1 |
| 1i | 28.3 ± 7.6 | 55.1 ± 4.8 |
| 1j | 27.7 ± 6.3 | 59.8 ± 7.7 |
| 1k | 19.2 ± 0.5 | 60.4 ± 3.2 |
| 1l | 27.2 ± 7.2 | 58.4 ± 1.4 |
| 1m | 21.0 ± 2.2 | 74.4 ± 4.4 |
| 1n | 17.3 ± 2.4 | 62.9 ± 2.7 |
| 1o | 28.1 ± 11.9 | 61.0 ± 2.8 |
| 1p | 81.2 ± 3.2 | 82.0 ± 2.3 |
| 1q | 79.6 ± 2.8 | 78.9 ± 5.3 |
| 1r | 84.3 ± 6.3 | 86.3 ± 5.4 |
| 1s | 89.8 ± 3.2 | 88.7 ± 6.1 |
| 1t | 85.1 ± 2.1 | 84.6 ± 1.2 |
| 1u | 89.3 ± 2.3 | 90.0 ± 3.2 |
| 1v | 79.9 ± 1.6 | 87.2 ± 2.6 |
| 1w | 89.3 ± 5.4 | 88.9 ± 2.5 |
| 1x | 84.9 ± 2.5 | 85.6 ± 3.3 |
| 1y | 87.6 ± 1.6 | 89.7 ± 1.9 |
| 1z | 91.6 ± 1.6 | 89.9 ± 4.8 |
| 1a' | 88.7 ± 4.9 | 87.2 ± 4.3 |
| 1b' | 88.9 ± 1.9 | 87.2 ± 6.31 |
| 1c' | 85.9 ± 4.7 | 85.6 ± 3.8 |
| 1d' | 89.9 ± 4.5 | 88.6 ± 4.5 |
| 6 | 62.4 ± 7.0 | 74.4 ± 5.2 |
| 7 | 66.8 ± 6.0 | 77.0 ± 3.6 |
| 8' | 40.0 ± 3.6 | 74.3 ± 5.0 |
| 8 | 76.6 ± 5.8 | 78.9 ± 5.7 |
| 8a | 65.2 ± 6.9 | 76.9 ± 4.1 |
| 8b | 75.1 ± 3.6 | 80.7 ± 6.4 |
| 8c | 67.3 ± 10.0 | 71.9 ± 6.1 |
| 8d | 82.0 ± 3.2 | 84.4 ± 3.6 |
| 8e | 58.5 ± 8.7 | 74.5 ± 3.8 |
| 8f | 60.7 ± 12.6 | 74.1 ± 1.8 |
| 8g | 29.1 ± 11.6 | 59.0 ± 4.6 |
| 8h | 35.4 ± 10.6 | 72.4 ± 4.3 |
| 8i | 46.4 ± 16.6 | 69.4 ± 2.6 |
| 8j | 34.4 ± 3.2 | 63.6 ± 5.0 |
| 8l | 51.1 ± 17.0 | 64.7 ± 1.8 |
| 8m | 84.7 ± 5.0 | 69.8 ± 5.2 |
| 8n | 53.7 ± 3.8 | 78.0 ± 9.2 |
| 8o | 69.3 ± 5.6 | 70.6 ± 6.3 |
| 8p | 82.3 ± 5.6 | 84.6 ± 5.9 |
| 8q | 79.8 ± 5.8 | 80.5 ± 6.5 |
| 8r | 74.5 ± 5.7 | 69.8 ± 8.4 |
| 8s | 79.8 ± 5.2 | 76.8 ± 5.4 |
| 8w | 89.7 ± 5.4 | 84.9 ± 5.9 |
| 8x | 79.8 ± 2.6 | 76.5 ± 1.8 |
| 8y | 49.8 ± 2.6 | 48.9 ± 6.5 |
| 8a' | 87.9 ± 2.5 | 88.0 ± 6.9 |
| 9a | 49.6 ± 13.2 | 70.9 ± 6.4 |
| 9b | 42.9 ± 11.3 | 74.5 ± 12.1 |
| 9c | 47.9 ± 11.4 | 62.9 ± 3.8 |
| 9d | 55.4 ± 10.7 | 71.0 ± 1.5 |
| 9e | 91.3 ± 2.4 | 90.8 ± 4.3 |
| 9f | 58.9 ± 2.6 | 68.5 ± 4.9 |
| 9g | 89.4 ± 2.3 | 87.4 ± 1.9 |
| 9h | 84.5 ± 5.1 | 79.8 ± 2.1 |
| 10 | 34.7 ± 9.8 | 69.9 ± 5.8 |
| 10a | 78.2 ± 4.1 | 79.8 ± 5.6 |
| 10b | 74.8 ± 5.2 | 74.6 ± 6.3 |
| 10c | 81.6 ± 2.6 | 80.3 ± 6.2 |
| 10d | 79.3 ± 5.4 | 78.9 ± 6.1 |
| 10e | 65.3 ± 2.3 | 70.2 ± 8.1 |
| 10f | 74.5 ± 6.5 | 76.5 ± 8.0 |
| 10g | 81.3 ± 2.5 | 80.3 ± 3.2 |
| 10h | 65.8 ± 9.2 | 67.8 ± 8.5 |
| 10i | 78.5 ± 7.4 | 79.1 ± 7.2 |
| 10J | 82.3 ± 2.5 | 84.6 ± 5.2 |
| 10k | 85.6 ± 3.2 | 84.6 ± 2.4 |
| 10l | 81.3 ± 2.9 | 84.6 ± 6.2 |
| 10m | 89.3 ± 6.4 | 85.3 ± 7.1 |
| 10n | 79.6 ± 2.8 | 78.6 ± 3.2 |
| 10o | 86.3 ± 3.8 | 87.6 ± 5.4 |
| 10p | 84.6 ± 2.7 | 86.7 ± 9.1 |
| 10q | 79.5 ± 1.4 | 76.8 ± 5.8 |
| 10r | 68.5 ± 2.4 | 58.4 ± 6.5 |
| 10s | 78.5 ± 6.3 | 79.8 ± 3.5 |
| 10t | 84.9 ± 2.5 | 85.6 ± 6.3 |
| 10u | 87.6 ± 3.2 | 85.4 ± 2.3 |
| 10v | 85.2 ± 4.1 | 87.1 ± 2.5 |
| 10w | 79.1 ± 4.6 | 78.2 ± 5.8 |
| 10x | 78.9 ± 4.6 | 78.9 ± 5.4 |
| 10y | 89.1 ± 5.4 | 89.5 ± 2.5 |
| 10z | 84.6 ± 3.9 | 87.0 ± 5.1 |
| 10a' | 86.3 ± 1.2 | 89.2 ± 3.2 |
| 10b' | 84.3 ± 2.5 | 85.9 ± 3.4 |
| 10c' | 89.7 ± 2.4 | 91.2 ± 2.1 |
| 10d' | 91.2 ± 3.2 | 94.3 ± 5.4 |
| 10e' | 87.9 ± 4.7 | 88.9 ± 2.8 |
| 10f' | 80.5 ± 3.2 | 79.1 ± 5.6 |
| 10g' | 71.0 ± 5.2 | 63.5 ± 2.1 |
| 10h' | 87.6 ± 4.3 | 86.7 ± 4.5 |
| 12 | 60.2 ± 5.1 | 74.5 ± 3.2 |
| 13 | 21.3 ± 4.2 | 74.4 ± 6.4 |
| 14 | 69.7 ± 5.6 | 73.7 ± 8.5 |
| 15 | 74.1 ± 2.5 | 83.1 ± 5.7 |
| 18 | 77.8 ± 6.3 | 74.9 ± 2.9 |
| 19 | 62.7 ± 5.8 | 80.1 ± 6.9 |
| 20 | 32.3 ± 5.6 | 67.3 ± 3.1 |
| 21a | 81.2 ± 2.4 | 80.5 ± 2.3 |
| 21b | 74.6 ± 3.5 | 78.9 ± 6.8 |
| 21d | 88.7 ± 6.3 | 89.8 ± 2.8 |
| 21e | 85.6 ± 4.2 | 87.4 ± 2.5 |
| 21g | 80.2 ± 1.5 | 82.3 ± 3.1 |
| 21h | 74.8 ± 2.6 | 71.2 ± 3.8 |
| 21j | 69.3 ± 2.5 | 75.6 ± 4.6 |
| 21k | 74.5 ± 5.8 | 71.3 ± 8.0 |
| 22 | 87.8 ± 2.9 | 85.6 ± 1.6 |
| 23a | 87.9 ± 5.8 | 85.6 ± 8.7 |
| 23b | 79.8 ± 4.6 | 81.3 ± 5.0 |
| 24b | 89.7 ± 5.6 | 88.3 ± 5.2 |
| 24e | 87.2 ± 2.4 | 86.9 ± 5.8 |
| 24h | 88.9 ± 5.4 | 87.8 ± 6.3 |
| 24k | 89.6 ± 2.3 | 85.6 ± 2.1 |
| 24n | 75.8 ± 3.2 | 79.8 ± 5.6 |
| 24q | 92.3 ± 1.2 | 90.5 ± 5.6 |
| 26b | 88.2 ± 4.1 | 89.7 ± 6.3 |
| 26e | 85.6 ± 2.9 | 87.6 ± 5.6 |
| 27b | 91.5 ± 6.1 | 92.3 ± 2.6 |
| 29b | 74.5 ± 4.6 | 78.9 ± 5.6 |
| 31b | 88.6 ± 2.6 | 80.5 ± 6.4 |
| 32 | 94.5 ± 2.3 | 92.3 ± 1.2 |
| 33 | 16.8 ± 0.4 | 75.6 ± 2.1 |
| 36 | 41.0 ± 15.4 | 72.2 ± 12.2 |
| 37 | 29.0 ± 11.2 | 60.4 ± 7.8 |
| 46 | 59.0 ± 14.3 | 73.9 ± 2.9 |
| 47 | 30.2 ± 9.9 | 61.9 ± 4.1 |

The present invention also relates to anti-osteoporotic effect of said compounds. According to literature reports, pigeonpea stilbene-type compounds belong to phytoestrogens, the anti-osteoporosis effect of natural products has to do with their estrogen-like effects. This invention studied and confirmed the protective effect of pure cajanine obtained by chemical means on bone osteoporosis in ovariectomized rats, the results showed a stronger in vivo anti-osteoporotic effect than clinical drug raloxifene.

In addition, as mentioned in the background of this invention, the anti-tumor, hypoglycemic, hypolipidemic, anti-inflammatory and analgesic effects of pigeon pea stilbene-type extracts and cajanine, cajanine A, cajanine C have been widely studied and reported. The compounds proposed in this invention are structural analogs of natural lead compounds cajanine, cajanine A and cajanine C, it is a matter of course that the compounds proposed in the present invention possess similar antitumor, hypoglycemic, hypolipidemic, anti-inflammatory and analgesic effects. Accordingly, the present invention also relates to the application of anti-tumor, hypoglycemic, hypolipidemic, anti-inflammatory and analgesic effects of said compounds in medicinal practice.

The present invention also provides an effective pharmaceutical composition used for anti-viral and bacterial infections, neuroprotection, anti-metabolic diseases (such as osteoporosis, hyperlipidemia, hyperglycemia), said pharmaceutical composition comprises a therapeutically effective amount of compound having one of the formula I, II, III, IV or V structures, or their pharmaceutically acceptable salt thereof, and comprises one or more pharmaceutically acceptable pharmaceutical adjuvants.

Wherein, as an active ingredient, the weight content of said compound having one of the general formula I, II, III, IV, V, or their pharmaceutically acceptable salt in the pharmaceutical composition is in the range of 0.1% to 99.5%. Preferably, the pharmaceutical composition contains a weight ratio of 0.5% to 99.5% of the active ingredient.

Further, the present invention provides the application of a pharmaceutical composition in the preparation of medicaments for bacterial and viral infection treatment, neuroprotection, treatment of metabolic diseases (such osteoporosis, hyperlipidemia, hyperglycemia).

EXPLANATION OF THE DRAWINGS

FIG. 1 showed the chemical structures of compounds in pigeon pea stilbene extract.

EMBODIMENTS

Example 1

Preparation of methyl 2,4-dihydroxy-6-methyl-bensoate (2)

Dissolve methyl acetoacetate (50 g, 0.43 mol) in 300 ml diethyl ether at room temperature, add NaH (15.50 g 0.45 mol, 70%), then add dropwise diketene (37 g, 0.45 mol) solution in diethyl ether at the same temperature, when the addition finishes, react at room temperature for 3-4h, when the reaction mixture becomes cloudy yellow liquid. After termination of the reaction, pour the mixture into 500 ml ice water, separate the ether layer, extract the aqueous layer twice with 50 ml ether, pool the ether layer, wash with saturated brine, dried over anhydrous magnesium sulfate overnight. Filter the solution and the remove ether by rotary evaporation, dissolve the residue with of petroleum ether and ethyl acetate 8:1 mixture, feed the solution into a silica gel column, evaporate the solvent in the eluent to obtain 35 g white solid as the target product (45%). $^1$H-NMR (400M, DMSO-$d_6$) δ (ppm): 2.26 (s, 3H), 3.78 (s, 3H), 6.14 (d, J=2.4 Hz, 1H), 6.16 (d, J=2.4 Hz, 1H), 9.95 (s, 1H), 10.66 (s, 1H)

Example 2

Preparation of methyl 2,4-dimethoxy-6-methyl-benzoate (3)

Dissolve compound 2 (12 g, 0.066 mol) in 50 ml acetone, add potassium carbonate (27.3 g, 0.198 mol) and iodomethane (28 g, 0.198 mol) into the solution, heat the mixture to reflux for 3 h, then stop the reaction, pour the reaction mixture into 100 ml water, extract with ethyl acetate (3×50 ml), pool the organic layers, wash the organic layer successively with 10% sodium hydroxide solution, 10% hydrochloric acid and saturated brine. Dry the organic layer over anhydrous magnesium sulfate. Filter the solution and remove the solvent by rotary evaporation to obtain a colorless oily material, re-crystallize with petroleum ether/ethyl acetate to obtain 13.5 g colorless crystals (97%). $^1$H-NMR (400M, CDCl$_3$) δ (ppm): 2.28 (s, 3H), 3.80 (s, 6H), 3.88 (s, 3H), 6.31 (s, 2H)

Example 3

Preparation of methyl 2-(bromomethyl)-4,6-dimethoxy-benzoate (4)

Dissolve compound 3 (10 g, 0.0476 mol) in 50 ml carbon tetrachloride, heat to reflux under nitrogen protection, add portion wise a mixture of NBS (8.5 g, 0.0476 mol) and BPO (0.11 g, 0.476 mmol), after finishing the addition, reflux to react for 1 h. Then stop the reaction, cool and filter the mixture, spin-dry filtrate to obtain a pale yellow solid, re-crystallize from ethanol to obtain 11.3 g white solid (82%). $^1$H-NMR (400M, CDCl$_3$) δ (ppm): 3.85 (s, 3H), 3.93 (s, 3H), 3.96 (s, 3H), 4.66 (s, 2H), 6.47 (s, 1H), 6.74 (s, 1H).

Example 4

Preparation of Methyl 2-(diethyl methylenephosphonite)-4,6-dimethoxybenzoate (5)

Heat to reflux a mixture of compound 4 (12 g, 0.0326 mol) and triethyl phosphite (10.83 g, 0.065 mol) for 2 h. Stop the reaction, cool the mixture, evaporate the excessive triethyl phosphite, dissolve the residue with a 40:1 mixture of dichloromethane:methanol, feed the solution into a silica gel column, evaporate the solvent in the eluent to obtain 12.8 g white solid (92%). $^1$H-NMR (400M, CDCl$_3$) δ (ppm): 1.26 (t, J=6.4 Hz, 6H), 3.78 (d, J=22.8 Hz, 2H), 3.80 (s, 3H), 3.90 (s, 3H), 3.92 (s, 3H), 4.02 (q, J=6.4 Hz, 4H), 6.43 (s, 1H), 6.76 (s, 1H).

Example 5

Preparation of methyl 2,4-dimethoxy-6-[(E)-styryl]benzoate (6)

Dissolve compound 5 (10 g, 0.0289 mol) in 100 ml tetrahydrofuran, add into the solution NaH (1.09 g, 0.0318 mol) and benzaldehyde (3.68 g, 0.0347 mol), heat to reflux for 2 h, stop the reaction, pour the mixture into 200 ml water, extract with ethyl acetate (3×100 ml), pool the organic layers, wash the organic layer with saturated brine, dry over anhydrous magnesium sulfate. Filter the solution and remove the solvent by rotary evaporation, recrystallize the residual oil with petroleum ether/ethyl acetate to obtain 6.2 g colorless crystals (72%). $^1$H-NMR (400M, CDCl$_3$) δ (ppm): 3.83 (s, 3H), 3.88 (s, 3H), 3.92 (s, 3H), 6.42 (s, 1H), 6.77 (s, 1H), 7.06 (dd, J=16 Hz, 2H), 7.29 (m, 1H), 7.35 (t, J=7.2 Hz, 2H), 7.47 (d, J=7.2 Hz, 2H).

Example 6

Preparation of methyl 2-hydroxy-4-methoxy-6-[(E)-styryl]benzoate (7)

Dissolve compound 6 (6 g, 0.0201 mol) in 50 ml dichloromethane, add drop wise BBr$_3$ solution in methylene chloride (24 ml, 1M) at 0° C., react at room temperature for 1 h. Wash the reaction solution with water, dry over anhydrous magnesium sulfate. Filter the solution and remove the solvent by rotary evaporation, dissolve the residue with petroleum ether/diethyl ether and feed the solution to a silica gel column, evaporate the solvent in eluent to obtain 5.4 g white solid (95%). $^1$H-NMR (400M, CDCl$_3$) δ (ppm): 3.79 (s, 3H), 3.82 (s, 3H), 6.40 (d, J=2.4 Hz, 1H), 6.80 (d, J=2.4 Hz, 1H), 7.15 (dd, J=16 Hz, 2H), 7.28 (t, J=7.2 Hz, 1H), 7.38 (t, J=7.2 Hz, 2H), 7.52 (d, J=7.2 Hz, 2H), 10.28 (s, 1H).

Example 7

Preparation of methyl 2-hydroxy-3-isopentenyl-4-methoxy-6-[(E)-styryl]-benzoate (8)

Dissolve compound 7 (5 g, 0.0176 mol) in 50 ml ether, add sodium metal (0.43 g, 0.0184 mol) into the solution, stir at room temperature for 4 h, then add in isopentenyl bromide (3.2 g, 0.0211 mol), reflux to react for 4 h, stop the reaction. Wash the reaction solution successively with water and saturated brine, separate the organic layer. Desiccate the organic layer over anhydrous magnesium sulfate, filter the solution and remove the solvent by rotary evaporation to obtain a yellow oil which is then feeded to silica gel column chromatography and evaporate the solvent in the eluent to obtain 3.8 g white solid (61%). $^1$H-NMR (400M, CDCl$_3$) δ (ppm): 1.61 (s, 3H), 1.71 (s, 3H), 34 (d, J=6.8 Hz, 2H), 3.91 (s, 3H), 3.94 (s, 3H), 5.12 (t, J=6.8 Hz, 1H), 6.78 (s, 1H), 7.00 (d, J=16 Hz, 1H), 7.27 (t, J=7.2 Hz, 1H), 7.38 (t, J=7.2 Hz, 2H), 7.52 (d, J=7.2 Hz, 2H), 7.84 (d, J=16 Hz, 1H), 11.66 (s, 1H).

Example 8

Preparation of 2-hydroxy-3-isopentenyl-4-methoxy-6-[(E)-styryl]benzoic acid (compound 1, cajanine)

Dissolve compound 8 (3 g, 0.0085 mol) in 30 ml 20% aqueous sodium hydroxide solution, heat to reflux for 2 h, cool the solution to stop the reaction. Add in 10% dilute hydrochloric acid to adjust the pH to less than 2 to cause a formation of a large amount of white precipitation, filter and dry the precipitation to obtain a white solid, dissolve it in petroleum ethe/ethyl acetate and recrystallize to obtain 2.6 g white solid (90%). $^1$H-NMR (400M, CDCl$_3$) δ (ppm): 1.61 (s, 3H), 1.71 (s, 3H), 3.24 (d, J=6.8 Hz, 2H), 3.91 (s, 3H), 5.12 (t, J=6.8 Hz, 1H), 6.78 (s, 1H), 7.00 (d, J=16 Hz, 1H), 7.27 (t, J=7.2 Hz, 1H), 7.38 (t, J=7.2 Hz, 2H), 7.52 (d, J=7.2 Hz, 2H), 7.84 (d, J=16 Hz, 1H), 12.28 (s, 1H). ESI-MS mz: 361.14318 [M+Na]$^+$ (Calcd. for C$_{21}$H$_{22}$O$_4$Na: 361.14158).

Example 9

Preparation of methyl 2,4-dimethoxy-6-[(E)-4-fluorostyryl]-benzoate (6a)

Use 4-fluorobenzaldehyde as material and follow a method similar to what is described in Example 5 to obtain a white solid as the product (83%). $^1$H NMR (400 MHz, CDCl$_3$): 3.83 (s, 3H), 3.87 (s, 3H), 3.92 (s, 3H), 6.42 (s, 1H), 6.73 (s, 1H), 7.02 (m, 4H), 7.43 (m, 2H).

Example 10

Preparation of methyl 2-hydroxy-4-methoxy-6-[(E)-4-fluorostyryl]-benzoate (7a)

Use compound 6a as material, and follow the method described in Example 6 to obtain a white solid as the product (92%). $^1$H NMR (400 MHz, CDCl$_3$): 3.85 (s, 3H), 3.94 (s, 3H), 6.44 (s, 1H), 6.60 (s, 1H), 6.74 (d, J=16.0 Hz, 1H), 7.06 (t, J=8.4 Hz, 2H), 7.46 (m, 2H), 7.60 (d, J=16.0 Hz, 1H), 11.66 (m, 1H).

Example 11

Preparation of methyl 2-hydroxy-3-isopentenyl-4-methoxy-6-[(E)-4-fluorostyryl]-benzoate (8a)

Use compound 7a as material, and follow the method described in Example 7 to obtain a white solid as the product (63%). $^1$H NMR (400 MHz, CDCl$_3$): 1.68 (s, 3H), 1.79 (s, 3H), 3.37 (d, J=6.8 Hz, 2H), 3.92 (s, 3H), 3.93 (s, 3H), 51 (t, J=6.8 Hz, 1H), 6.44 (s, 1H), 638 (s, 1H), 6.73 (d, J=16.0 Hz, 1H), 7.06 (t, J=8.4 Hz, 2H), 7.46 (m, 2H), 7.63 (d, J=16.0 Hz, 1H), 11.65 (m, 1H).

Example 12

Preparation of 2-hydroxy-3-isopentenyl-4-methoxy-6-[(E)-4-fluorostyryl]benzoic acid (1a)

Use compound 8a as material, and follow the method described in Example 8 to obtain a white solid as the product (88%). $^1$H NMR (400 MHz, CDCl$_3$): 1.68 (s, 3H), 1.79 (s, 3H), 3.37 (d, J=7.2 Hz, 2H), 3.94 (s, 3H), 5.21 (t, J=7.2 Hz, 1H), 6.62 (s, 1H), 6.58 (s, 1H), 6.78 (d, J=16.0 Hz, 1H), 7.06 (t, J=8.4 Hz, 2H), 7.46 (m, 2H), 7.73 (d, J=16.0 Hz, 1H), 11.58 (m, 1H).

Example 13

Preparation of methyl 2,4-dimethoxy-6-[(E)-2-chlorostyryl]benzoate (6b)

Use 2-chlorobenzaldehyde as material, and follow the method similar to what is described in Example 5 to obtain a compound as a white solid (90%). $^1$H NMR (400 MHz, CDCl$_3$): 3.83 (s, 3H), 3.89 (s, 3H), 3.92 (s, 3H), 6.44 (s, 1H), 6.80 (s, 1H), 7.08 (d, J=16.0 Hz, 1H), 7.23 (m, 2H), 738 (d, J=7.6 Hz, 1H), 7.43 (d, J=16.0 Hz, 1H), 7.61 (d. J=7.6 Hz, 1H).

Example 14

Preparation of methyl 2-hydroxy-4-methoxy-6-[(E)-2-chlorostyryl]benzoate (7b)

Use compound 6b as material, and follow the method described in Example 6 to obtain a white solid as the product (95%). $^1$H NMR (400 MHz, CDCl$_3$): 3.86 (s, 3H), 3.95 (s, 3H), 6.46 (d, J=2.4 Hz, 1H), 6.67 (d, J=2.4 Hz, 1H), 7.18 (d, J=16.0 Hz, 1H), 78 (m, 2H), 7.40 (d, J=8.0 Hz, 1H), 7.64 (d. J=8.0 Hz, 1H), 7.67 (d, J=16.0 Hz, 1H), 11.66 (s, 1H).

Example 15

Preparation of methyl 2-hydroxy-3-isopentenyl-4-methoxy-6-[(E)-2-chlorostyryl]benzoate (8b)

Use compound 7b as material, and follow the method described in Example 7 to obtain a white solid as the product (58%). $^1$H NMR (400 MHz, CDCl$_3$): 1.68 (s, 3H), 1.79 (s, 3H), 3.38 (d, J=6.8 Hz, 2H), 3.93 (s, 3H), 5.22 (t, J=6.8 Hz, 1H), 6.64 (s, 1H), 7.15 (d, J=16.0 Hz, 1H), 7.28 (m, 2H), 7.40 (d, J=7.6 Hz, 1H), 7.64 (d. J=7.6 Hz, 1H), 7.69 (d, J=16.0 Hz, 1H), 11.66 (s, 1H).

Example 16

Preparation of 2-hydroxy-3-isopentenyl-4-methoxy-6-[(E)-2-chlorostyryl]benzoic acid (1b)

Use compound 8b as material, and follow the method described in Example 8 to obtain a white solid as the product (88%). $^1$H NMR (400 MHz, DMSO-$d_6$): 1.61 (s, 3H), 1.71 (s, 3H), 3.25 (d, J=7.2 Hz, 2H), 3.90 (s, 3H), 5.11 (t, J=7.2 Hz, 1H), 6.72 (s, 1H), 7.12 (d, J=16.0 Hz, 1H), 7.33 (m, 2H), 7.48 (d, J=7.6 Hz, 1H), 7.72 (d. J=7.6 Hz, 1H), 7.85 (d, J=16.0 Hz, 1H), 12.41 (s, 1H), 14.15 (br, 1H).

Example 17

Preparation of methyl 2,4-dimethoxy-6-[(E)-4-methoxystyryl]benzoate (6c)

Use p-methoxybenzaldehyde as material, and follow the method similar to what is described in Example 5 to obtain a white solid as the product (85%). $^1$H NMR (400 MHz, CDCl$_3$): 3.77 (s, 6H), 3.87 (s, 3H), 3.91 (s, 3H), 6.39 (s, 1H), 6.75 (s, 1H), 6.88 (d, J=16.0 Hz, 2H), 6.97 (d, J=16.0 Hz, 1H), 7.42 (d, J=8.4 Hz, 2H).

Example 18

Preparation of methyl 2-hydroxy-4-methoxy-6-[(E)-4-methoxy styryl]benzoate (7c)

Use compound 6c as material and follow the method described in Example 6 to obtain a white solid as the product (90%). $^1$H NMR (400 MHz, CDCl$_3$): 3.84 (s, 6H), 3.94 (s, 3H), 6.42 (d, J=2.4 Hz, 1H), 6.62 (d, J=2.4 Hz, 1H), 6.77 (d, J=16.0 Hz, 1H), 6.91 (d, J=8.8 Hz, 2H), 7.42 (d, J=8.8 Hz, 2H), 7.57 (d, J=16.0 Hz, 1H).

Example 19

Preparation of methyl 2-hydroxy-3-isopentenyl-4-methoxy-6-[(E)-4-methoxystyryl]-benzoate (8c)

Use compound 7c as material and follow the method described in Example 7 to obtain a white solid as the product (60%). $^1$H NMR (400 MHz, CDCl$_3$): 1.68 (s, 3H), 1.79 (s, 3H), 3.37 (d, J=6.8 Hz, 2H), 3.84 (s, 3H), 3.92 (s, 3H), 3.93 (s, 3H), 5.22 (t, J=6.8 Hz, 1H), 6.60 (s, 1H), 6.74 (d, J=16.0 Hz, 1H), 6.91 (d, J=8.4 Hz, 2H), 7.44 (d, J=8.4 Hz, 2H), 7.59 (d, J=16.0 Hz, 1H), 11.66 (s, 1H).

Example 20

Preparation of 2-hydroxy-3-isopentenyl-4-methoxy-6-[(E)-4-methoxystyryl]benzoic acid (1c)

Use compound 8c as material and follow the method described in Example 8 to obtain a white solid as the product (90%). $^1$H NMR (400 MHz, CDCl$_3$): 1.68 (s, 3H), 1.79 (s, 3H), 3.37 (d, J=6.8 Hz, 2H), 3.84 (s, 3H), 3.94 (s, 3H), 5.21 (t, J=6.8 Hz, 1H), 6.64 (s, 1H), 6.79 (d, J=16.0 Hz, 1H), 6.91 (d, J=8.4 Hz, 2H), 7.46 (d, J=8.4 Hz, 2H), 7.69 (d, J=16.0 Hz, 1H), 11.58 (s, 1H).

Example 21

Preparation of methyl 2,4-dimethoxy-6-[(E)-2,6-dimethoxystyryl]-benzoate (6d)

Use 2,6-dimethoxybenzaldehyde as a raw material, and follow a method similar to what is described in Example 5 to obtain a white solid as the product (78%). $^1$H NMR (400 MHz, CDCl$_3$): 3.82 (s, 3H), 3.83 (s, 9H), 3.90 (s, 3H), 637 (s, 1H), 637 (d, J=8.4 Hz, 2H), 6.84 (s, 1H), 7.17 (t, J=8.4 Hz, 1H), 7.39 (d, J=16.0 Hz, 1H), 7.58 (d, J=16.0 Hz, 1H).

Example 22

Preparation of methyl 2-hydroxy-4-methoxy-6-[(E)-2,6-dimethoxystyryl]benzoate (7d)

Use compound 6d as material and follow the method described in Example 6 to obtain a white solid as the product (86%). $^1$H NMR (400 MHz, CDCl$_3$): 3.85 (s, 3H), 3.89 (s, 6H), 3.92 (s, 3H), 6.41 (s, 1H), 6.60 (d, J=8.4 Hz, 2H), 6.71 (s, 1H), 7.18 (t, J=8.4 Hz, 1H), 7.19 (d, J=16.0 Hz, 1H), 8.15 (d, J=16.0 Hz, 1H), 11.68 (s, 1H).

Example 23

Preparation of methyl 2-hydroxy-3-isopentenyl-4-methoxy-6-[(E)-2,6-dimethoxystyryl]-benzoate (8d)

Use compound 7d as material and follow the method described in Example 7 to obtain a white solid (58%) as the product. $^1$H NMR (400 MHz, CDCl$_3$): 1.64 (s, 3H), 1.73 (s, 3H), 3.37 (d, J=7.2 Hz, 2H), 3.90 (s, 6H), 3.92 (s, 3H), 3.95 (s, 3H), 5.22 (t, J=7.2 Hz, 1H), 6.60 (d, J=8.4 Hz, 2H), 6.66 (s, 1H), 7.16 (m, 2H), 8.15 (d, J=16.0 Hz, 1H), 11.66 (s, 1H).

Example 24

Preparation of 2-hydroxy-3-isopentenyl-4-methoxy-6-[(E)-2,6-dimethoxystyryl]benzoic acid (1d)

Use compound 8d as material and follow the method described in Example 8 to obtain a white solid (92%) as the product. $^1$H NMR (400 MHz, DMSO-$d_6$): 1.60 (s, 3H), 1.71 (s, 3H), 3.23 (d, J=7.2 Hz, 2H), 3.80 (s, 6H), 3.87 (s, 3H), 5.11 (t, J=7.2 Hz, 1H), 6.62 (s, 1H), 6.67 (d, J=8.0 Hz, 2H), 6.98 (d, J=16.0 Hz, 1H), 7.20 (t, J=8.0 Hz, 1H) 8.15 (d, J=16.0 Hz, 1H), 12.39 (br, 1H), 13.85 (br, 1H).

Example 25

Preparation of methyl 2,4-dimethoxy-6-[(E)-2-methyl styryl]benzoate (6e)

Use 2-methyl-benzaldehyde as material and follow the method similar to what is described in Example 5 to obtain a white solid (88%) as the product. $^1$H NMR (400 MHz, CDCl$_3$): 2.41 (s, 3H), 3.83 (s, 3H), 3.88 (s, 3H), 3.91 (s, 3H), 6.42 (d, J=2.4 Hz, 1H), 6.76 (d, J=2.4 Hz, 1H), 6.97 (d, J=16.0 Hz, 1H), 70 (m, 3H), 7.24 (d, J=16.0 Hz, 1H), 731 (d, J=8.0 Hz, 1H).

Example 26

Preparation of methyl 2-hydroxy-4-methoxy-6-[(E)-2-methyl styryl]benzoate (7e)

Use compound 6e as material and follow the method described in Example 6 to obtain a white solid as the product (87%). ¹H NMR (400 MHz, CDCl₃): 2.42 (s, 3H), 3.86 (s, 3H), 3.88 (s, 3H), 3.95 (s, 3H), 6.45 (d, J=2.4 Hz, 1H), 6.63 (d, J=2.4 Hz, 1H), 7.01 (d, J=15.6 Hz, 1H), 7.20 (m, 3H), 7.56 (d, J=6.4 Hz, 1H), 7.58 (d, J=16.0 Hz, 1H), 11.71 (s, 1H).

Example 27

Preparation of methyl 2-hydroxy-3-isopentenyl-4-methoxy-6-[(E)-2-methylstyryl]-benzoate (8e)

Use compound 7e as material and follow the method described in Example 7 to obtain a white solid as the product (59%). ¹H NMR (400 MHz, CDCl₃): 1.68 (s, 3H), 1.79 (s, 3H), 2.42 (s, 3H), 3.38 (d, J=7.2 Hz, 2H), 3.93 (s, 6H), 5.22 (t, J=7.2 Hz, 1H), 6.60 (s, 1H), 6.96 (d, J=16.0 Hz, 1H), 7.20 (m, 3H), 7.56 (d, J=6.8 Hz, 1H), 7.60 (d, J=16.0 Hz, 1H), 11.69 (s, 1H).

Example 28

Preparation of 2-hydroxy-3-isopentenyl-4-methoxy-6-[(E)-2-methylstyryl]benzoic acid (1e)

Use compound 8e as material and follow the method described in Example 8 to obtain a white solid as the product (89%). ¹H NMR (400 MHz, CDCl₃): 1.68 (s, 3H), 1.79 (s, 3H), 2.42 (s, 3H), 3.38 (d, J=7.2 Hz, 2H), 3.95 (s, 3H), 5.21 (t, J=7.2 Hz, 1H), 6.64 (s, 1H), 7.01 (d, J=15.6 Hz, 1H), 7.20 (m, 3H), 7.59 (d, J=7.2 Hz, 1H), 7.70 (d, J=15.6 Hz, 1H), 11.54 (s, 1H).

Example 29

Preparation of methyl 2,4-dimethoxy-6-[(E)-3-methylstyryl]benzoate (6f)

Use 3-methyl benzaldehyde as material and follow the method similar to what is described in Example 5 to obtain a white solid as the product (82%). ¹H NMR (400 MHz, CDCl₃): 236 (s, 3H), 3.82 (s, 3H), 3.87 (s, 3H), 3.92 (s, 3H), 6.40 (s, 1H), 6.76 (s, 1H), 7.06 (m, 3H), 7.24 (m, 2H), 7.28 (s, 1H).

Example 30

Preparation of methyl 2-hydroxy-4-methoxy-6-[(E)-3-methylstyryl]benzoate (7f)

Use compound 6f as material and follow the method described in Example 6 to obtain a white solid as the product (87%). ¹H NMR (400 MHz, CDCl₃): 2.38 (s, 3H), 3.85 (s, 3H), 3.93 (s, 3H), 6.43 (d, J=2.0 Hz, 1H), 6.76 (d, J=2.0 Hz, 1H), 6.77 (d, J=16.0 Hz, 2H), 7.10 (d, J=7.2 Hz, 1H), 7.29 (m, 3H), 7.67 (d, J=16.0 Hz, 2H), 11.67 (s, 1H).

Example 31

Preparation of methyl 2-hydroxy-3-isopentenyl-4-methoxy-6-[(E)-3-methylstyryl]-benzoate (8f)

Use compound 7f as material and follow the method described in Example 7 to obtain a white solid as the product (58%). ¹H NMR (400 MHz, CDCl₃) 1.68 (s, 3H), 1.79 (s, 3H), 2.38 (s, 3H), 3.37 (d, J=7.2 Hz, 2H), 3.92 (s, 3H), 3.94 (s, 3H), 5.21 (t, J=7.2 Hz, 1H), 6.60 (s, 1H), 6.75 (d, J=16.0 Hz, 1H), 7.10 (d, J=6.8 Hz, 1H), 730 (m, 3H), 7.70 (d, J=16.0 Hz, 1H), 11.67 (s, 1H).

Example 32

Preparation of 2-hydroxy-3-isopentenyl-4-methoxy-6-[(E)-3-methylstyryl]benzoic acid (1f)

Use compound 8f as material and follow the method described in Example 8 to obtain a white solid as the product (89%). ¹H NMR (400 MHz, CDCl₃): 1.68 (s, 3H), 1.79 (s, 3H), 2.38 (s, 3H), 3.37 (d, J=6.8 Hz, 2H), 3.94 (s, 3H), 5.20 (t, J=6.8 Hz, 1H), 6.64 (s, 1H), 6.80 (d, J=15.6 Hz, 1H), 7.10 (d, J=7.2 Hz, 1H), 78 (m, 2H), 7.32 (s, 1H), 7.80 (d, J=15.6 Hz, 1H), 11.55 (s, 1H).

Example 33

Preparation of methyl 2,4-dimethoxy-6-[(E)-4-methylstyryl]-benzoate (6g)

Use 4-methyl benzaldehyde as material, and follow the method similar to what is described in Example 5 to obtain a white solid as the product (80%). ¹H NMR (400 MHz, CDCl₃): 236 (s, 3H), 3.82 (s, 3H), 3.88 (s, 3H), 3.92 (s, 3H), 6.40 (s, 1H), 6.76 (s, 1H), 7.02 (dd, J=16.0 Hz, 2H), 7.15 (d, J=8.0 Hz, 2H), 7.37 (d, J=8.0 Hz, 2H).

Example 34

Preparation of methyl 2-hydroxy-4-methoxy-6-[(E)-4-methyl styryl]benzoate (7g)

Use compound 6 g as material, and follow the method described in Example 6 to obtain a white solid as the product (89%). ¹H NMR (400 MHz, CDCl₃): 2.38 (s, 3H), 3.85 (s, 3H), 3.94 (s, 3H), 6.43 (s, 1H), 6.63 (s, 1H), 6.78 (d, J=16.0 Hz, 1H), 7.18 (d, J=8.0 Hz, 2H), 7.39 (d, J=8.0 Hz, 2H), 7.65 (d, J=16.0 Hz, 1H), 11.68 (s, 1H).

Example 35

Preparation of methyl 2-hydroxy-3-isopentenyl-4-methoxy-6-[(E)-4-methylstyryl]benzoate (8g)

Use compound 7 g as material, and follow the method described in Example 7 to obtain a white solid as the product (65%). ¹H NMR (400 MHz, CDCl₃): 1.68 (s, 3H), 1.79 (s, 3H), 2.37 (s, 3H), 3.37 (d, J=7.2 Hz, 2H), 3.92 (s, 6H), 5.22 (t, J=7.2 Hz, 1H), 6.60 (s, 1H), 6.76 (d, J=16.0 Hz, 1H), 7.18 (d, J=8.0 Hz, 2H), 7.40 (d, J=8.0 Hz, 2H), 7.67 (d, J=16.0 Hz, 1H), 11.67 (s, 1H).

Example 36

Preparation of 2-hydroxy-3-isopentenyl-4-methoxy-6-[(E)-4-methylstyryl]benzoic acid (1g)

Use compound 8 g as material and follow the method described in Example 8 to obtain a white solid as the product (93%). ¹H NMR (400 MHz, DMSO-d₆): 1.60 (s, 3H), 1.71 (s, 3H), 2.30 (s, 3H), 3.23 (d, J=7.2 Hz, 2H), 3.90 (s, 3H), 5.11 (t, J=7.2 Hz, 1H), 6.76 (s, 1H), 6.96 (d, J=16.0 Hz, 1H), 7.18 (d, J=8.4 Hz, 2H), 7.41 (d, J=8.4 Hz, 2H), 7.79 (d, J=16.0 Hz, 1H), 12.29 (br, 1H), 13.97 (br, 1H).

Example 37

Preparation of methyl 2,4-dimethoxy-6-[(E)-buten-1-yl]-benzoate (6h)

Use propionaldehyde as material, and follow the method similar to what is described in Example 5 to obtain a colorless oily liquid as the product (88%). ¹H NMR (400 MHz, CDCl₃): 1.06 (t, J=7.2 Hz, 3H), 2.20 (m, 2H), 3.81 (s, 3H), 3.82 (s, 3H), 3.88 (s, 3H), 6.21 (m, 1H), 6.34 (d, J=16.0 Hz, 1H), 6.35 (d, J=2.0 Hz, 1H), 6.59 (d, J=2.0 Hz, 1H).

Example 38

Preparation of methyl 2-hydroxy-4-methoxy-6-[(E)-buten-1-yl]-benzoate (7h)

Use Compound 6h as material, and follow the method described in Example 6 to obtain a white solid as the product (89%). ¹H NMR (400 MHz, CDCl₃): 1.10 (t, J=7.2 Hz, 3H), 2.22 (m, 2H), 3.83 (s, 3H), 3.91 (s, 3H), 5.97 (m, 1H), 6.37 (d, J=2.4 Hz, 1H), 6.46 (d, J=2.4 Hz, 1H), 6.91 (d, J=16.0 Hz, 1H), 11.62 (s, 1H).

Example 39

Preparation of methyl 2-hydroxy-3-isopentenyl-4-methoxy-6-[(E)-buten-1-yl]-benzoate (8h)

Use Compound 7h as material, and follow the method described in Example 7 to obtain a white solid as the product (67%). ¹H NMR (400 MHz, CDCl₃): 1.11 (t, J=7.2 Hz, 3H), 1.67 (s, 3H), 1.78 (s, 3H), 2.22 (m, 2H), 3.34 (d, J=7.2 Hz, 2H), 3.88 (s, 3H), 3.91 (s, 3H), 5.19 (t, J=7.2 Hz, 1H), 5.97 (m, 1H), 6.45 (s, 1H), 6.93 (d, J=16.0 Hz, 1H), 11.60 (s, 1H).

Example 40

Preparation of 2-hydroxy-3-isopentenyl-4-methoxy-6-[(E)-buten-1-yl]benzoic acid (1h)

Use Compound 8h as material, and follow the method described in Example 8 to obtain a white solid as the product (86%). ¹H NMR (400 MHz, CDCl₃): 1.12 (t, J=7.2 Hz, 3H), 1.67 (s, 3H), 1.78 (s, 3H), 2.26 (m, 2H), 3.34 (d, J=6.8 Hz, 2H), 3.90 (s, 3H), 5.20 (t, J=6.8 Hz, 1H), 6.01 (m, 1H), 6.48 (s, 1H), 7.05 (d, J=15.6 Hz, 1H), 10.38 (br, 1H), 11.53 (s, 1H).

Example 41

Preparation of methyl 2,4-dimethoxy-6-[(E)-2-phenylpropen-1-yl]-benzoate (6i)

Use benzophenone as material, and follow the method similar to what is described in Example 5 to obtain a white solid as the product (84%). ¹H NMR (400 MHz, CDCl₃): 2.19 (s, 3H), 3.31 (s, 3H), 3.76 (s, 3H), 3.90 (s, 3H), 5.84 (d, J=1.6 Hz, 1H), 6.20 (d, J=1.6 Hz, 1H), 6.47 (s, 1H), 7.20 (m, 5H).

Example 42

Preparation of methyl 2-hydroxy-4-methoxy-6-[(E)-2-phenylpropen-1-yl]-benzoate (7i)

Use Compound 6i as material, and follow the method described in Example 6 to obtain a white solid as the product (91%). ¹H NMR (400 MHz, CDCl₃): 2.19 (s, 3H), 3.49 (s, 3H), 3.94 (s, 3H), 5.88 (d, J=1.6 Hz, 1H), 6.23 (d, J=1.6 Hz, 1H), 6.73 (s, 1H), 7.12 (m, 5H), 11.60 (s, 1H).

Example 43

Preparation of methyl 2-hydroxy-3-isopentenyl-4-methoxy-6-[(E)-2-phenylpropen-1-yl]-benzoate (8i)

Use Compound 7i as material, and follow the method described in Example 7 to obtain a white solid as the product (63%). ¹H NMR (400 MHz, CDCl₃): 1.65 (s, 3H), 1.73 (s, 3H), 2.22 (s, 3H), 3.24 (d, J=7.2 Hz), 3.94 (s, 3H), 5.12 (t, J=7.2 Hz, 1H), 5.86 (s, 1H), 6.77 (s, 1H), 7.14 (m, 5H), 11.60 (s, 1H).

Example 44

Preparation of 2-hydroxy-3-isopentenyl-4-methoxy-6-[(E)-2-phenylpropen-1-yl]benzoic acid (1i)

Use Compound 8i as material, and follow the method described in Example 8 to obtain a white solid as the product (93%). ¹H NMR (400 MHz, CDCl₃): 1.65 (s, 3H), 1.73 (s, 3H), 2.26 (s, 3H), 3.25 (d, J=7.2 Hz), 3.33 (s, 3H), 5.12 (t, J=7.2 Hz, 1H), 5.90 (s, 1H), 6.86 (s, 1H), 7.16 (m, 5H), 11.57 (s, 1H).

Example 45

Preparation of methyl 2,4-dimethoxy-6-[(E)-2-(thien-2-yl)ethenyl]benzoate (6j)

Use 2-thenaldehyde as material, and follow the method similar to what is described in Example 5 to obtain a white solid as the product (83%). ¹H NMR (400 MHz, CDCl₃): 3.82 (s, 3H), 3.84 (s, 3H), 3.86 (s, 3H), 6.40 (s, 1H), 6.70 (s, 1H), 6.90 (d, J=15.6 Hz, 1H), 6.99 (t, J=4.0 Hz, 1H), 7.07 (d, J=4.0 Hz, 1H), 7.14 (d, J=4.0 Hz, 1H), 7.24 (d, J=15.6 Hz, 1H).

Example 46

Preparation of methyl 2-hydroxy-4-methoxy-6-[(E)-2-(thien-2-yl)ethenyl]benzoate (7j)

Use Compound 6j as material, and follow the method described in Example 6 to obtain a white solid as the product (78%). ¹H NMR (400 MHz, CDCl₃): 3.84 (s, 3H), 3.96 (s, 3H), 6.43 (s, 1H), 6.60 (s, 1H), 6.95 (d, J=15.6 Hz, 1H), 7.01 (d, J=4.4 Hz, 1H), 7.06 (t, J=4.4 Hz, 1H) 7.21 (d, J=4.4 Hz, 1H), 7.55 (d, J=15.6 Hz, 1H), 11.68 (s, 1H).

Example 47

Preparation of methyl 2-hydroxy-3-isopentenyl-4-methoxy-6-[(E)-2-(thien-2-yl)ethenyl]benzoate (8j)

Use Compound 7j as material, and follow the method described in Example 7 to obtain a white solid as the product (60%). ¹H NMR (400 MHz, DMSO-d₆): 1.68 (s, 3H), 1.78 (s, 3H), 3.36 (d, J=7.2 Hz, 2H), 3.91 (s, 3H), 3.95 (s, 3H), 5.21 (t, J=7.2 Hz, 1H), 638 (s, 1H), 6.92 (d, J=16.0 Hz, 1H), 7.01 (t, J=4.0 Hz, 1H), 7.06 (d, J=4.0 Hz, 1H), 7.20 (d, J=4.0 Hz, 1H), 7.57 (d, J=16.0 Hz, 1H), 11.67 (s, 1H).

Example 48

Preparation of 2-hydroxy-3-isopentenyl-4-methoxy-6-[(E)-2-(thien-2-yl)ethenyl]benzoic acid (1j)

Use Compound 8j as material, and follow the method described in Example 8 to obtain a white solid as the product (89%). ¹H NMR (400 MHz, DMSO-d₆): 1.61 (s, 3H), 1.72 (s, 3H), 3.24 (d, J=7.2 Hz, 2H), 3.91 (s, 3H), 5.11 (t, J=7.2 Hz, 1H), 6.79 (s, 1H), 7.06 (dd, J1=3.2 Hz, J2=4.0 Hz, 1H), 7.18 (d, J=3.2 Hz, 1H), 7.26 (d, J=15.6 Hz, 1H), 7.46 (d, J=4.0 Hz, 1H), 7.67 (d, J=15.6 Hz, 1H), 12.30 (br, 1H), 14.10 (br, 1H).

Example 49

Preparation of methyl 2,4-dimethoxy-6-[(E)-3-phenyl-propen-1'-yl]-benzoate (6k)

Use benzaldehyde as material, and follow the method similar to what is described in Example 5 to obtain a colorless oily liquid as the product (78%). $^1$H NMR (400 MHz, CDCl$_3$): 3.49 (d, J=6.4 Hz, 2H), 3.71 (s, 3H), 3.74 (s, 3H), 3.78 (s, 3H), 6.19 (d, J=16.0 Hz, 1H), 6.47 (m, 1H), 6.50 (d, J=2.4 Hz, 1H), 6.71 (d, J=2.4 Hz, 1H), 70 (m, 3H), 7.31 (t, J=8.0 Hz, 2H).

Example 50

Preparation of methyl 2-hydroxy-4-methoxy-6-[(E)-3'-phenylpropen-1'-yl]benzoate (7k)

Use compound 6k as material, and follow the method described in Example 6 to obtain a colorless oily liquid as the product (87%). $^1$H NMR (400 MHz, CDCl$_3$): 3.52 (d, J=6.4 Hz, 2H), 3.80 (s, 3H), 3.86 (s, 3H), 6.08 (m, 1H), 6.38 (s, 1H), 6.48 (s, 1H), 6.88 (d, J=16.0 Hz, 1H), 7.32 (m, 5H), 11.72 (s, 1H).

Example 51

Preparation of methyl 2-hydroxy-3-isopentenyl-4-methoxy-6-[(E)-3'-phenyl-propen-1'-yl]benzoate (8k)

Use compound 7k as material, and follow the method described in Example 7 to obtain a pale yellow oily liquid as the product. Since this product is difficult to purify (with a small amount of impurities), no NMR characterization was performed. It can be used directly in the next step.

Example 52

Preparation of 2-hydroxy-3-isopentenyl-4-methoxy-6-[(E)-3'-phenyl-propen-1'-yl]benzoic acid (1k)

Use Compound 8k as material, and follow the method described in Example 8 to obtain a white solid as the product (91%). $^1$H NMR (400 MHz, CDCl$_3$): 1.67 (s, 3H), 1.78 (s, 3H), 3.34 (d, J=7.2 Hz, 2H), 3.57 (d, J=6.8 Hz, 2H), 5.19 (t, J=6.8 Hz, 1H), 6.10 (m, 1H), 6.49 (s, 1H), 7.12 (d, J=16.0 Hz, 1H), 7.20 (m, 3H), 7.31 (t, J=8.0 Hz, 2H), 11.52 (s, 1H).

Example 53

Preparation of methyl 2,4-dimethoxy-6-[(E)-4'-phenylbuten-1'-yl]benzoate (6l)

Use phenylpropyl aldehyde as material, and follow the method similar to what is described in Example 5 to obtain a white solid as the product (80%). $^1$H NMR (400 MHz, CDCl$_3$): 2.50 (q, J=7.2 Hz, 2H), 2.78 (t, J=7.2 Hz, 2H), 3.80 (s, 6H), 3.82 (s, 3H), 6.22 (m, 1H), 6.34 (d, J=2.0 Hz, 1H), 6.43 (d, J=15.6 Hz, 1H), 6.57 (d, J=2.0 Hz, 1H), 7.21 (m, 5H).

Example 54

Preparation of methyl 2-hydroxy-4-methoxy-6-[(E)-4'-phenylbuten-1'-yl]benzoate (7l)

Use Compound 8l as material, and follow the method described in Example 6 to obtain a white solid as the product (86%). $^1$H NMR (400 MHz, CDCl$_3$): 2.50 (q, J=7.2 Hz, 2H), 2.80 (t, J=7.2 Hz, 2H), 3.80 (s, 6H), 5.92 (m, 1H), 6.37 (d, J=2.0 Hz, 1H), 6.43 (d, J=2.0 Hz, 1H), 6.99 (d, J=15.6 Hz, 1H), 7.25 (m, 5H), 11.69 (s, 1H).

Example 55

Preparation of methyl 2-hydroxy-3-isopentenyl-4-methoxy-6-[(E)-4'-phenylbuten-1'-yl]benzoate (8l)

Use Compound 7l as material, and follow the method described in Example 7 to obtain a white solid as the product (63%). $^1$H NMR (400 MHz, CDCl$_3$): 1.66 (s, 3H), 1.79 (s, 3H), 2.52 (q, J=7.6 Hz, 2H), 2.82 (t, J=7.6 Hz, 2H), 3.34 (d, J=6.8 Hz, 2H), 3.87 (s, 6H), 5.20 (t, J=6.8 Hz, 1H), 5.89 (m, 1H), 6.40 (s, 1H), 7.01 (d, J=15.6 Hz, 1H), 7.25 (m, 5H), 11.69 (s, 1H).

Example 56

Preparation of 2-hydroxy-3-isopentenyl-4-methoxy-6-[(E)-4'-phenylbuten-1'-yl]benzoic acid (1l)

Use Compound 8l as material, and follow the method described in Example 8 to obtain a white solid as the product (86%). $^1$H NMR (400 MHz, CDCl$_3$): 1.66 (s, 3H), 1.78 (s, 3H), 2.56 (q, J=7.6 Hz, 2H), 2.82 (t, J=7.6 Hz, 2H), 3.34 (d, J=6.8 Hz, 2H), 3.84 (s, 3H), 5.20 (t, J=6.8 Hz, 1H), 5.95 (m, 1H), 6.42 (s, 1H), 7.03 (d, J=15.6 Hz, 1H), 7.25 (m, 5H), 11.54 (s, 1H).

Example 57

Preparation of methyl 2,4-dimethoxy-6-[(1'E,3'E)-1',3'-phenyl butadiene-yl]benzoate (6m)

Use cinnamic aldehyde as material, and follow the method similar to what is described in Example 5 to obtain a pale yellow oily liquid as the product (82%). $^1$H NMR (400 MHz, DMSO-d$_6$): 3.76 (s, 3H), 3.80 (s, 3H), 3.86 (s, 3H), 633 (d, J=2.0 Hz, 1H), 634 (d, J=15.2 Hz, 1H), 6.78 (d, J=15.2 Hz, 1H), 6.87 (d, J=2.0 Hz, 1H), 7.13 (m, 2H), 7.26 (t, J=7.6 Hz, 1H), 7.34 (t, J=7.6 Hz, 2H), 7.52 (d, J=7.6 Hz, 2H).

Example 58

Preparation of methyl 2-hydroxy-4-methoxy-6-[(1'E,3'E)-phenyl butadien-1',3'-yl]benzoate (7m)

Use Compound 8m as material, and follow the method described in Example 6 to obtain a pale yellow oily liquid as the product. Since the purification of the product is difficult, no NMR characterization was performed.

Example 59

Preparation of methyl 2-hydroxy-3-isopentenyl-4-methoxy-6-[(1'E,3'E)-phenylbutadien-1',3'-yl]benzoate (8m)

Use Compound 7m as material, and follow the method described in Example 7 to obtain a pale yellow solid as the product (63%). $^1$H NMR (400 MHz, DMSO-d$_6$): 1.60 (s, 3H), 1.70 (s, 3H), 3.24 (d, J=6.8 Hz, 2H), 3.87 (s, 3H), 3.88 (s, 3H), 5.09 (t, J=6.8 Hz, 1H), 6.76 (d, J=15.2 Hz, 1H), 6.80 (d, J=15.2 Hz, 1H), 7.06 (m, 3H), 7.24 (t, J=7.6 Hz, 1H), 7.35 (t, J=7.6 Hz, 2H), 7.51 (d, J=7.6 Hz, 2H), 10.44 (s, 1H).

Example 60

Preparation of 2-hydroxy-3-isopentenyl-4-methoxy-6-[(1'E,3'E)-phenyl butadien-1',3'-yl]benzoic acid (1m)

Use Compound 8m as material, and follow the method described in Example 8 to obtain a pale yellow solid as the product (90%). $^1$H NMR (400 MHz, DMSO-d$_6$): 1.60 (s, 3H), 1.70 (s, 3H), 3.23 (d, J=7.2 Hz, 2H), 3.89 (s, 3H), 5.10 (t, J=7.2 Hz, 1H), 6.74 (d, J=15.6 Hz, 1H), 6.76 (s, 1H), 6.92 (dd, J1=15.2 Hz, J2=15.2 Hz, 1H), 7.10 (dd, J1=15.6 Hz, J2=15.2 Hz, 1H), 7.24 (t, J=7.6 Hz, 1H), 7.34 (t, J=7.6 Hz, 2H), 7.45 (d, J=15.2 Hz, 1H), 7.51 (d, J=7.6 Hz, 2H), 12.24 (br, 1H), 14.05 (br, 1H).

Example 61

Preparation of methyl 2,4-dimethoxy-6-(4'-methyl-cyclohexylene-methyl)benzoate (6n)

Use 4-methylcyclohexanone as material, and follow the method similar to what is described in Example 5 to obtain a white solid as the product (85%). $^1$H NMR (400 MHz, CDCl$_3$): 0.90 (d, J=6.4 Hz, 3H), 1.05 (m, 2H), 1.55 (m, 1H), 1.80 (m, 3H), 2.17 (m, 1H), 2.29 (d, J=13.2 Hz, 1H), 2.53 (d, J=13.2 Hz, 1H), 3.80 (s, 6H), 3.82 (s, 3H), 6.15 (s, 1H), 6.28 (s, 1H), 6.35 (s, 1H).

Example 62

Preparation of methyl 2-hydroxy-4-methoxy-6-(4'-methyl-cyclohexylidene-ylmethyl)benzoate (7n)

Use Compound 6n as material, and follow the method described in Example 6 to obtain a colorless oily liquid as the product (86%). $^1$H NMR (400 MHz, CDCl$_3$): 0.88 (m, 2H), 0.91 (d, J=6.4 Hz, 3H), 1.58 (m, 1H), 1.78 (m, 3H), 2.18 (m, 1H), 2.33 (d, J=13.2 Hz, 1H), 2.49 (d, J=13.2 Hz, 1H), 3.80 (s, 3H), 3.86 (s, 3H), 6.21 (s, 1H), 6.36 (s, 2H).

Example 63

Preparation of methyl 2-hydroxy-3-isopentenyl-4-methoxy-6-(4'-methyl-cyclohexylenemethyl)benzoate (8n)

Use Compound 7n as material, and follow the method described in Example 7 to obtain a colorless oily liquid as the product (54%). $^1$H NMR (400 MHz, CDCl$_3$): 0.88 (d, J=6.4 Hz, 3H), 0.94 (m, 1H), 1.10 (m, 1H), 1.59 (m, 1H), 1.67 (s, 3H), 1.78 (s, 3H), 1.83 (m, 3H), 2.20 (m, 1H), 2.34 (d, J=13.2 Hz, 1H), 2.50 (d, J=13.2 Hz, 1H), 3.34 (d, J=6.8 Hz, 2H), 3.83 (s, 1H), 3.85 (s, 3H), 5.22 (t, J=6.8 Hz, 1H), 6.20 (s, 1H), 6.39 (s, 1H), 11.65 (s, 1H).

Example 64

Preparation of 2-hydroxy-3-isopentenyl-4-methoxy-6-(4'-methyl-cyclohexylenemethyl)benzoic acid (1n)

Use Compound 8n as material, and follow the method described in Example 8 to obtain a white solid as the product (94%). $^1$H NMR (400 MHz, CDCl$_3$): 0.93 (d, J=6.4 Hz, 3H), 0.94 (m, 1H), 1.10 (m, 1H), 1.59 (m, 1H), 1.68 (s, 3H), 1.78 (s, 3H), 1.83 (m, 3H), 2.20 (m, 1H), 2.45 (d, J=13.2 Hz, 2H), 3.35 (d, J=6.8 Hz, 2H), 3.85 (s, 3H), 5.21 (t, J=6.8 Hz, 1H), 6.16 (s, 1H), 6.47 (s, 1H), 12.10 (s, 1H). EI/MS: m/z 344.1963 Calcul for C21H28O4 344.1988.

Example 65

Preparation of methyl 2-hydroxy-3-(3',7'-dimethyl octadien-2',6'-yl)-4-methoxy-6-[(E)-styryl]benzoate (8o)

Use Compound 7 and 3',7'-dimethyl octadien-2',6'-yl bromide as materials, and follow the method described in Example 7 to obtain a pale yellow oily liquid (60%) as the product. $^1$H NMR (400 MHz, CDCl$_3$): 1.57 (s, 3H), 1.64 (s, 3H), 1.78 (s, 3H), 2.03 (m, 4H), 3.78 (d, J=6.8 Hz, 2H), 3.91 (s, 3H), 3.92 (s, 3H), 5.07 (t, J=6.8 Hz, 1H), 5.22 (t, J=6.8 Hz, 1H), 6.61 (s, 1H), 6.78 (d, J=16.0 Hz, 1H), 7.28 (t, J=7.6 Hz, 1H), 7.37 (t, J=7.6 Hz, 2H), 730 (d, J=7.6 Hz, 2H), 7.72 (d, J=16.0 Hz, 1H), 11.66 (s, 1H).

Example 66

Preparation of methyl 2-hydroxy-3-(3',7'-dimethyl octadien-2',6'-yl)-4-methoxy-6-[(E)-styryl]benzoate (1o)

Use Compound 8o as material, and follow the method described in Example 8 to obtain a white solid as the product (89%). $^1$H NMR (400 MHz, CDCl$_3$): 1.56 (s, 3H), 1.64 (s, 3H), 1.79 (s, 3H), 2.03 (m, 4H), 3.27 (d, J=6.4 Hz, 2H), 3.88 (s, 3H), 5.07 (t, J=6.4 Hz, 1H), 5.18 (t, J=6.8 Hz, 1H), 6.42 (s, 1H), 6.66 (d, J=16.0 Hz, 1H), 7.24 (t, J=7.6 Hz, 1H), 7.29 (t, J=7.6 Hz, 2H), 7.41 (d, J=7.6 Hz, 2H), 7.77 (d, J=16.0 Hz, 1H).

Example 67

Preparation of methyl 2,4-dimethoxy-6-[(E)-2-cyclohexyl-vinyl]benzoate (6p)

Use cyclohexylformaldehyde as material, follow the method described in Example 5 to obtain a colorless oily liquid as the product (84%). $^1$H NMR (400 MHz, CDCl$_3$): 1.39 (m, 5H), 1.60 (m, 5H), 2.20 (m, 1H), 3.80 (s, 6H), 3.90 (s, 3H), 6.03 (d, J=16.0 Hz, 1H), 6.48 (s, 1H), 6.70 (s, 1H), 6.98 (d, J=16.0 Hz, 1H).

Example 68

Preparation of methyl 2-hydroxy-4-methoxy-6-[(E)-2-cyclohexyl-vinyl]benzoate (7p)

Use Compound 6p as material, and follow the method similar to what is described in Example 6 to obtain a colorless oily liquid as the product (89%). $^1$H NMR (400 MHz, CDCl$_3$): 1.40 (m, 5H), 1.62 (m, 5H), 2.19 (m, 1H), 3.80 (s, 3H), 3.90 (s, 3H), 6.08 (d, J=16.0 Hz, 1H), 6.46 (s, 1H), 6.75 (s, 1H), 6.97 (d, J=16.0 Hz, 1H), 11.66 (s, 1H).

Example 69

Preparation of methyl 2-hydroxy-3-isopentenyl-4-methoxy-6-[(E)-2-cyclohexyl-vinyl]benzoate (8p)

Use Compound 7p as material, and follow the method similar to what is described in Example 7 to obtain a colorless oily liquid as the product (59%). ¹H NMR (400 MHz, CDCl₃): 1.35 (m, 5H), 1.59 (m, 5H), 1.68 (s, 3H), 1.79 (s, 3H), 2.19 (m, 1H), 3.35 (d, J=7.2 Hz, 2H), 3.80 (s, 3H), 3.88 (s, 3H), 5.21 (t, J=7.2 Hz, 1H), 6.60 (s, 1H), 6.75 (d, J=16.0 Hz, 1H), 7.30 (d, J=16.0 Hz, 1H), 11.78 (s, 1H).

Example 70

Preparation of 2-hydroxy-3-isopentenyl-4-methoxy-6-[(E)-2-cyclohexyl-vinyl]benzoic acid (1p)

Use Compound 8p as material, and follow the method similar to what is described in Example 8 to obtain a white solid as the product (92%). ¹H NMR (400 MHz, DMSO-d₆): 1.34 (m, 5H), 1.57 (m, 5H), 1.67 (s, 3H), 1.77 (s, 3H), 2.21 (m, 1H), 338 (d, J=7.2 Hz, 2H), 3.85 (s, 3H), 5.21 (t, J=7.2 Hz, 1H), 6.63 (s, 1H), 6.74 (d, J=16.0 Hz, 1H), 7.23 (d, J=16.0 Hz, 1H), 11.78 (s, 1H), 12.30 (br, 1H).

Example 71

Preparation of methyl 2,4-dimethoxy-6-[(E)-4'-acetoxystyryl]benzoate (6q)

Use acetoxy benzaldehyde as material, and follow the method similar to what is described in Example 5 to obtain a white solid as the product (84%). ¹H NMR (400 MHz, CDCl₃): 2.31 (s, 3H), 3.73 (s, 3H), 3.77 (s, 3H), 3.88 (s, 3H), 631 (s, 1H), 6.66 (s, 1H), 6.82 (d, J=16.0 Hz, 1H), 7.07 (d, J=8.0 Hz, 2H), 730 (d, J=16.0 Hz, 1H), 7.41 (d, J=8.0 Hz, 2H).

Example 72

Preparation of methyl 2-hydroxy-4'-methoxy-6-[(E)-4-acetoxystyryl]benzoate (7q)

Use Compound 6q as material, and follow the method similar to what is described in described in Example 6 to obtain a white solid as the product (87%). ¹H NMR (400 MHz, CDCl₃): 2.30 (s, 3H), 3.78 (s, 3H), 3.90 (s, 3H), 6.54 (s, 1H), 6.70 (s, 1H), 6.84 (d, J=16.0 Hz, 1H), 7.08 (d, J=8.0 Hz, 2H), 7.31 (d, J=16.0 Hz, 1H), 7.43 (d, J=8.0 Hz, 2H), 11.65 (s, 1H).

Example 73

Preparation of methyl 2-hydroxy-3-isopentenyl-4'-methoxy-6-[(E)-4-acetoxystyryl]benzoate (8q)

Use Compound 7q as material, and follow the method similar to what is described in described in Example 7 to obtain a white solid as the product (65%). ¹H NMR (400 MHz, CDCl₃): 1.65 (s, 3H), 1.78 (s, 3H), 2.33 (s, 3H), 3.22 (d, J=7.2 Hz, 2H), 3.73 (s, 3H), 3.89 (s, 3H), 5.21 (t, J=7.2 Hz, 1H), 6.48 (s, 1H), 6.83 (d, J=16.0 Hz, 1H), 7.05 (d, J=8.0 Hz, 2H), 7.30 (d, J=16.0 Hz, 1H), 7.39 (d, J=8.0 Hz, 2H), 11.56 (s, 1H).

Example 74

Preparation of methyl 2-hydroxy-3-isopentenyl-4'-methoxy-6-[(E)-4-hydroxystyryl]benzoate (1q)

Use Compound 8q as material, and follow the method similar to what is described in Example 8 to obtain a white solid as the product (89%). ¹H NMR (400 MHz, DMSO-d₆): 1.64 (s, 3H), 1.74 (s, 3H), 3.21 (d, J=7.2 Hz, 2H), 3.89 (s, 3H), 5.21 (t, J=7.2 Hz, 1H), 6.46 (s, 1H), 6.84 (d, J=16.0 Hz, 1H), 7.07 (d, J=8.0 Hz, 2H), 735 (d, J=16.0 Hz, 1H), 7.38 (d, J=8.0 Hz, 2H), 11.56 (s, 1H), 11.45 (s, 1H), 12.03 (br, 1H).

Example 75

Preparation of methyl 2,4-dimethoxy-6-[(E)-2-(pyridin-4-yl)ethenyl]benzoate (6r)

Use 4-pyridinecarboxaldehyde as material, and follow the method described in Example 5 to obtain a white solid as the product (83%). ¹H NMR (400 MHz, CDCl₃): 3.73 (s, 3H), 3.77 (s, 3H), 3.88 (s, 3H), 6.48 (s, 1H), 6.70 (s, 1H), 6.84 (d, J=16.0 Hz, 1H), 7.35 (d, J=16.0 Hz, 1H), 7.51 (d, J=8.0 Hz, 2H), 8.50 (d, J=8.0 Hz, 2H).

Example 76

Preparation of methyl 2-hydroxy-4-methoxy-6-[(E)-2-(pyridin-4-yl)ethenyl]benzoate (7r)

Use Compound 6r as material, and follow the method similar to what is described in Example 6 to obtain a white solid as the product (85%). ¹H NMR (400 MHz, CDCl₃): 3.78 (s, 3H), 3.90 (s, 3H), 6.46 (s, 1H), 6.69 (s, 1H), 6.83 (d, J=16.0 Hz, 1H), 7.32 (d, J=16.0 Hz, 1H), 7.55 (d, J=8.0 Hz, 2H), 8.49 (d, J=8.0 Hz, 2H), 11.45 (s, 1H).

Example 77

Preparation of methyl 2-hydroxy-3-isopentenyl-4-methoxy-6-[(E)-2-(pyridin-4-yl)ethenyl]benzoate (8r)

Use Compound 7r as material, and follow the method similar to what is described in Example 7 to obtain a white solid as the product (60%). ¹H NMR (400 MHz, CDCl₃): 1.65 (s, 3H), 1.78 (s, 3H), 3.35 (d, J=7.2 Hz, 2H), 3.85 (s, 3H), 3.94 (s, 3H), 5.21 (t, J=7.2 Hz, 1H), 6.70 (s, 1H), 6.79 (d, J=16.0 Hz, 1H), 733 (d, J=16.0 Hz, 1H), 732 (d, J=8.0 Hz, 2H), 8.53 (d, J=8.0 Hz, 2H), 11.45 (s, 1H).

Example 78

Preparation of 2-hydroxy-3-isopentenyl-4-methoxy-6-[(E)-2-(pyridin-4-yl)ethenyl]benzoic acid (1r)

Use Compound 8r as material, and follow the method similar to what is described in Example 8 to obtain a white solid as the product (90%). ¹H NMR (400 MHz, DMSO-d₆): 1.63 (s, 3H), 1.78 (s, 3H), 3.32 (d, J=7.2 Hz, 2H), 3.94 (s, 3H), 5.23 (t, J=7.2 Hz, 1H), 6.72 (s, 1H), 6.80 (d, J=16.0 Hz, 1H), 7.37 (d, J=16.0 Hz, 1H), 737 (d, J=8.0 Hz, 2H), 8.58 (d, J=8.0 Hz, 2H), 11.65 (s, 1H), 11.89 (br, 1H).

Example 79

Preparation of methyl 2,4-dimethoxy-6-[(E)-2-formyloxstyryl]benzoate (6s)

Use methyl 2-carbonyl-2-phenylacetate as material, and follow the method described in Example 5 to obtain a white solid as the product (83%). ¹H NMR (400 MHz, CDCl₃): 3.69 (s, 3H), 3.73 (s, 3H), 3.77 (s, 3H), 3.88 (s, 3H), 6.48 (s, 1H), 6.70 (s, 1H), 7.12 (s, 1H), 7.30 (t, J=7.6 Hz, 1H), 7.42 (t, J=7.6 Hz, 2H) 7.58 (d, J=7.6 Hz, 2H).

Example 80

Preparation of methyl 2-hydroxy-4-methoxy-6-[(E)-2-formyloxstyryl]benzoate (7s)

Use Compound 6s as material, and follow the method similar to what is described in Example 6 to obtain a white solid as the product (85%). $^1$H NMR (400 MHz, CDCl$_3$): 3.66 (s, 3H), 3.75 (s, 3H), 3.87 (s, 3H), 6.43 (s, 1H), 6.72 (s, 1H), 6.87 (s, 1H), 7.31 (t, J=7.6 Hz, 1H), 7.43 (t, J=7.6 Hz, 2H) 7.57 (d, J=7.6 Hz, 2H), 11.42 (s, 1H).

Example 81

Preparation of methyl 2-hydroxy-3-isopentenyl-4-methoxy-6-[(E)-2-formyloxstyryl]benzoate (8s)

Use Compound 7s as material, and follow the method similar to what is described in Example 7 to obtain a white solid as the product (60%). $^1$H NMR (400 MHz, CDCl$_3$): 1.69 (s, 3H), 1.72 (s, 3H), 3.22 (d, J=7.2 Hz, 2H), 3.63 (s, 3H), 3.78 (s, 3H), 3.84 (s, 3H), 5.21 (t, J=7.2 Hz, 1H), 636 (s, 1H), 7.15 (s, 1H), 7.23 (t, J=7.6 Hz, 2H), 738 (t, J=7.6 Hz, 2H), 7.48 (d, J=7.6 Hz, 1H), 11.46 (s, 1H).

Example 82

Preparation of 2-hydroxy-3-isopentenyl-4-methoxy-6-[(E)-2-formyloxstyryl]benzoic acid (1s)

Use Compound 8s as material, and follow the method similar to what is described in Example 8 to obtain a white solid as the product (90%). $^1$H NMR (400 MHz, DMSO-d$_6$): 1.67 (s, 3H), 1.69 (s, 3H), 3.24 (d, J=7.2 Hz, 2H), 3.65 (s, 3H), 3.84 (s, 3H), 5.23 (t, J=7.2 Hz, 1H), 6.54 (s, 1H), 7.14 (s, 1H), 7.24 (t, J=7.6 Hz, 2H), 7.41 (t, J=7.6 Hz, 2H), 7.51 (d, J=7.6 Hz, 1H), 11.46 (s, 1H), 12.57 (br, 1H).

Example 83

Preparation of methyl 2,4-dimethoxy-6-[(E)-2-(pyrid-2-yl)ethenyl]benzoate (6t)

Use 2-pyridinecarboxaldehyde as material, and follow the method described in Example 5 to obtain a white solid as the product (75%). $^1$H NMR (400 MHz, DMSO-d$_6$): 3.73 (s, 6H), 3.83 (s, 3H), 6.40 (s, 1H), 6.68 (s, 1H), 7.06 (d, J=16.0 Hz, 1H), 7.39 (t, J=7.6 Hz, 1H), 7.49 (d, J=7.6 Hz, 1H), 7.61 (t, J=7.6 Hz, 1H), 7.87 (d, J=16.0 Hz, 1H), 8.63 (d, J=7.6 Hz, 1H).

Example 84

Preparation of methyl 2-hydroxy-4-methoxy-6-[(E)-2-(pyrid-2-yl)ethenyl]benzoate (7t)

Use Compound 6t as material, and follow the method described in Example 6 to obtain a white solid as the product (85%). $^1$H NMR (400 MHz, DMSO-d$_6$): 3.74 (s, 3H), 3.83 (s, 3H), 6.42 (s, 1H), 6.70 (s, 1H), 7.04 (d, J=16.0 Hz, 1H), 7.40 (t, J=7.6 Hz, 1H), 7.52 (d, J=7.6 Hz, 1H), 7.62 (t, J=7.6 Hz, 1H), 7.89 (d, J=16.0 Hz, 1H), 8.53 (d, J=7.6 Hz, 1H), 11.20 (s, 1H).

Example 85

Preparation of methyl 2-hydroxy-3-isopentenyl-4-methoxy-6-[(E)-2-(pyrid-2-yl)ethenyl]benzoate (8t)

Use Compound 7t as material, and follow the method described in Example 7 to obtain a white solid as the product (64%). $^1$H NMR (400 MHz, DMSO-d$_6$): 1.85 (s, 3H), 1.92 (s, 3H), 3.42 (d, J=8.0 Hz, 2H), 3.88 (s, 6H), 5.21 (t, J=8.0 Hz, 1H), 6.71 (s, 1H), 7.22 (d, J=16.0 Hz, 1H), 7.42 (d, J=7.6 Hz, 1H), 7.53 (d, J=7.6 Hz, 1H), 7.60 (t, J=7.6 Hz, 1H), 7.84 (d, J=16.6 Hz, 2H), 8.39 (d, J=7.6 Hz, 1H), 11.23 (s, 1H).

Example 86

Preparation of 2-hydroxy-3-isopentenyl-4-methoxy-6-[(E)-2-(pyrid-2-yl)ethenyl]benzoic acid (1t)

Use Compound 8t as material, and follow the method described in Example 8 to obtain a white solid as the product (85%). $^1$H NMR (400 MHz, DMSO-d$_6$): 1.83 (s, 3H), 1.91 (s, 3H), 3.48 (d, J=8.0 Hz, 2H), 3.83 (s, 3H), 5.21 (t, J=8.0 Hz, 1H), 6.70 (s, 1H), 7.22 (d, J=16.0 Hz, 1H), 7.41 (d, J=7.6 Hz, 1H), 7.52 (d, J=7.6 Hz, 1H), 7.62 (t, J=7.6 Hz, 1H), 7.80 (d, J=16.6 Hz, 2H), 8.41 (d, J=7.6 Hz, 1H), 11.20 (s, 1H), 12.13 (s, 1H).

Example 87

Preparation of methyl 2,4-dimethoxy-6-[(E)-(3,4,5-trimethoxystyryl)]benzoate (6u)

Use 3,4,5-trimethoxybenzaldehyde as material, and follow the method described in Example 5 to obtain a white solid as the product (78%). $^1$H NMR (400 MHz, DMSO-d$_6$): 3.78 (s, 3H), 3.85 (s, 3H), 3.89 (s, 6H) 3.95 (s, 6H), 6.60 (s, 1H), 6.82 (s, 1H), 6.95 (s, 2H), 7.00 (s, J=16.0 Hz, 1H), 7.14 (t, J=16.0 Hz, 3H).

Example 88

Preparation of methyl 2-hydroxy-4-methoxy-6-[(E)-(3,4,5-trimethoxy-styryl)]benzoate (7u)

Use Compound 6u as material, and follow the method described in Example 6 to obtain a white solid as the product (83%). $^1$H NMR (400 MHz, DMSO-d$_6$): 3.86 (s, 3H), 3.78 (s, 6H) 3.90 (s, 6H), 6.45 (s, 1H), 6.75 (s, 1H), 6.96 (s, 2H), 7.02 (s, J=16.0 Hz, 1H), 7.24 (t, J=16.0 Hz, 3H), 11.23 (s, 1H).

Example 89

Preparation of methyl 2-hydroxy-3-isopentenyl-4-methoxy-6-[(E)-(3,4,5-trimethoxy-styryl)]benzoate (8u)

Use Compound 7u as material, and follow the method described in Example 7 to obtain a white solid as the product (64%). $^1$H NMR (400 MHz, DMSO-d$_6$): 1.85 (s, 3H), 1.90 (s, 3H), 3.41 (d, J=8.0 Hz, 2H), 3.88 (s, 6H), 3.90 (s, 6H), 5.21 (t, J=8.0 Hz, 1H), 6.70 (s, 1H), 7.05 (s, 2H), 7.10 (s, J=16.0 Hz, 1H), 7.28 (t, J=16.0 Hz, 3H), 11.23 (s, 1H).

Example 90

Preparation of 2-hydroxy-3-isopentenyl-4-methoxy-6-[(E)-(3,4,5-trimethoxystyryl)]benzoic acid (1u)

Use Compound 8u as material, and follow the method described in Example 8 to obtain a white solid as the product (90%). $^1$H NMR (400 MHz, DMSO-d$_6$): 1.85 (s, 3H), 1.92 (s, 3H), 3.35 (d, J=7.6 Hz, 2H), 3.88 (s, 9H), 5.21 (t, J=7.6 Hz, 1H), 6.75 (s, 1H), 7.10 (s, 2H), 7.12 (s, J=16.0 Hz, 1H), 7.25 (t, J=16.0 Hz, 3H), 11.23 (s, 1H), 12.34 (s, 1H).

Example 91

Preparation of methyl 2,4-dimethoxy-6-[(E)-2-(4-methoxypyrid-2-yl)ethenyl]benzoate (6v)

Use 2-formyl-4-methoxypyridine as material, and follow the method described in Example 5 to obtain a white solid as the product (75%). $^1$H NMR (400 MHz, DMSO-d$_6$): 3.85 (s, 6H), 3.92 (s, 3H), 3.98 (s, 3H), 6.49 (s, 1H), 6.69 (s, 1H), 7.09 (s, 1H), 7.18 (d, J=16.0 Hz, 1H), 732 (d, J=7.6 Hz, 1H), 7.46 (d, J=16.0 Hz, 1H), 831 (d, J=7.6 Hz, 1H).

Example 92

Preparation of methyl 2-hydroxy-4-methoxy-6-[(E)-2-(4-methoxy-pyrid-2-yl)ethenyl]benzoate (7v)

Use Compound 6v as material, and follow the method described in Example 6 to obtain a white solid as the product (85%). $^1$H NMR (400 MHz, DMSO-d$_6$): 3.92 (s, 3H), 3.97 (s, 3H), 6.48 (s, 1H), 6.64 (s, 1H), 7.04 (s, 1H), 7.15 (d, J=16.0 Hz, 1H), 7.34 (d, J=7.6 Hz, 1H), 7.44 (d, J=16.0 Hz, 1H), 8.32 (d, J=7.6 Hz, 1H), 11.31 (s, 1H).

Example 93

Preparation of methyl 2-hydroxy-3-isopentenyl-4-methoxy-6-[(E)-2-(4-methoxypyrid-2-yl)ethenyl]benzoate (8v)

Use Compound 7v as material, and follow the method described in Example 7 to obtain a white solid as the product (63%). $^1$H NMR (400 MHz, DMSO-d$_6$): 1.80 (s, 3H), 1.92 (s, 3H), 3.45 (d, J=7.6 Hz, 2H), 3.88 (s, 3H), 3.90 (s, 6H), 5.21 (t, J=7.6 Hz, 1H), 6.75 (s, 1H), 7.05 (s, 1H), 7.15 (d, J=16.0 Hz, 1H), 732 (d, J=7.6 Hz, 1H), 7.44 (d, J=16.0 Hz, 1H), 8.30 (d, J=7.6 Hz, 1H), 11.31 (s, 1H).

Example 94

Preparation of 2-hydroxy-3-isopentenyl-4-methoxy-6-[(E)-2-(4-methoxypyrid-2-yl)ethenyl]benzoic acid (1v)

Use Compound 8v as material, and follow the method described in Example 8 to obtain a white solid as the product (85%). $^1$H NMR (400 MHz, DMSO-d$_6$): 1.82 (s, 3H), 1.91 (s, 3H), 3.42 (d, J=7.6 Hz, 2H), 3.82 (s, 3H), 3.86 (s, 3H), 5.22 (t, J=7.6 Hz, 1H), 6.73 (s, 1H), 7.04 (s, 1H), 7.15 (d, J=16.0 Hz, 1H), 734 (d, J=7.6 Hz, 1H), 7.44 (d, J=16.0 Hz, 1H), 8.32 (d, J=7.6 Hz, 1H), 11.31 (s, 1H), 12.54 (s, 1H).

Example 95

Preparation of 2-hydroxy-3-isopentenyl-4-methoxy-6-[(E)-2-(4-hydroxypyrid-2-yl)ethenyl]benzoic acid (1w)

Use Compound 1v as material, and follow the method described in Example 6 to obtain a white solid as the product (85%). $^1$H NMR (400 MHz, DMSO-d$_6$): 1.80 (s, 3H), 1.90 (s, 3H), 3.44 (d, J=7.6 Hz, 2H), 3.86 (s, 3H), 5.20 (t, J=7.6 Hz, 1H), 6.74 (s, 1H), 7.08 (s, 1H), 7.16 (d, J=16.0 Hz, 1H), 7.35 (d, J=7.6 Hz, 1H), 7.46 (d, J=16.0 Hz, 1H), 8.30 (d, J=7.6 Hz, 1H), 10.21 (s, 1H), 11.31 (s, 1H), 12.54 (s, 1H).

Example 96

Preparation of methyl 2,4-dimethoxy-6-[(E)-2-(3-methoxypyrid-2-yl)ethenyl]benzoate (6w)

Use 2-formyl 3-methoxy-pyridine as material, and follow the method described in Example 5 to obtain a white solid as the product (78%). $^1$H NMR (400 MHz, DMSO-d$_6$): 3.87 (s, 6H), 3.96 (s, 6H), 6.45 (s, 1H), 6.73 (s, 1H), 7.14 (d, J=7.6 Hz, 1H), 7.16 (d, J=16.0 Hz, 1H), 7.50 (d, J=7.6 Hz, 1H), 7.52 (d, J=16.0 Hz, 1H), 8.10 (s, 1H).

Example 97

Preparation of methyl 2-hydroxy-4-methoxy-6-[(E)-2-(3-methoxypyrid-2-yl)ethenyl]benzoate (7w)

Use Compound 6w as material, and follow the method described in Example 6 to obtain a white solid as the product (82%). $^1$H NMR (400 MHz, DMSO-d$_6$): 3.88 (s, 3H), 3.92 (s, 6H), 6.49 (s, 1H), 6.78 (s, 1H), 7.16 (d, J=7.6 Hz, 1H), 7.19 (d, J=16.0 Hz, 1H), 7.45 (d, J=7.6 Hz, 1H), 7.50 (d, J=16.0 Hz, 1H), 8.11 (s, 1H), 11.23 (s, 1H).

Example 98

Preparation of methyl 2-hydroxy-3-isopentenyl-4-methoxy-6-[(E)-2-(3-methoxypyrid-2-yl)ethenyl]benzoate (8w)

Use Compound 7w as material, and follow the method described in Example 7 to obtain a white solid as the product (61%). $^1$H NMR (400 MHz, DMSO-d$_6$): 1.80 (s, 3H), 1.90 (s, 3H), 3.44 (d, J=7.6 Hz, 2H), 3.88 (s, 3H), 3.92 (s, 6H), 5.21 (t, J=7.6 Hz, 1H), 6.74 (s, 1H), 7.15 (d, J=7.6 Hz, 1H), 7.18 (d, J=16.0 Hz, 1H), 7.44 (d, J=7.6 Hz, 1H), 7.55 (d, J=16.0 Hz, 1H), 8.14 (s, 1H), 10.23 (s, 1H).

Example 99

Preparation of 2-hydroxy-3-isopentenyl-4-methoxy-6-[(E)-2-(3-methoxypyrid-2-yl)ethenyl]benzoic acid (1x)

Use Compound 8w as material, and follow the method described in Example 8 to obtain a white solid as the product (85%). $^1$H NMR (400 MHz, DMSO-d$_6$): 1.80 (s, 3H), 1.91 (s, 3H), 3.41 (d, J=7.6 Hz, 2H), 3.89 (s, 3H), 3.92 (s, 3H), 5.21 (t, J=7.6 Hz, 1H), 6.77 (s, 1H), 7.15 (d, J=7.6 Hz, 1H), 7.18 (d, J=16.0 Hz, 1H), 7.44 (d, J=7.6 Hz, 1H), 7.50 (d, J=16.0 Hz, 1H), 8.11 (s, 1H), 10.29 (s, 1H), 12.32 (s, 1H).

Example 100

Preparation of 2-hydroxy-3-isopentenyl-4-methoxy-6-[(E)-2-(3-hydroxypyryd-2-yl)ethenyl]benzoic acid (1y)

Use Compound 1x as material, and follow the method described in Example 6 to obtain a white solid as the product (54%). $^1$H NMR (400 MHz, DMSO-d$_6$): 1.80 (s, 3H), 1.91 (s, 3H), 3.41 (d, J=7.6 Hz, 2H), 3.92 (s, 3H), 5.21 (t, J=7.6 Hz, 1H), 6.72 (s, 1H), 7.14 (d, J=7.6 Hz, 1H), 7.16 (d, J=16.0 Hz, 1H), 7.43 (d, J=7.6 Hz, 1H), 7.51 (d, J=16.0 Hz, 1H), 8.12 (s, 1H), 10.21 (s, 1H), 10.29 (s, 1H), 12.32 (s, 1H).

Example 101

Preparation of methyl 2,4-dimethoxy-6-[(E)-2-(4,6-dimethoxy-pyrid-2-yl)ethenyl]benzoate (6x)

Use 2-formyl-4,6-dimethoxypyridine as material, and follow the method described in Example 5 to obtain a white solid as the product (75%). $^1$H NMR (400 MHz, DMSO-$d_6$): 3.87 (s, 9H) 3.94 (s, 6H), 6.24 (s, 1H), 6.26 (s, 1H), 6.50 (s, 1H), 6.69 (s, 1H), 7.08 (d, J=16.0 Hz, 1H), 7.72 (d, J=16.0 Hz, 1H).

Example 102

Preparation of methyl 2-hydroxy-4-methoxy-6-[(E)-2-(4,6-dimethoxy-pyrid-2-yl)ethenyl]benzoate (7x)

Use Compound 6x as material, and follow the method described in Example 6 to obtain a white solid as the product (85%). $^1$H NMR (400 MHz, DMSO-$d_6$): 3.87 (s, 3H), 3.91 (s, 3H), 3.94 (s, 6H), 6.23 (s, 1H), 6.27 (s, 1H), 6.48 (s, 1H), 6.70 (s, 1H), 7.12 (d, J=16.0 Hz, 1H), 7.52 (d, J=16.0 Hz, 1H), 11.21 (s, 1H).

Example 103

Preparation of methyl 2-hydroxy-3-isopentenyl-4-methoxy-6-[(E)-2-(4,6-dimethoxypyrid-2-yl)ethenyl]benzoate (8x)

Use Compound 7x as material, and follow the method described in Example 7 to obtain a white solid as the product (65%). $^1$H NMR (400 MHz, DMSO-$d_6$): 1.85 (s, 3H), 1.90 (s, 3H), 3.43 (d, J=7.6 Hz, 2H), 3.89 (s, 3H), 3.91 (s, 3H), 3.92 (s, 6H) 5.21 (t, J=7.6 Hz, 1H), 6.23 (s, 1H), 6.27 (s, 1H), 6.70 (s, 1H), 7.13 (d, J=16.0 Hz, 1H), 7.50 (d, J=16.0 Hz, 1H), 10.21 (s, 1H).

Example 104

Preparation of 2-hydroxy-3-isopentenyl-4-methoxy-6-[(E)-2-(4,6-dimethoxy-pyrid-2-yl)ethenyl]benzoic acid (1z)

Use Compound 8x as material, and follow the method described in Example 8 to obtain a white solid as the product (85%). $^1$H NMR (400 MHz, DMSO-$d_6$): 1.88 (s, 3H), 1.95 (s, 3H), 3.40 (d, J=7.6 Hz, 2H), 3.91 (s, 3H), 3.94 (s, 6H), 5.23 (t, J=7.6 Hz, 1H), 62 (s, 1H), 6.28 (s, 1H), 6.72 (s, 1H), 7.16 (d, J=16.0 Hz, 1H), 730 (d, J=16.0 Hz, 1H), 10.29 (s, 1H), 12.45 (s, 1H).

Example 105

Preparation of 2-hydroxy-3-isopentenyl-4-methoxy-6-[(E)-2-(4,6-dihydroxy-2-yl)ethenyl]benzoic acid (1a)

Use Compound 1z as material, and follow the method described in Example 6 to obtain a white solid as the product (65%). $^1$H NMR (400 MHz, DMSO-$d_6$): 1.88 (s, 3H), 1.95 (s, 3H), 3.40 (d, J=7.6 Hz, 2H), 3.91 (s, 3H), 5.23 (t, J=7.6 Hz, 1H), 6.22 (s, 1H), 68 (s, 1H), 6.72 (s, 1H), 7.16 (d, J=16.0 Hz, 1H), 7.50 (d, J=16.0 Hz, 1H), 10.21 (s, 1H), 10.29 (s, 1H), 11.10 (s, 1H), 12.45 (s, 1H).

Example 106

Preparation of methyl 2,4-dimethoxy-6-[(E)-2-(6-methoxy-pyrid-2-yl)ethenyl]benzoate (6y)

Use 2-formyl-6-methoxypyridine as material, and follow the method described in Example 5 to obtain a white solid as the product (75%). $^1$H NMR (400 MHz, DMSO-$d_6$): 3.87 (s, 6H) 3.96 (s, 6H), 6.49 (d, J=7.2 Hz, 1H), 6.52 (d, J=7.2 Hz, 1H), 6.53 (s, 1H), 6.73 (s, 1H), 7.22 (d, J=16.0 Hz, 1H), 7.47 (t, J=7.6 Hz, 1H), 7.67 (d, J=16.0 Hz, 1H).

Example 107

Preparation of methyl 2-hydroxy-4-methoxy-6-[(E)-2-(6-methoxy-pyrid-2-yl)ethenyl]benzoate (7y)

Use Compound 6y as material, and follow the method described in Example 6 to obtain a white solid as the product (85%). $^1$H NMR (400 MHz, DMSO-$d_6$): 3.89 (s, 3H), 3.94 (s, 6H), 6.51 (d, J=7.2 Hz, 1H), 6.54 (d, J=7.2 Hz, 1H), 6.55 (s, 1H), 6.74 (s, 1H), 7.20 (d, J=16.0 Hz, 1H), 7.41 (t, J=7.6 Hz, 1H), 7.64 (d, J=16.0 Hz, 1H), 11.32 (s,

Example 108

Preparation of methyl 2-hydroxy-3-isopentenyl-4-methoxy-6-[(E)-2-(6-methoxy-pyrid-2-yl)ethenyl]benzoate (8y)

Use Compound 7y as material, and follow the method described in Example 7 to obtain a white solid as the product (64%). $^1$H NMR (400 MHz, DMSO-$d_6$): 1.88 (s, 3H), 1.95 (s, 3H), 3.43 (d, J=7.6 Hz, 2H), 3.89 (s, 3H), 3.94 (s, 6H), 5.23 (t, J=7.6 Hz, 1H), 6.51 (d, J=7.2 Hz, 1H), 6.54 (d, J=7.2 Hz, 1H), 6.70 (s, 1H), 7.22 (d, J=16.0 Hz, 1H), 7.43 (t, J=7.6 Hz, 1H), 7.68 (d, J=16.0 Hz, 1H), 11.32 (s, 1H).

Example 109

Preparation of 2-hydroxy-3-isopentenyl-4-methoxy-6-[(E)-2-(6-methoxypyrid-2-yl)ethenyl]benzoic acid (1b)

Use Compound 8y as material, and follow the method described in Example 8 to obtain a white solid as the product (85%). $^1$H NMR (400 MHz, DMSO-$d_6$): 1.88 (s, 3H), 1.95 (s, 3H), 3.43 (d, J=7.6 Hz, 2H), 3.94 (s, 6H), 5.23 (t, J=7.6 Hz, 1H), 6.56 (d, J=7.2 Hz, 1H), 6.58 (d, J=7.2 Hz, 1H), 6.68 (s, 1H), 7.20 (d, J=16.0 Hz, 1H), 7.35 (t, J=7.6 Hz, 1H), 7.54 (d, J=16.0 Hz, 1H), 10.32 (s, 1H), 12.54 (s, 1H).

Example 110

Preparation of 2-hydroxy-3-isopentenyl-4-methoxy-6-[(E)-2-(6-hydroxypyrid-2-yl)ethenyl]benzoic acid (1c)

Use Compound 1b as material, and follow the method described in Example 6 to obtain a white solid as the product (56%). $^1$H NMR (400 MHz, DMSO-$d_6$): 1.89 (s, 3H), 1.90 (s, 3H), 3.40 (d, J=7.6 Hz, 2H), 3.91 (s, 3H), 5.23 (t, J=7.6 Hz, 1H), 6.55 (d, J=7.2 Hz, 1H), 6.58 (d, J=7.2 Hz, 1H), 6.67 (s, 1H), 7.18 (d, J=16.0 Hz, 1H), 7.39 (t, J=7.6 Hz, 1H), 7.44 (d, J=16.0 Hz, 1H), 9.98 (s, 1H), 10.32 (s, 1H), 12.54 (s, 1H).

Example 111

Preparation of methyl 2-hydroxy-3-allyl-4-methoxy-6-[(E)-styryl]benzoate (8a)

Use Compound 7 and allyl bromide as materials, and follow the method described in Example 7 to obtain a white solid as the product (58%). $^1$H NMR (400 MHz, DMSO-d$_6$): 3.22 (d, J=7.6 Hz, 2H), 3.75 (s, 3H), 3.89 (s, 3H), 4.93 (dd, J1=16.0 Hz, J2=12.0 Hz, 1H), 4.96 (dd, J1=6.4 Hz, J2=12.0 Hz, 1H), 6.30 (m, 1H), 6.70 (s, 1H), 6.82 (d, J=16.0 Hz, 1H), 7.30 (m, 2H), 7.42 (d, J=7.6 Hz, 2H), 7.48 (t, J=7.6 Hz, 2H), 9.83 (s, 1H).

Example 112

Preparation of methyl 2-hydroxy-3-allyl-4-methoxy-6-[(E)-styryl]benzoate (1d)

Use Compound 8a as material, and follow the method described in Example 8 to obtain a white solid as the product (89%). $^1$H NMR (400 MHz, DMSO-d$_6$): 3.21 (d, J=7.6 Hz, 2H), 3.78 (s, 3H), 4.92 (dd, J1=16.0 Hz, J2=12.0 Hz, 1H), 4.95 (dd, J1=6.4 Hz, J2=12.0 Hz, 1H), 6.32 (m, 1H), 6.71 (s, 1H), 6.80 (d, J=16.0 Hz, 1H), 732 (m, 2H), 7.43 (d, J=7.6 Hz, 2H), 7.53 (t, J=7.6 Hz, 2H), 9.82 (s, 1H), 12.56 (s, 1H).

Example 113

Preparation of methyl 2-hydroxy-3-isopentenyl-4-methoxy-6-[(E)-styryl]benzoate (9a)

Dissolve cajanine (0.2 g, 0.59 mmol) in absolute ethanol (10 ml), add in DCC (0.15 g, 0.71 mmol) at room temperature, after finishing the addition, continue the reaction for 2 h to complete the reaction, evaporate the ethanol, redissolve the residue and feed the solution to silica gel column, evaporate the solvent in the eluent to obtain a white solid (0.19 g, 92%). $^1$H NMR (400 MHz, CDCl$_3$): 1.38 (t, J=7.2 Hz, 3H), 1.68 (s, 3H), 1.79 (s, 3H), 3.37 (d, J=7.2 Hz, 2H), 3.92 (s, 3H), 4.39 (q, J=7.2 Hz, 2H), 5.21 (t, J=7.2 Hz, 1H), 6.60 (s, 1H), 6.75 (d, J=16.0 Hz, 1H), 7.27 (t, J=7.6 Hz, 1H), 7.37 (t, J=7.6 Hz, 2H), 7.50 (d, J=7.6 Hz, 2H), 7.77 (d, J=16.0 Hz, 1H), 11.77 (s, 1H).

Example 114

Preparation of isopropyl 2-hydroxy-3-isopentenyl-4-methoxy-6-[(E)-styryl]benzoate (9b)

Use isopropanol as solvent, follow the method described in Example 113 to obtain a white solid as the product (90%). $^1$H NMR (400 MHz, CDCl$_3$): 1.35 (d, J=6.4 Hz, 6H), 1.68 (s, 3H), 1.79 (s, 3H), 3.37 (d, J=6.8 Hz, 2H), 3.92 (s, 3H), 5.22 (t, J=6.8 Hz, 1H), 5.29 (q, J=6.4 Hz, 1H), 6.59 (s, 1H), 6.73 (d, J=16.0 Hz, 1H), 7.27 (t, J=7.6 Hz, 1H), 7.37 (t, J=7.6 Hz, 2H), 7.50 (d, J=7.6 Hz, 2H), 7.76 (d, J=16.0 Hz, 1H), 11.83 (s, 1H).

Example 115

Preparation of tert-butyl2-hydroxy-3-isopentenyl-4-methoxy-6-[(E)-styryl]-benzoate (9c)

Use tert-butanol as solvent, follow the method described in Example 113 to obtain a white solid as the product (89%). $^1$H NMR (400 MHz, CDCl$_3$): 1.55 (s, 9H), 1.68 (s, 3H), 1.79 (s, 3H), 3.37 (d, J=7.2 Hz, 2H), 3.90 (s, 3H), 5.22 (t, J=7.2 Hz, 1H), 6.55 (s, 1H), 6.71 (d, J=16.0 Hz, 1H), 7.27 (t, J=7.6 Hz, 1H), 737 (t, J=7.6 Hz, 2H), 7.49 (d, J=7.6 Hz, 2H), 7.71 (d, J=16.0 Hz, 1H), 11.93 (s, 1H).

Example 116

Preparation of N-cyclopropyl-2-hydroxy-3-isopentenyl-4-methoxy-6-[(E)-styryl]benzamide (9d)

Dissolve cajanine (0.2 g, 0.59 mmol) in dichloromethane (15 ml), add in DCC (0.15 g, 0.71 mmol), stir at room temperature for 0.5h, subsequently add cyclopropylamine (50 mg, 0.88 mmol), stir at room temperature for 3h, evaporate the solvent after completion of the reaction, redissolve the residue and feed the solution to a silica gel column, evaporate the solvent in the eluent to obtain a white solid (85%). $^1$H NMR (400 MHz, CDCl$_3$): 0.48 (m, 2H), 0.83 (m, 2H), 1.68 (s, 3H), 1.79 (s, 3H), 2.88 (m, 1H), 3.37 (d, J=7.2 Hz, 2H), 3.89 (s, 3H), 5.22 (t, J=7.2 Hz, 1H), 6.23 (br, 1H), 6.46 (s, 1H), 6.89 (d, J=16.0 Hz, 1H), 7.24 (d, J=16.0 Hz, 1H), 7.33 (t, J=7.6 Hz, 1H), 7.41 (t, J=7.6 Hz, 2H), 7.47 (d, J=7.6 Hz, 2H).

Example 117

Preparation of 2,3-dihydroxypropyl2-hydroxy-3-isopentenyl-4-methoxy-6-[(E)-styryl]benzoate (9e)

Use glycerol as material, follow the method described in Example 116 to obtain a white solid as the target product (65%). $^1$H NMR (400 MHz, CDCl$_3$): 1.82 (s, 3H), 1.91 (s, 3H), 3.22 (d, J=7.6 Hz, 2H), 3.56 (m, 1H), 3.73 (s, 3H), 3.81 (m, 1H), 3.90 (m, 1H), 4.28 (m, 1H), 4.53 (m, 1H), 4.78 (s, 1H), 4.81 (s, 1H), 5.22 (t, J=7.6 Hz, 1H), 6.70 (s, 1H), 6.82 (d, J=16.0 Hz, 1H), 7.26 (d, J=16.0 Hz, 1H), 7.30 (d, J=8.0 Hz, 1H), 7.42 (d, J=8.0 Hz, 2H), 7.45 (t, J=8.0 Hz, 2H), 9.98 (s, 1H).

Example 118

Preparation of N-(piperidin-4-yl)2-hydroxy-isopentenyl-4-methoxy-6-[(E)-styryl]benzamide (9f)

Use piperidin-4-amine as material, follow the method described in Example 116 to obtain a white solid as the target product (60%). $^1$H NMR (400 MHz, CDCl$_3$): 1.68 (s, 3H), 1.76 (m, 4H), 1.79 (s, 3H), 2.74 (m, 4H), 3.22 (d, J=7.6 Hz, 2H), 3.60 (m 1H), 3.73 (s, 3H), 432 (s, 1H), 5.21 (t, J=7.6 Hz, 1H), 6.68 (s, 1H), 6.82 (d, J=16.0 Hz, 1H), 7.24 (d, J=16.0 Hz, 1H), 7.32 (d, J=8.0 Hz, 1H), 7.45 (d, J=8.0 Hz, 2H), 7.48 (t, J=8.0 Hz, 2H), 8.45 (s, 1H), 9.98 (s, 1H).

Example 119

Preparation of N-phenyl-2-hydroxy-3-isopentenyl-4-methoxy-6-[(E)-styryl]benzamide (9g)

Use Aniline as material, follow the method described in Example 116 to obtain a white solid as the target product (78%). $^1$H NMR (400 MHz, CDCl$_3$): 1.78 (s, 3H), 1.79 (s, 3H), 3.26 (d, J=7.6 Hz, 2H), 3.73 (s, 3H), 5.20 (t, J=7.6 Hz, 1H), 6.69 (s, 1H), 6.84 (d, J=16.0 Hz, 1H), 7.28 (d, J=16.0 Hz, 1H), 7.32 (m, 3H), 7.45 (m, 5H), 7.70 (d, J=7.2 Hz, 2H), 9.89 (s, 1H), 10.35 (s, 1H).

Example 120

Preparation of N-p-chlorophenyl2-hydroxy-3-isopentenyl-4-methoxy-6-[(E)-styryl]benzamide (9h)

Use chloroaniline as material, follow the method described in Example 116 to obtain a white solid as the target product (85%). ¹H NMR (400 MHz, CDCl₃): 1.79 (s, 3H), 1.82 (s, 3H), 3.24 (d, J=7.6 Hz, 2H), 3.78 (s, 3H), 5.21 (t, J=7.6 Hz, 1H), 6.65 (s, 1H), 6.82 (d, J=16.0 Hz, 1H), 7.24 (d, J=16.0 Hz, 1H), 730 (t, J=7.6 Hz, 1H), 7.44 (m, 6H), 7.66 (d, J=7.2 Hz, 2H), 9.98 (s, 1H), 10.36 (s, 1H).

Example 121

Preparation of Cajanine A (10)

Dissolve compound 8 (1 g, 2.84 mmol) in 10 ml ethanol and 5 ml water, add in KOH (0.5 g, 8.5 mmol), react under microwave for 1h (30 W, 25 psi, 100° C.). After completion of the reaction. Pour the reaction solution into 50 ml water, adjust pH to less than 2 with 10% hydrochloric acid, extract the solution with ethyl acetate (3×30 ml), pool the organic layer, wash with saturated brine, dry over anhydrous magnesium sulfate overnight, then filter the solution, and concentrate it to obtain a pale yellow solid. Dissolve the solid with petroleum ether/ethyl acetate, feed the solution to a silica gel column to obtain a white solid 0.66 g (80%). ¹H NMR (400 MHz, CDCl₃): 1.75 (s, 3H), 1.82 (s, 3H), 3.41 (d, J=6.8 Hz, 2H), 3.87 (s, 3H), 5.24 (m, 2H), 6.64 (s, 1H), 6.66 (s, 1H), 7.02 (dd, J=16.0 Hz, 2H), 7.28 (t, J=7.2 Hz, 1H), 7.35 (t, J=7.2 Hz, 2H), 7.50 (d, J=7.2 Hz, 2H).

Example 122

Preparation of 2-isopentenyl-3-methoxy-5-[(E)-(4'-fluorostyryl)]phenol (10a)

Use Compound 8a as material, and follow the method similar to what is described in Example 121 to obtain a white solid as the target product (75%). ¹H NMR (400 MHz, CDCl₃): 1.76 (s, 3H), 1.79 (s, 3H), 3.35 (d, J=6.8 Hz, 2H), 3.88 (s, 3H), 5.21 (m, 2H), 6.64 (s, 1H), 6.67 (s, 1H), 7.02 (dd, J=16.0 Hz, 2H), 7.40 (d, J=8.4 Hz, 2H), 7.48 (d, J=8.4 Hz, 2H), 11.20 (s, 1H).

Example 123

Preparation of 2-isopentenyl-3-methoxy-5-[(E)-2'-chloroethylphenyl]phenol (10b)

Use Compound 8b as material, and follow the method similar to what is described in described in Example 121 to obtain a white solid as the target product (76%). ¹H NMR (400 MHz, CDCl₃): 1.61 (s, 3H), 1.71 (s, 3H), 3.25 (d, J=7.2 Hz, 2H), 3.90 (s, 3H), 5.11 (t, J=7.2 Hz, 1H), 6.37 (s, 1H), 6.33 (s, 1H), 7.13 (d, J=16.0 Hz, 1H), 7.35 (m, 2H), 7.47 (d, J=7.6 Hz, 1H), 7.74 (d. J=7.6 Hz, 1H), 7.86 (d, J=16.0 Hz, 1H), 11.61 (s, 1H).

Example 124

Preparation of 2-isopentenyl-3-methoxy-5-[(E)-4'-methoxystyryl]phenol (10c)

Use Compound 8c as material, and follow the method similar to what is described in Example 121 to obtain a white solid as the target product (73%). ¹H NMR (400 MHz, CDCl₃): 1.68 (s, 3H), 1.79 (s, 3H), 3.35 (d, J=6.8 Hz, 2H), 3.87 (s, 3H), 3.94 (s, 3H), 5.23 (t, J=6.8 Hz, 1H), 6.33 (s, 1H), 6.38 (s, 1H), 6.78 (d, J=16.0 Hz, 1H), 6.92 (d, J=8.4 Hz, 2H), 7.48 (d, J=8.4 Hz, 2H), 7.68 (d, J=16.0 Hz, 1H), 11.58 (s, 1H).

Example 125

Preparation of 2-isopentenyl-3-methoxy-5-[(E)-2',6'-dimethoxy-styryl]phenol (10d)

Use Compound 8d as material, and follow the method similar to what is described in Example 121 to obtain a white solid as the target product (72%). ¹H NMR (400 MHz, CDCl₃): 1.60 (s, 3H), 1.71 (s, 3H), 3.25 (d, J=7.2 Hz, 2H), 3.84 (s, 6H), 3.89 (s, 3H), 51 (t, J=7.2 Hz, 1H), 635 (s, 1H), 6.39 (s, 1H), 6.67 (d, J=8.0 Hz, 2H), 6.95 (d, J=16.0 Hz, 1H), 7.23 (t, J=8.0 Hz, 1H) 8.14 (d, J=16.0 Hz, 1H), 11.63 (s, 1H).

Example 126

Preparation of 2-isopentenyl-3-methoxy-5-[(E)-2'-methyl styryl]phenol (10e)

Use Compound 8e as material, and follow the method similar to what is described in Example 121 to obtain a white solid as the target product (72%). ¹H NMR (400 MHz, CDCl₃): 1.68 (s, 3H), 1.75 (s, 3H), 2.41 (s, 3H), 3.39 (d, J=7.2 Hz, 2H), 3.95 (s, 3H), 5.22 (t, J=7.2 Hz, 1H), 634 (s, 1H), 6.42 (s, 1H), 7.01 (d, J=15.6 Hz, 1H), 7.23 (m, 3H), 7.59 (d, J=7.2 Hz, 1H), 7.74 (d, J=15.6 Hz, 1H), 11.56 (s, 1H).

Example 127

Preparation of 2-isopentenyl-3-methoxy-5-[(E)-3'-methylstyryl]phenol (10f)

Use Compound 8f as material, and follow the method similar to what is described in Example 121 to obtain a white solid as the target product (74%). ¹H NMR (400 MHz, CDCl₃): 1.65 (s, 3H), 1.79 (s, 3H), 2.37 (s, 3H), 3.38 (d, J=6.8 Hz, 2H), 3.93 (s, 3H), 5.21 (t, J=6.8 Hz, 1H), 6.33 (s, 1H), 637 (s, 1H), 6.80 (d, J=15.6 Hz, 1H), 7.10 (d, J=7.2 Hz, 1H), 7.28 (m, 2H), 7.32 (s, 1H), 7.80 (d, J=15.6 Hz, 1H), 11.56 (s, 1H).

Example 128

Preparation of 2-isopentenyl-3-methoxy-5-[(E)-4'-methylstyryl]phenol (10g)

Use Compound 8c as material, and follow the method similar to what is described in Example 121 to obtain a white solid as the target product (72%). ¹H NMR (400 MHz, CDCl₃): 1.64 (s, 3H), 1.78 (s, 3H), 2.35 (s, 3H), 3.28 (d, J=7.2 Hz, 2H), 3.90 (s, 3H), 5.21 (t, J=7.2 Hz, 1H), 6.33 (s, 1H), 638 (s, 1H), 6.97 (d, J=16.0 Hz, 1H), 78 (d, J=8.4 Hz, 2H), 7.43 (d, J=8.4 Hz, 2H), 7.79 (d, J=16.0 Hz, 1H), 11.37 (s, 1H).

Example 129

Preparation of 2-isopentenyl-3-methoxy-5-[(E)-buten-1-yl]phenol (10h)

Use Compound 8h as material, and follow the method similar to what is described in Example 121 to obtain a white solid as the target product (77%). ¹H NMR (400 MHz, CDCl₃): 1.13 (t, J=7.2 Hz, 3H), 1.68 (s, 3H), 1.79 (s, 3H), 2.27 (m, 2H), 3.34 (d, J=6.8 Hz, 2H), 3.93 (s, 3H), 5.21 (t, J=6.8

Hz, 1H), 6.01 (m, 1H), 633 (s, 1H), 636 (s, 1H), 7.05 (d, J=15.6 Hz, 1H), 11.53 (s, 1H).

Example 130

Preparation of 2-isopentenyl-3-methoxy-5-[(E)-2-phenyl-propen-1'-yl]phenol (10i)

Use Compound 8i as material, and follow the method similar to what is described in Example 121 to obtain a white solid as the target product (77%). $^1$H NMR (400 MHz, CDCl$_3$): 1.63 (s, 3H), 1.76 (s, 3H), 2.25 (s, 3H), 3.27 (d, J=7.2 Hz), 3.34 (s, 3H), 5.17 (t, J=7.2 Hz, 1H), 5.90 (s, 1H), 6.33 (s, 1H), 6.38 (s, 1H), 7.16 (m, 5H), 11.53 (s, 1H).

Example 131

Preparation of 2-isopentenyl-3-methoxy-5-[((E)-2-(thien-2-yl)ethenyl]phenol (10j)

Use Compound 8j as material, and follow the method similar to what is described in Example 121 to obtain a white solid as the target product (77%). $^1$H NMR (400 MHz, CDCl$_3$): 1.63 (s, 3H), 1.75 (s, 3H), 3.23 (d, J=7.2 Hz, 2H), 3.91 (s, 3H), 5.21 (t, J=7.2 Hz, 1H), 6.33 (s, 1H), 6.39 (s, 1H), 7.06 (dd, J1=3.2 Hz, J2=4.0 Hz, 1H), 7.19 (d, J=3.2 Hz, 1H), 7.29 (d, J=15.6 Hz, 1H), 7.44 (d, J=4.0 Hz, 1H), 7.68 (d, J=15.6 Hz, 1H), 11.76 (s, 1H).

Example 132

Preparation of 2-isopentenyl-3'-methoxy-5-[(E)-3'-phenylpropen-1'-yl]phenol (10k)

Use Compound 8k as material, and follow the method similar to what is described in Example 121 to obtain a white solid as the target product (75%). $^1$H NMR (400 MHz, CDCl$_3$): 1.65 (s, 3H), 1.78 (s, 3H), 3.34 (d, J=7.2 Hz, 2H), 3.57 (d, J=6.8 Hz, 2H), 5.18 (t, J=6.8 Hz, 1H), 6.10 (m, 1H), 6.33 (s, 1H), 6.41 (s, 1H), 7.15 (d, J=16.0 Hz, 1H), 7.20 (m, 3H), 7.39 (t, J=8.0 Hz, 2H), 11.52 (s, 1H).

Example 133

Preparation of 2-isopentenyl-3-methoxy-5-[(E)-4'-phenylbuten-1'-yl]phenol (10l)

Use Compound 8l as material, and follow the method similar to what is described in Example 121 to obtain a white solid as the target product (77%). $^1$H NMR (400 MHz, CDCl$_3$): 1.66 (s, 3H), 1.78 (s, 3H), 2.55 (q, J=7.6 Hz, 2H), 2.83 (t, J=7.6 Hz, 2H), 3.35 (d, J=6.8 Hz, 2H), 3.88 (s, 3H), 5.23 (t, J=6.8 Hz, 1H), 5.95 (m, 1H), 6.33 (s, 1H), 6.39 (s, 1H), 7.08 (d, J=15.6 Hz, 1H), 7.29 (m, 5H), 11.58 (s, 1H).

Example 134

Preparation of 2-isopentenyl-3-methoxy-5-[(1'E, 3'E)-phenylbutadiene-1',3'-yl]phenol (10m)

Use Compound 8m as material, and follow the method similar to what is described in Example 121 to obtain a white solid as the target product (77%). $^1$H NMR (400 MHz, CDCl$_3$): 1.62 (s, 3H), 1.75 (s, 3H), 3.25 (d, J=7.2 Hz, 2H), 3.88 (s, 3H), 5.16 (t, J=7.2 Hz, 1H), 634 (s, 1H), 6.39 (s, 1H), 6.74 (d, J=15.6 Hz, 1H), 6.92 (dd, J1=15.2 Hz, J2=15.2 Hz, 1H), 7.10 (dd, J1=15.6 Hz, J2=15.2 Hz, 1H), 7.24 (t, J=7.6 Hz, 1H), 7.34 (t, J=7.6 Hz, 2H), 7.45 (d, J=15.2 Hz, 1H), 7.51 (d, J=7.6 Hz, 2H), 11.24 (s, 1H).

Example 135

Preparation of 2-isopentenyl-3-methoxy-5-[4'-methylcyclohexylene methyl]phenol (10n)

Use Compound 8n as material, and follow the method similar to what is described in Example 121 to obtain a white solid as the target product (78%). $^1$H NMR (400 MHz, CDCl$_3$): 0.94 (d, J=6.4 Hz, 3H), 0.95 (m, 1H), 1.13 (m, 1H), 1.56 (m, 1H), 1.69 (s, 3H), 1.78 (s, 3H), 1.85 (m, 3H), 2.21 (m, 1H), 2.47 (d, J=13.2 Hz, 2H), 3.37 (d, J=6.8 Hz, 2H), 3.88 (s, 3H), 5.21 (t, J=6.8 Hz, 1H), 6.16 (s, 1H), 6.33 (s, 1H), 6.39 (s, 1H), 11.10 (s, 1H).

Example 136

Preparation of 2-isopentenyl-3-(3',7'-dimethyloctadiene-2',6'-yl)-5-[(E)-styryl]phenol (10o)

Use Compound 8o as material, and follow the method similar to what is described in Example 121 to obtain a white solid as the target product (78%). $^1$H NMR (400 MHz, CDCl$_3$): 1.58 (s, 3H), 1.65 (s, 3H), 1.79 (s, 3H), 2.04 (m, 4H), 3.28 (d, J=6.4 Hz, 2H), 3.89 (s, 3H), 5.10 (t, J=6.4 Hz, 1H), 5.17 (t, J=6.8 Hz, 1H), 6.34 (s, 1H), 6.41 (s, 1H), 6.67 (d, J=16.0 Hz, 1H), 7.22 (t, J=7.6 Hz, 1H), 7.29 (t, J=7.6 Hz, 2H), 7.41 (d, J=7.6 Hz, 2H), 7.78 (d, J=16.0 Hz, 1H), 11.35 (s, 1H).

Example 137

Preparation of 2-isopentenyl-3-methoxy-5-[(E)-2-cyclohexylvinyl]phenol (10p)

Use Compound 8p as material, and follow the method similar to what is described in Example 121 to obtain a white solid as the target product (78%). $^1$H NMR (400 MHz, CDCl$_3$): 1.37 (m, 5H), 1.58 (m, 5H), 1.69 (s, 3H), 1.78 (s, 3H), 2.20 (m, 1H), 335 (d, J=7.2 Hz, 2H), 3.88 (s, 3H), 5.20 (t, J=7.2 Hz, 1H), 6.33 (s, 1H), 6.43 (s, 1H), 6.73 (d, J=16.0 Hz, 1H), 7.21 (d, J=16.0 Hz, 1H), 11.78 (s, 1H).

Example 138

Preparation of 2-isopentenyl-3-methoxy-5-[(E)-4'-hydroxystyryl]-phenol (10q)

Use Compound 8q as material, and follow the method similar to what is described in Example 121 to obtain a white solid as the target product (79%). $^1$H NMR (400 MHz, CDCl$_3$): 1.63 (s, 3H), 1.72 (s, 3H), 3.23 (d, J=7.2 Hz, 2H), 3.88 (s, 3H), 5.20 (t, J=7.2 Hz, 1H), 6.32 (s, 1H), 6.38 (s, 1H), 6.88 (d, J=16.0 Hz, 1H), 7.09 (d, J=8.0 Hz, 2H), 7.31 (d, J=16.0 Hz, 1H), 7.38 (d, J=8.0 Hz, 2H), 11.56 (s, 1H), 11.45 (s, 1H).

Example 139

Preparation of 2-isopentenyl-3-methoxy-5-[(E)-(pyrid-4-yl)ethenyl]phenol (10r)

Use Compound 8r as material, and follow the method similar to what is described in Example 121 to obtain a white solid as the target product (79%). $^1$H NMR (400 MHz, CDCl$_3$): 1.65 (s, 3H), 1.79 (s, 3H), 3.33 (d, J=7.2 Hz, 2H), 3.92 (s, 3H), 5.20 (t, J=7.2 Hz, 1H), 6.34 (s, 1H), 6.42 (s, 1H), 6.80 (d, J=16.0 Hz, 1H), 737 (d, J=16.0 Hz, 1H), 7.58 (d, J=8.0 Hz, 2H), 8.59 (d, J=8.0 Hz, 2H), 11.68 (s, 1H).

Example 140

Preparation of 2-isopentenyl-3-methoxy-4-chloro-5-[(E)-styryl]phenol (10s)

Use Compound 12 as material, and follow the method similar to what is described in Example 121 to obtain a white solid as the target product (73%). $^1$H NMR (400 MHz, CDCl$_3$): 1.71 (s, 3H), 1.82 (s, 3H), 3.43 (d, J=6.8 Hz, 2H), 3.89 (s, 3H), 51 (t, J=6.8 Hz, 1H), 637 (s, 1H), 6.58 (d, J=16.4 Hz, 1H), 7.17 (d, J=16.4 Hz, 1H), 7.34 (t, J=8.0 Hz, 1H), 7.39 (t, J=8.0 Hz, 2H), 7.53 (d, J=8.0 Hz, 2H), 11.32 (s, 1H).

Example 141

Preparation of 2-isopentenyl-3-methoxy-5-[(E)-styryl]anisole (10t)

Use Compound 14 as material, and follow the method similar to what is described in Example 121 to obtain a white solid as the target product (71%). $^1$H NMR (400 MHz, CDCl$_3$): 1.60 (s, 3H), 1.72 (s, 3H), 3.32 (d, J=7.2 Hz, 2H), 3.78 (s, 3H), 3.87 (s, 3H), 5.15 (t, J=7.2 Hz, 1H), 6.33 (s, 1H), 6.41 (s, 1H), 6.88 (d, J=16.0 Hz, 1H), 7.19 (t, J=7.2 Hz, 1H), 7.29 (t, J=7.2 Hz, 2H), 7.43 (d, J=7.2 Hz, 2H), 7.62 (d, J=16.0 Hz, 1H).

Example 142

Preparation of 2-isopentyl-3-methoxy-5-phenethyl phenol (10u)

Use Compound 34 as material, and follow the method similar to what is described in Example 121 to obtain a white solid as the target product (71%). $^1$H NMR (400 MHz, CDCl$_3$): 0.97 (d, J=6.4 Hz, 6H), 1.38 (m, 2H), 1.58 (m, 1H), 2.63 (t, J=7.6 Hz, 2H), 2.93 (t, J=7.6 Hz, 2H), 3.23 (t, J=7.6 Hz, 2H), 3.78 (s, 3H), 6.32 (s, 1H), 6.38 (s, 1H), 7.22 (d, J=7.2 Hz, 2H), 7.35 (m, 3H), 11.64 (s, 1H).

Example 143

Preparation of 2-isopentyl-3-methoxy-5-phenethyl phenol (10v)

Use Compound 36 as material, and follow the method similar to what is described in Example 121 to obtain a white solid as the target product (80%). $^1$H NMR (400 MHz, CDCl$_3$): 138 (s, 3H), 1.68 (s, 3H), 2.81 (t, J=7.6 Hz, 2H), 3.13 (t, J=7.6 Hz, 2H), 3.23 (d, J=6.8 Hz, 2H), 3.88 (s, 3H), 5.16 (t, J=6.8 Hz, 1H), 6.31 (s, 1H), 6.41 (s, 1H), 7.17 (t, J=7.2 Hz, 1H), 7.22 (d, J=7.2 Hz, 2H), 7.28 (t, J=7.2 Hz, 2H), 11.32 (s, 1H).

Example 144

Preparation of 2-isopentyl-3-methoxy-5-[(E)-styryl]phenol (10w)

Use Compound 46 as material, and follow the method similar to what is described in Example 121 to obtain a white solid as the target product (80%). $^1$H NMR (400 MHz, CDCl$_3$): 0.92 (d, J=6.4 Hz, 6H), 1.33 (q, J=7.2 Hz, 2H), 133 (m, 1H), 237 (t, J=7.2 Hz, 2H), 3.91 (s, 3H), 631 (s, 1H), 6.39 (s, 1H), 6.99 (d, J=16.0 Hz, 1H), 72 (t, J=7.6 Hz, 1H), 7.38 (t, J=7.6 Hz, 2H), 7.52 (d, J=7.6 Hz, 2H), 7.82 (d, J=16.0 Hz, 1H), 11.34 (s, 1H).

Example 145

Preparation of 2-isopentenyl-3-methoxy-5-[(E)-2-(pyrid-2-yl)ethenyl]phenol (10x)

Use Compound 1t as material, and follow the method similar to what is described in Example 121 to obtain a white solid as the target product (80%). $^1$H NMR (400 MHz, CDCl$_3$): 1.83 (s, 3H), 1.91 (s, 3H), 3.42 (d, J=8.0 Hz, 2H), 3.80 (s, 3H), 5.21 (t, J=8.0 Hz, 1H), 6.34 (s, 1H), 6.38 (s, 1H), 7.20 (d, J=16.0 Hz, 1H), 731 (d, J=7.6 Hz, 1H), 7.52 (d, J=7.6 Hz, 1H), 7.62 (t, J=7.6 Hz, 1H), 7.82 (d, J=16.6 Hz, 2H), 8.41 (d, J=7.6 Hz, 1H), 11.20 (s, 1H).

Example 146

Preparation of 2-isopentenyl-3-methoxy-5-[(E)-3,4,5-trimethoxystyryl]phenol (10y)

Use Compound 1u as material, and follow the method similar to what is described in Example 121 to obtain a white solid as the target product (80%). $^1$H NMR (400 MHz, CDCl$_3$): 1.85 (s, 3H), 1.92 (s, 3H), 3.32 (d, J=7.6 Hz, 2H), 3.88 (s, 9H), 5.21 (t, J=7.6 Hz, 1H), 6.35 (s, 1H), 6.42 (s, 1H), 7.10 (s, 2H), 7.12 (s, J=16.0 Hz, 1H), 7.25 (t, J=16.0 Hz, 3H), 11.23 (s, 1H).

Example 147

Preparation of 2-isopentenyl-3-methoxy-5-[(E)-2-(4-methoxypyrid-2-yl)ethenyl]phenol (10z)

Use Compound 1v as material, and follow the method similar to what is described in Example 121 to obtain a white solid as the target product (80%). $^1$H NMR (400 MHz, CDCl$_3$): 1.84 (s, 3H), 1.91 (s, 3H), 3.32 (d, J=7.6 Hz, 2H), 3.82 (s, 3H), 3.86 (s, 3H), 5.20 (t, J=7.6 Hz, 1H), 6.32 (s, 1H), 6.35 (s, 1H), 7.04 (s, 1H), 7.15 (d, J=16.0 Hz, 1H), 7.34 (d, J=7.6 Hz, 1H), 7.44 (d, J=16.0 Hz, 1H), 8.32 (d, J=7.6 Hz, 1H), 11.31 (s, 1H).

Example 148

Preparation of 2-isopentenyl-3-methoxy-5-[(E)-2-(4-hydroxypyrid-2-yl)ethenyl]phenol (10a)

Use Compound 1w as material, and follow the method similar to what is described in Example 121 to obtain a white solid as the target product (80%). $^1$H NMR (400 MHz, CDCl$_3$): 1.85 (s, 3H), 1.89 (s, 3H), 3.32 (d, J=7.6 Hz, 2H), 3.86 (s, 3H), 5.22 (t, J=7.6 Hz, 1H), 6.32 (s, 1H), 635 (s, 1H), 7.04 (s, 1H), 7.16 (d, J=16.0 Hz, 1H), 7.32 (d, J=7.6 Hz, 1H), 7.43 (d, J=16.0 Hz, 1H), 8.30 (d, J=7.6 Hz, 1H), 9.89 (s, 1H), 11.31 (s, 1H).

Example 149

Preparation of 2-isopentenyl-3-methoxy-5-[(E)-2-(3-methoxypyrid-2-yl)ethenyl]phenol (10b)

Use Compound 1x as material, and follow the method similar to what is described in Example 121 to obtain a white solid as the target product (80%). ¹H NMR (400 MHz, CDCl₃): 1.84 (s, 3H), 1.85 (s, 3H), 3.34 (d, J=7.6 Hz, 2H), 3.83 (s, 3H), 3.91 (s, 3H), 5.20 (t, J=7.6 Hz, 1H), 635 (s, 1H), 6.40 (s, 1H), 7.16 (d, J=7.6 Hz, 1H), 7.19 (d, J=16.0 Hz, 1H), 7.43 (d, J=7.6 Hz, 1H), 7.50 (d, J=16.0 Hz, 1H), 8.11 (s, 1H), 10.29 (s, 1H).

Example 150

Preparation of 2-isopentenyl-3-methoxy-5-[(E)-2-(3-hydroxypyrid-2-yl)ethenyl]phenol (10c)

Use Compound 1y as material, and follow the method similar to what is described in Example 121 to obtain a white solid as the target product (80%). ¹H NMR (400 MHz, CDCl₃): 1.88 (s, 3H), 1.91 (s, 3H), 3.34 (d, J=7.6 Hz, 2H), 3.91 (s, 3H), 5.22 (t, J=7.6 Hz, 1H), 6.37 (s, 1H), 6.42 (s, 1H), 7.14 (d, J=7.6 Hz, 1H), 7.24 (d, J=16.0 Hz, 1H), 7.46 (d, J=7.6 Hz, 1H), 7.50 (d, J=16.0 Hz, 1H), 8.14 (s, 1H), 9.89 (s, 1H).

Example 151

Preparation of 2-isopentenyl-3-methoxy-5-[(E)-2-(2,4-dimethoxypyrid-2-yl)ethenyl]phenol (10d)

Use Compound 1z as material, and follow the method similar to what is described in Example 121 to obtain a white solid as the target product (80%). ¹H NMR (400 MHz, CDCl₃): 1.87 (s, 3H), 1.96 (s, 3H), 3.35 (d, J=7.6 Hz, 2H), 3.82 (s, 3H), 3.93 (s, 6H), 5.22 (t, J=7.6 Hz, 1H), 6.22 (s, 1H), 6.28 (s, 1H), 6.32 (s, 1H), 638 (s, 1H), 7.19 (d, J=16.0 Hz, 1H), 7.40 (d, J=16.0 Hz, 1H), 10.22 (s, 1H).

Example 152

Preparation of 2-isopentenyl-3-methoxy-5-[(E)-2-(2,4-dihydroxypyrid-2-yl)ethenyl]phenol (10e)

Use Compound 1a as material, and follow the method similar to what is described in Example 121 to obtain a white solid as the target product (80%). ¹H NMR (400 MHz, CDCl₃): 1.88 (s, 3H), 1.97 (s, 3H), 3.36 (d, J=7.6 Hz, 2H), 3.83 (s, 3H), 5.21 (t, J=7.6 Hz, 1H), 6.23 (s, 1H), 6.29 (s, 1H), 6.34 (s, 1H), 6.39 (s, 1H), 7.20 (d, J=16.0 Hz, 1H), 7.43 (d, J=16.0 Hz, 1H), 10.21 (s, 1H).

Example 153

Preparation of 2-isopentenyl-3-methoxy-5-[(E7-2-(2-methoxypyrid-2-yl)ethenyl]phenol (10f)

Use Compound 1b as material, and follow the method similar to what is described in Example 121 to obtain a white solid as the target product (80%). ¹H NMR (400 MHz, CDCl₃): 1.79 (s, 3H), 1.84 (s, 3H), 3.41 (d, J=7.6 Hz, 2H), 3.89 (s, 6H), 5.21 (t, J=7.6 Hz, 1H), 6.55 (d, J=7.2 Hz, 1H), 6.58 (d, J=7.2 Hz, 1H), 6.36 (s, 1H), 6.42 (s, 1H), 7.21 (d, J=16.0 Hz, 1H), 7.36 (t, J=7.6 Hz, 1H), 7.55 (d, J=16.0 Hz, 1H), 10.02 (s, 1H).

Example 154

Preparation of 2-isopentenyl-3-methoxy-5-[(E)-2-(2-hydroxypyrid-2-yl)ethenyl]phenol (10g)

Use Compound 1c as material, and follow the method similar to what is described in Example 121 to obtain a white solid as the target product (80%). ¹H NMR (400 MHz, CDCl₃): 1.79 (s, 3H), 1.84 (s, 3H), 3.41 (d, J=7.6 Hz, 2H), 3.82 (s, 3H), 5.20 (t, J=7.6 Hz, 1H), 6.54 (d, J=7.2 Hz, 1H), 6.57 (d, J=7.2 Hz, 1H), 6.38 (s, 1H), 6.45 (s, 1H), 7.24 (d, J=16.0 Hz, 1H), 7.39 (t, J=7.6 Hz, 1H), 7.52 (d, J=16.0 Hz, 1H), 9.89 (s, 1H).

Example 155

Preparation of 2-allyl-3-methoxy-5-[(E)-styryl]phenol (10h)

Use Compound 1d as material, and follow the method similar to what is described in Example 121 to obtain a white solid as the target product (80%). ¹H NMR (400 MHz, CDCl₃): 3.24 (d, J=7.6 Hz, 2H), 3.77 (s, 3H), 4.91 (dd, J1=16.0 Hz, J2=12.0 Hz, 1H), 4.93 (dd, J1=6.4 Hz, J2=12.0 Hz, 1H), 6.30 (m, 1H), 6.32 (s, 1H), 6.38 (s, 1H), 6.82 (d, J=16.0 Hz, 1H), 7.31 (m, 2H), 7.45 (d, J=7.6 Hz, 2H), 7.51 (t, J=7.6 Hz, 2H), 9.88 (s, 1H).

Example 156

Preparation of methyl 2-hydroxy-4-methoxy-5-chloro-6-[(E)-styryl]benzoate (11)

Dissolve compound 7 (12 g, 0.042 mol) in anhydrous diethyl ether (150 ml), dropwise add in sulfuric chloride (11.2 g, 0.084 mol) at room temperature, when addition finishes, reflux the mixture for 3h, after completion of the reaction, cool the reaction mixture to 0° C., filter out the white solid precipitation to obtain the target product as a white solid (11.4 g, 85%). ¹H NMR (400 MHz, CDCl₃): 3.82 (s, 3H), 3.94 (s, 3H), 6.48 (d, J=16.0 Hz, 1H), 6.52 (s, 1H), 7.20 (d, J=16.0 Hz, 1H), 7.30 (t, J=8.0 Hz, 1H), 7.38 (t, J=8.0 Hz, 2H), 7.50 (d, J=8.0 Hz, 2H), Example 157

Preparation of methyl 2-hydroxy-3-isopentenyl-4-methoxy-5-chloro-6-[(E)-styryl]benzoate (12)

Use Compound 11 as material, and follow the method described in Example 7 to obtain a white solid as the target product (61%). ¹H NMR (400 MHz, CDCl₃): 1.63 (s, 3H), 1.73 (s, 3H), 3.36 (d, J=6.8 Hz, 2H), 3.73 (s, 3H), 3.79 (s, 3H), 5.15 (t, J=6.8 Hz, 1H), 638 (d, J=16.4 Hz, 1H), 7.14 (d, J=16.4 Hz, 1H), 72 (t, J=8.0 Hz, 1H), 7.30 (t, J=8.0 Hz, 2H), 7.41 (d, J=8.0 Hz, 2H), 10.85 (s, 1H).

Example 158

Preparation of 2-hydroxy-3-isopentenyl-4-methoxy-5-chloro-6-[(E)-styryl]benzoic acid (13)

Use Compound 12 as material, and follow the method described in Example 8 to obtain a white solid as the target product (86%). ¹H NMR (400 MHz, CDCl₃): 1.70 (s, 3H), 1.80 (s, 3H), 3.43 (d, J=6.8 Hz, 2H), 3.88 (s, 3H), 5.21 (t, J=6.8 Hz, 1H), 639 (d, J=16.4 Hz, 1H), 7.18 (d, J=16.4 Hz, 1H), 7.33 (t, J=8.0 Hz, 1H), 7.38 (t, J=8.0 Hz, 2H), 7.51 (d, J=8.0 Hz, 2H), 11.32 (s, 1H).

Example 159

Preparation of methyl 2,4-dimethoxy-3-isopentenyl-6-[(E)-styryl]benzoate (14)

Dissolve compound 8 (1.2 g, 3.4 mmol) in DMF (20 ml), add anhydrous $K_2CO_3$ (0.7 g, 5.1 mmol), MeI (0.96 g, 6.8 mmol), react at 60° C. for 2h. After completion of the reaction, cool the mixture, filter and evaporate the DMF from filtrate under reduced pressure, feed the redissolved residue solution to a silica gel column, evaporate the solvent in the eluent to obtain a colorless oil (1.12 g, 90%). $^1$H NMR (400 MHz, DMSO-$d_6$): 1.62 (s, 3H), 1.71 (s, 3H), 3.23 (d, J=6.4 Hz, 2H), 3.68 (s, 3H), 3.86 (s, 3H), 3.90 (s, 3H), 5.10 (t, J=6.4 Hz, 1H), 6.98 (d, J=16.0 Hz, 1H), 7.18 (s, 1H), 7.28 (t, J=7.2 Hz, 1H), 7.30 (d, J=16.0 Hz, 1H), 7.38 (t, J=7.2 Hz, 2H), 7.53 (d, J=7.2 Hz, 2H).

Example 160

Preparation of 2-methoxy-3-isopentenyl-4-methoxy-6-[(E)-styryl]benzoic acid (15)

Use Compound 14 as material, and follow the method similar to what is described in Example 8 to obtain a white solid as the target product (90%). $^1$H NMR (400 MHz, CDCl$_3$): 1.62 (s, 3H), 1.71 (s, 3H), 3.30 (d, J=7.2 Hz, 2H), 3.78 (s, 3H), 3.87 (s, 3H), 5.10 (t, J=7.2 Hz, 1H), 6.88 (d, J=16.0 Hz, 1H), 6.90 (s, 1H), 7.18 (t, J=7.2 Hz, 1H), 78 (t, J=7.2 Hz, 2H), 7.46 (d, J=7.2 Hz, 2H), 7.60 (d, J=16.0 Hz, 1H).

Example 161

Preparation of methyl 2,4-dimethoxy-5-bromo-6-[(E)-styryl]benzoate (16)

Dissolve compound 6 (13.0 g, 0.046 mol) CH$_2$Cl$_2$ (150 ml), add bromine (8.1 g, 0.050 mol) dropwise at room temperature, react at room temperature for 1 h, after completion of the reaction, wash the organic layer successively with water, saturated NaHCO$_3$ solution and brine, dry the organic solution over anhydrous MgSO$_4$. Filter the solution and evaporate the solvent, redissolve the residue, feed the solution to a silica gel column, evaporate the solvent in the eluent to obtain a white solid (15.1 g, 87%). $^1$H NMR (400 MHz, CDCl$_3$): 3.80 (s, 3H), 3.86 (s, 3H), 3.93 (s, 3H), 639 (d, J=15.6 Hz, 1H), 6.50 (s, 1H), 70 (d, J=15.6 Hz, 1H), 7.29 (t, J=7.6 Hz, 1H), 7.37 (t, J=7.6 Hz, 2H), 7.49 (d, J=7.6 Hz, 2H).

Example 162

Preparation of methyl 2,4-dimethoxy-5-isopentenyl-6-[(E)-styryl]benzoate (17)

Dissolve compound 16 (2.0 g, 5.30 mmol) in DMF (30 ml), add in Pd(OAc)$_2$ (0.12 g, 0.53 mmol), PPh3 (0.56 g, 2.12 mmol) and triisopentenyl tin (2.3 g, 6.36 mmol), heat the mixture to 100° C. to react for 12h. After completion of the reaction, distill off the solvent, redissolve the residue and feed the solution to a silica gel column, evaporate the solvent in the eluent to obtain a colorless oily liquid (1.5 g, 80%). $^1$H NMR (400 MHz, CDCl$_3$): 1.59 (s, 3H), 1.61 (s, 3H), 3.25 (6.4 Hz), 3.68 (s, 3H), 3.80 (s, 6H), 5.01 (t, J=6.4 Hz, 1H), 637 (s, 1H), 6.57 (d, J=16.0 Hz, 1H), 7.07 (d, J=16.0 Hz, 1H), 7.18 (t, J=8.0 Hz, 1H), 7.24 (t, J=8.0 Hz, 2H), 7.35 (d, J=8.0 Hz, 2H).

Example 163

Preparation of methyl 2-hydroxy-4-methoxy-5-isopentenyl-6-[(E)-styryl]benzoate (18)

Use Compound 17 as material, and follow the method described in Example 6 to obtain a white solid as the target product (86%). $^1$H NMR (400 MHz, DMSO-$d_6$): 1.59 (s, 6H), 3.22 (d, 6.4 Hz, 2H), 3.62 (s, 3H), 3.76 (s, 3H), 4.99 (t, J=6.4 Hz, 1H), 6.43 (d, J=16.0 Hz, 1H), 6.47 (s, 1H), 7.19 (d, J=16.0 Hz, 1H), 7.26 (t, J=8.0 Hz, 1H), 7.36 (t, J=8.0 Hz, 2H), 7.46 (d, J=8.0 Hz, 2H).

Example 164

Preparation of 3-methoxy-4-isopentenyl-5-[(E)-styryl]phenol (19, cajanine C)

Use Compound 18 as material, and follow the method described in Example 87 to obtain a white solid as the target product (78%). $^1$H NMR (400 MHz, DMSO-$d_6$): 1.59 (s, 3H), 1.72 (s, 3H), 3.20 (d, 7.2 Hz, 2H), 3.72 (s, 3H), 4.98 (t, J=7.2 Hz, 1H), 6.34 (d, J=2.0 Hz, 1H), 6.64 (d, J=2.0 Hz, 1H), 6.94 (d, J=16.0 Hz, 1H), 7.26 (t, J=8.0 Hz, 1H), 7.30 (d, J=16.0 Hz, 1H), 7.36 (t, J=8.0 Hz, 2H), 7.54 (d, J=8.0 Hz, 2H), 9.25 (s, 1H).

Example 165

Preparation of 2,2-dimethyl-5-methoxy-7-[(E)-styryl]benzotetrahydropyran (20)

Dissolve cajanine 1 (0.5 g, 1.48 mmol) in dichloromethane (20 ml), add dropwise trimethylsilyl iodide (0.59 g, 2.96 mmol) at room temperature, react at room temperature for 3h, after completion of the reaction, add methanol (10 ml), stir for 0.5h. Distill off the solvent, and redissove the residue, feed the solution to a silica gel column, evaporate the solvent in the eluent to obtain a colorless oily liquid (0.33 g, 78%). $^1$H NMR (400 MHz, DMSO-$d_6$): 15 (s, 6H), 1.72 (t, J=6.8 Hz, 2H), 2.54 (t, J=6.8 Hz, 2H), 3.82 (s, 3H), 6.70 (d, J=15.6 Hz, 1H), 7.10 (d, J=15.6 Hz, 1H), 7.18 (s, 1H), 7.24 (t, J=7.6 Hz, 1H), 7.36 (t, J=7.6 Hz, 2H), 7.55 (d, J=7.6 Hz, 2H).

Example 166

Preparation of 1,3-dimethoxy-5-[(E)-3-phenylpropen-1-yl]benzene (21a)

Use diethyl 3,5-dimethoxybenzyl phosphate and phenylacetaldehyde as materials, and follow the method described in Example 5 to obtain a pale yellow solid as the target product (78%). $^1$H NMR (400 MHz, DMSO-$d_6$): 3.22 (d, J=7.6 Hz, 2H), 3.79 (s, 6H), 6.25 (s, 1H), 6.34 (d, J=16.0 Hz, 1H), 6.66 (m, 1H), 6.72 (s, 2H), 7.16 (m, 3H), 7.27 (m, 2H).

Example 167

Preparation of 1,3-dihydroxy-5-[(E)-3-phenylpropen-1-yl]benzene (21b)

Use compound 21a as material, and follow the method described in Example 6 to obtain a white solid as the target product (80%). $^1$H NMR (400 MHz, DMSO-$d_6$): 3.25 (d, J=7.6 Hz, 2H), 6.21 (s, 1H), 6.35 (d, J=16.0 Hz, 1H), 6.67 (m, 1H), 6.74 (s, 2H), 7.18 (m, 3H), 7.24 (m, 2H), 9.82 (s, 1H), 10.02 (s, 1H).

Example 168

Preparation of 1,3-dimethoxy-5-[(E)-3-acetoxy-4-methoxystyryl]benzene (21c)

Use diethyl 3,5-dimethoxybenzyl phosphonate and 3-Acetoxy-4-methoxybenzaldehyde as materials follow the method described in Example 5 to obtain a pale yellow solid as the product (79%). $^1$H NMR (400 MHz, DMSO-$d_6$): 2.08 (s, 3H), 3.73 (s, 3H), 3.80 (s, 6H), 6.23 (s, 1H), 6.84 (s, 2H), 6.92 (d, J=16.0 Hz, 1H), 6.99 (d, J=16.0 Hz, 1H), 7.07 (d, J=7.6 Hz, 1H), 7.12 (d, J=7.6 Hz, 1H), 7.14 (s, 1H).

Example 169

Preparation of 1,3-dimethoxy-5-[(E)-3-hydroxy-4-methoxy-styryl]benzene (21d)

Dissolve compound 21c (5.0 g, 0.015 mol) in anhydrous methanol (50 ml), add in sodium methoxide (1.41 g, 0.024 mol), reflux to react for 3h, after completion of the reaction, pour the reaction solution into ice water, adjust pH to less than 2 with dilute hydrochloric acid, extract three times with ethyl acetate, pool the organic layer, dry the solution over anhydrous magnesium sulfate. Filter, and evaporate the solvent in the solution, redissolve the residue with petroleum ether/ethyl acetate, recrystallize to obtained a white solid (3.70 g, 85%). $^1$H NMR (400 MHz, DMSO-$d_6$): 3.75 (s, 3H), 3.81 (s, 6H), 6.24 (s, 1H), 6.86 (s, 2H), 6.93 (d, J=16.0 Hz, 1H), 7.01 (d, J=16.0 Hz, $^1$H), 7.08 (d, J=7.6 Hz, 1H), 7.13 (d, J=7.6 Hz, 1H), 7.15 (s, 1H), 9.89 (s, 1H).

Example 170

Preparation of 1,3-dihydroxy-5-[(E)-3,4-dihydroxystyryl]benzene (21E)

Use compound 21d as material, and follow the method described in Example 6 to obtain a white solid as the target product (75%). $^1$H NMR (400 MHz, DMSO-$d_6$): 6.24 (s, 1H), 6.87 (s, 2H), 6.94 (d, J=16.0 Hz, 1H), 7.03 (d, J=16.0 Hz, 1H), 7.09 (d, J=7.6 Hz, 1H), 7.15 (d, J=7.6 Hz, 1H), 7.18 (s, 1H), 9.89 (s, 3H), 10.02 (s, 1H).

Example 171

Preparation of 1,3-dimethoxy-5-[(E)-2-(3,5-diacetoxyphenyl)propen-1-yl]benzene (21f)

Use diethyl 3,5-dimethoxybenzyl phosphate and 3,4-diacetoxybenzaldehyde as materials, and follow the method described in Example 5 to obtain a white solid as the target product (74%). $^1$H NMR (400 MHz, DMSO-$d_6$): 1.72 (s, 3H), 2.06 (s, 3H), 2.08 (s, 3H), 3.78 (s, 6H), 6.22 (s, 1H), 6.71 (s, 1H), 6.84 (s, 2H), 7.04 (s, 2H), 7.15 (s, 1H).

Example 172

Preparation of 1,3-dimethoxy-5-[(E)-2-(3,5-dihydroxyphenyl)propen-1-yl]benzene (21g)

Use compound 21f as material, and follow the method described in Example 169 to obtain the target product (90%). $^1$H NMR (400 MHz, DMSO-$d_6$): 1.73 (s, 3H), 3.75 (s, 6H), 6.21 (s, 1H), 6.72 (s, 1H), 6.83 (s, 2H), 7.06 (s, 2H), 7.13 (s, 1H), 9.87 (s, 1H), 9.98 (s, 1H).

Example 173

Preparation of 1,3-dihydroxy-5-[(E)-2-(3,5-dihydroxyphenyl)propen-1-yl]benzene (21h)

Use compound 21 g as material, and follow the method described in Example 6 to obtain a white solid as the target product (78%). $^1$H NMR (400 MHz, DMSO-$d_6$): 1.75 (s, 3H), 6.23 (s, 1H), 6.77 (s, 1H), 6.85 (s, 2H), 7.01 (s, 2H), 7.12 (s, 1H), 9.89 (s, 2H), 10.02 (s, 2H).

Example 174

Preparation of 1,3-dimethoxy-5-[(E)-3,4,5-triacetoxystyryl]benzene (21i)

Use diethyl 3,5-dimethoxybenzyl phosphate and 3,4,5-triacetoxybenzaldehyde as materials, and follow the method described in Example 5 to obtain a white solid as the target product (75%). $^1$H NMR (400 MHz, DMSO-$d_6$): 2.08 (s, 9H), 3.77 (s, 6H), 6.22 (s, 1H), 6.84 (s, 2H), 6.91 (d, J=16.0 Hz, 1H), 6.92 (d, J=16.0 Hz, $^1$H), 7.01 (s, 2H).

Example 175

Preparation of 1,3-dimethoxy-5-[(E)-3,4,5-trihydroxystyryl]benzene (21j)

Use compound 21i as material, and follow the method described in Example 169 to obtain a white solid as the target product (88%). $^1$H NMR (400 MHz, DMSO-$d_6$): 3.78 (s, 6H), 6.21 (s, 1H), 6.85 (s, 2H), 6.90 (d, J=16.0 Hz, 1H), 6.92 (d, J=16.0 Hz, 1H), 7.02 (s, 2H), 9.89 (s, 1H), 9.92 (s, 2H).

Example 176

Preparation of 1,3-dihydroxy-5-[(E)-3,4,5-trihydroxystyryl]benzene (21k)

Use compound 21j as material, and follow the method described in Example 6 to obtain a white solid as the target product (75%). $^1$H NMR (400 MHz, DMSO-$d_6$): 6.24 (s, 1H), 6.83 (s, 2H), 6.91 (d, J=16.0 Hz, 1H), 6.93 (d, J=16.0 Hz, 1H), 7.05 (s, 2H), 9.89 (s, 1H), 9.92 (s, 2H), 10.02 (s, 2H).

Example 177

Preparation of (E)-(2-hydroxy-3-isopentenyl-4-methoxy-6-styryl phenyl)(1H-imidazol-1-yl)ketone (22)

Dissolve cajanine (1.0 g, 2.96 mmol) in chloroform (20 ml), add $CaCl_2$ (0.39 g, 3.55 mmol) and carbonyldiimidazole (0.58 g, 3.56 mmol), react at room temperature for 4-6h, after completion of the reaction, wash the organic layer with dilute hydrochloric acid and saturated brine successively, dry over anhydrous magnesium sulfate, filter and distill off the solvent in the solution. Redissolve the residue and feed the solution to silica gel column, evaporate the solvent in the eluent to obtain a white solid as the desired product (1.0 g, 87%). $^1$H NMR (400 MHz, DMSO-$d_6$): 1.78 (s, 3H), 1.85 (s, 3H), 3.22 (d, J=7.6 Hz, 2H), 3.78 (s, 3H), 51 (t, J=7.6 Hz, 1H), 6.70 (s, 1H), 6.82 (d, J=16.0 Hz, 1H), 78 (d, J=16.0 Hz, 1H), 7.30 (m, 2H), 7.42 (d, J=7.6 Hz, 2H), 7.44 (t, J=7.6 Hz, 2H), 7.70 (d, J=8.0 Hz, 1H), 8.27 (s, 1H), 9.98 (s, 1H).

Example 178

Preparation of N-aminoformyl-2-hydroxy-3-isopentenyl-4-methoxy-6-[(E)-styryl]benzamide (23a)

Dissolve compound 8 (1.0 g, 2.96 mmol) in anhydrous ethanol (20 ml), add in urea (0.27 g, 4.44 mmol), reflux to react for 12h, after completion of the reaction, pour the solution into ice water and extract three times with ethyl acetate, pool the organic layer, dry over anhydrous magnesium sulfate, filter and concentrate the solution, feed the solution to a silica gel column, evaporate the solvent in the eluent to obtain a white solid as the desired product (0.89 g, 80%). $^1$H NMR (400 MHz, DMSO-$d_6$): 1.79 (s, 3H), 1.82 (s, 3H), 3.34 (d, J=7.6 Hz, 2H), 3.83 (s, 3H), 5.21 (t, J=7.6 Hz, 1H), 6.20 (s, 2H), 6.65 (s, 1H), 6.81 (d, J=16.0 Hz, 1H), 7.26 (d, J=16.0 Hz, 1H), 7.32 (d, J=7.6 Hz, 1H), 7.43 (d, J=7.6 Hz, 2H), 7.45 (t, J=7.6 Hz, 2H), 9.89 (s, 1H), 11.77 (s, 1H).

Example 179

Preparation of N-amidino-2-hydroxy-3-isopentenyl-4-methoxy-6-[(E)-styryl]benzamide (23b)

Use compound 9 and guanidine as materials, and follow the method described in Example 178 to obtain a white solid as the target product (80%). $^1$H NMR (400 MHz, DMSO-$d_6$): 1.78 (s, 3H), 1.81 (s, 3H), 3.32 (d, J=7.6 Hz, 2H), 3.79 (s, 3H), 50 (t, J=7.6 Hz, 1H), 532 (s, 1H), 6.45 (s, 2H), 6.69 (s, 1H), 6.80 (d, J=16.0 Hz, 1H), 7.27 (d, J=16.0 Hz, 1H), 7.30 (d, J=7.6 Hz, 1H), 7.38 (d, J=7.6 Hz, 2H), 7.42 (t, J=7.6 Hz, 2H), 8.23 (s, 1H), 9.89 (s, 1H).

Example 180

Preparation of 2-aminoacetoxy-3-isopentenyl-4-methoxy-6-[(E)-styryl]benzoate (24a)

Dissolve compound 8 (1.5 g, 4.26 mmol) and triethylamine (1.3 g, 12.8 mmol) in dichloromethane, add dropwise acetyl chloride solution in dichloromethane at 0° C. (prepared from aminoacetic acid (0.48 g, 6.39 mmol) and thionyl chloride), after completion of addition, react at room temperature for 8-10 h until completion. Wash the organic layer successively with water, dilute hydrochloric acid, and saturated brine, dry the organic solution over anhydrous magnesium sulfate, filter and concentrate the solution, and feed the residue to silica gel column, evaporate the solvent in the eluent to obtain a white solid as the target product (1.36 g, 78%). $^1$H NMR (400 MHz, DMSO-$d_6$): 1.78 (s, 3H), 1.81 (s, 3H), 332 (d, J=7.6 Hz, 2H), 3.59 (s, 2H), 3.73 (s, 3H), 3.88 (s, 3H), 5.12 (s, 2H), 5.20 (t, J=7.6 Hz, 1H), 6.72 (s, 1H), 6.82 (d, J=16.0 Hz, 1H), 7.26 (d, J=16.0 Hz, 1H), 732 (d, J=7.6 Hz, 1H), 7.42 (d, J=7.6 Hz, 2H), 7.48 (t, J=7.6 Hz, 2H).

Example 181

Preparation of 2-Aminoacetoxy-3-isopentenyl-4-methoxy-6-[(E)-styryl]benzoic acid (24b)

Use compound 1 as material, and follow the method described in Example 180 to obtain a white solid as the target product (80%). $^1$H NMR (400 MHz, DMSO-$d_6$): 1.79 (s, 3H), 1.83 (s, 3H), 3.33 (d, J=7.6 Hz, 2H), 3.57 (s, 2H), 3.78 (s, 3H), 5.11 (s, 2H), 5.22 (t, J=7.6 Hz, 1H), 6.73 (s, 1H), 6.80 (d, J=16.0 Hz, 1H), 7.26 (d, J=16.0 Hz, 1H), 733 (d, J=7.6 Hz, 1H), 7.43 (d, J=7.6 Hz, 2H), 7.45 (t, J=7.6 Hz, 2H), 12.32 (s, 1H).

Example 182

Preparation of 2-isopentenyl-3-aminoacetoxy-5-[(E)styryl]anisole (24c)

Use compound 10 as material, and follow the method described in Example 180 to obtain a white solid as the target product (79%). $^1$H NMR (400 MHz, DMSO-$d_6$): 1.80 (s, 3H), 1.84 (s, 3H), 3.34 (d, J=7.6 Hz, 2H), 3.59 (s, 2H), 3.76 (s, 3H), 5.13 (s, 2H), 5.21 (t, J=7.6 Hz, 1H), 6.36 (s, 1H), 6.39 (s, 1H), 6.81 (d, J=16.0 Hz, 1H), 7.24 (d, J=16.0 Hz, 1H), 7.32 (d, J=7.6 Hz, 1H), 7.43 (d, J=7.6 Hz, 2H), 7.49 (t, J=7.6 Hz, 2H).

Example 183

Preparation of 2-(pyrrol-2-carboxamido)-3-isopentenyl-4-methoxy-6-[(E)-styryl]benzoate (24d)

Use compound 8 and pyrrolyl-2-carbonyl chloride as materials, and follow the method described in Example 180 to obtain a white solid as the target product (78%). 1H NMR (400 MHz, DMSO-$d_6$): 1.62 (m, 2H), 1.78 (m, 2H), 1.80 (s, 3H), 1.84 (s, 3H), 2.78 (m, 2H), 3.34 (d, J=7.6 Hz, 2H), 3.58 (m, 1H), 3.78 (s, 3H), 3.88 (s, 3H), 4.56 (s, 1H), 5.21 (t, J=7.6 Hz, 1H), 6.73 (s, 1H), 6.81 (d, J=16.0 Hz, 1H), 7.27 (d, J=16.0 Hz, 1H), 7.45 (m, 5H).

Example 184

Preparation of 2-(pyrrol-2-carboxamido)-3-isopentenyl-4-methoxy-6-[(E)-styryl]benzoic acid (24e)

Use compound 1 and pyrrolyl-2-carbonyl chloride as materials, and follow the method described in Example 180 to obtain a white solid as the target product (81%). $^1$H NMR (400 MHz, DMSO-$d_6$): 1.68 (m, 2H), 1.75 (m, 2H), 1.79 (s, 3H), 1.83 (s, 3H), 2.80 (m, 2H), 3.32 (d, J=7.6 Hz, 2H), 3.59 (m, 1H), 3.78 (s, 3H), 4.53 (s, 1H), 5.22 (t, J=7.6 Hz, 1H), 6.72 (s, 1H), 6.79 (d, J=16.0 Hz, 1H), 7.29 (d, J=16.0 Hz, 1H), 7.45 (m, 5H), 12.21 (s, 1H).

Example 185

Preparation of 2-isopentenyl-3-(pyrrol-2-formyloxy)-5-[(E)-styryl]anisole (24f)

Use compound 10 and pyrrolyl-2-carbonyl chloride as materials, and follow the method described in Example 180 to obtain a white solid as the target product (85%). $^1$H NMR (400 MHz, DMSO-$d_6$): 1.69 (m, 2H), 1.74 (m, 2H), 1.79 (s, 3H), 1.83 (s, 3H), 2.82 (m, 2H), 3.22 (d, J=7.6 Hz, 2H), 3.54 (m, 1H), 3.78 (s, 3H), 4.52 (s, 1H), 5.23 (t, J=7.6 Hz, 1H), 6.35 (s, 1H), 6.41 (s, 1H), 6.79 (d, J=16.0 Hz, 1H), 7.27 (d, J=16.0 Hz, 1H), 7.45 (m, 5H).

Example 186

Preparation of methyl 2-acetoxy-3-isopentenyl-4-methoxy-6-[(E)-styryl]benzoate (24g)

Use compound 8 and acetyl chloride as materials, and follow the method described in Example 180 to obtain a white solid as the target product (82%). 1H NMR (400 MHz, DMSO-d$_6$): 1.79 (s, 3H), 1.83 (s, 3H), 2.08 (s, 3H), 332 (d, J=7.6 Hz, 2H), 3.73 (s, 3H), 3.89 (s, 3H), 5.23 (t, J=7.6 Hz, 1H), 6.72 (s, 1H), 6.79 (d, J=16.0 Hz, 1H), 719 (d, J=16.0 Hz, 1H), 7.30 (d, J=7.6 Hz, 1H), 7.43 (d, J=7.6 Hz, 2H), 7.45 (t, J=7.6 Hz, 2H).

Example 187

Preparation of 2-(pyrrol-2-formyloxy)-3-isopentenyl-4-methoxy-6-[(E)-styryl]benzoic acid (24h)

Use compound 9 and acetyl chloride as material, and follow the method described in Example 180 to obtain a white solid as the target product (85%). $^1$H NMR (400 MHz, DMSO-d$_6$): 1.77 (s, 3H), 1.85 (s, 3H), 2.07 (s, 3H), 334 (d, J=7.6 Hz, 2H), 3.78 (s, 3H), 5.25 (t, J=7.6 Hz, 1H), 6.70 (s, 1H), 6.79 (d, J=16.0 Hz, 1H), 78 (d, J=16.0 Hz, 1H), 7.32 (d, J=7.6 Hz, 1H), 7.45 (d, J=7.6 Hz, 2H), 7.49 (t, J=7.6 Hz, 2H), 12.54 (s, 1H).

Example 188

Preparation of 2-isopentenyl-3-(pyrrol-2-formyloxy)-5-[(E)-styryl]anisole (24i)

Use compound 10 and acetyl chloride as materials, and follow the method described in Example 180 to obtain a white solid as the target product (87%). $^1$H NMR (400 MHz, DMSO-d$_6$): 1.79 (s, 3H), 1.83 (s, 3H), 2.08 (s, 3H), 3.38 (d, J=7.6 Hz, 2H), 3.78 (s, 3H), 5.23 (t, J=7.6 Hz, 1H), 6.37 (s, 1H), 6.40 (s, 1H), 6.78 (d, J=16.0 Hz, 1H), 7.27 (d, J=16.0 Hz, 1H), 7.31 (d, J=7.6 Hz, 1H), 7.43 (d, J=7.6 Hz, 2H), 7.48 (t, J=7.6 Hz, 2H).

Example 189

Preparation of 2-(pyridyl-3-formylox)-3-isopentenyl-4-methoxy-6-[(E)-styryl]-benzoate (24j)

Use compound 8 and pyridyl-3-carbonylchloride as materials, and follow the method described in Example 180 to obtain a white solid as the target product (86%). 1H NMR (400 MHz, DMSO-d$_6$): 1.78 (s, 3H), 1.83 (s, 3H), 3.34 (d, J=7.6 Hz, 2H), 3.78 (s, 3H), 3.89 (s, 3H), 5.23 (t, J=7.6 Hz, 1H), 6.70 (s, 1H), 6.78 (d, J=16.0 Hz, 1H), 7.27 (d, J=16.0 Hz, 1H), 7.31 (d, J=7.6 Hz, 1H), 7.43 (d, J=7.6 Hz, 2H), 7.48 (m, 3H), 8.17 (d, J=8.0 Hz, 1H), 8.71 (d, J=8.0 Hz, 1H), 9.04 (s, 1H).

Example 190

Preparation of 2-(pyridyl-3-formylox)-3-isopentenyl-4-methoxy-6-[(E)-styryl]benzoic acid (24k)

Use compound 1 and pyridyl-3-carbonyl chloride as materials, and follow the method described in Example 180 to obtain a white solid as the target product (84%). $^1$H NMR (400 MHz, DMSO-d$_6$): 1.79 (s, 3H), 1.84 (s, 3H), 3.35 (d, J=7.6 Hz, 2H), 3.78 (s, 3H), 5.22 (t, J=7.6 Hz, 1H), 6.72 (s, 1H), 6.79 (d, J=16.0 Hz, 1H), 732 (d, J=16.0 Hz, 1H), 7.28 (d, J=16.0 Hz, 1H), 7.44 (d, J=7.6 Hz, 2H), 7.47 (m, 3H), 8.16 (d, J=8.0 Hz, 1H), 8.73 (d, J=8.0 Hz, 1H), 9.08 (s, 1H), 12.32 (s, 1H).

Example 191

Preparation of 2-isopentenyl-3-(pyridyl-3-formyloxy)-5-[(E)-styryl]anisole (24l)

Use compound 10 and pyridyl-3-carbonyl chloride as materials, and follow the method described in Example 180 to obtain a white solid as the target product (87%). $^1$H NMR (400 MHz, DMSO-d$_6$): 1.77 (s, 3H), 1.82 (s, 3H), 3.32 (d, J=7.6 Hz, 2H), 3.73 (s, 3H), 5.28 (t, J=7.6 Hz, 1H), 631 (s, 1H), 6.35 (s, 1H), 6.79 (d, J=16.0 Hz, 1H), 7.27 (d, J=16.0 Hz, 1H), 730 (d, J=7.6 Hz, 1H), 7.42 (d, J=7.6 Hz, 2H), 7.45 (m, 3H), 8.14 (d, J=8.0 Hz, 1H), 8.71 (d, J=8.0 Hz, 1H), 9.03 (s, 1H).

Example 192

Preparation of 2-(N,N-dimethylacetyloxy)-3-isopentenyl-4-methoxy-6-[(E)-styryl]benzoate (24m)

Use compound 8 and N,N-dimethylacetyl chloride as materials, and follow the method described in Example 180 to obtain a white solid as the target product (79%). $^1$H NMR (400 MHz, DMSO-d$_6$): 1.71 (s, 3H), 1.79 (s, 3H), 2.27 (s, 6H), 3.30 (s, 2H), 3.35 (d, J=7.6 Hz, 2H), 3.73 (s, 3H), 3.87 (s, 3H), 5.28 (t, J=7.6 Hz, 1H), 6.73 (s, 1H), 6.80 (d, J=16.0 Hz, 1H), 7.27 (d, J=16.0 Hz, 1H), 7.30 (d, J=7.6 Hz, 1H), 7.42 (d, J=7.6 Hz, 2H), 7.45 (t, J=7.6 Hz, 2H).

Example 193

Preparation of 2-(N,N-dimethylacetyloxy)-3-isopentenyl-4-methoxy-6-[(E)-styryl]benzoic acid (24n)

Use compound 1 and N,N-dimethylacetyl chloride as materials, and follow the method described in Example 180 to obtain a white solid as the target product (85%). $^1$H NMR (400 MHz, DMSO-d$_6$): 1.77 (s, 3H), 1.82 (s, 3H), 2.28 (s, 6H), 3.31 (s, 2H), 3.35 (d, J=7.6 Hz, 2H), 3.73 (s, 3H), 5.23 (t, J=7.6 Hz, 1H), 6.70 (s, 1H), 6.80 (d, J=16.0 Hz, 1H), 7.26 (d, J=16.0 Hz, 1H), 7.31 (d, J=7.6 Hz, 1H), 7.43 (d, J=7.6 Hz, 2H), 7.47 (t, J=7.6 Hz, 2H), 12.32 (s, 1H).

Example 194

Preparation of 2-isopentenyl-3-(N,N-dimethylacetoxy)-5-[(E)-styryl]anisole (24o)

Use compound 10 and N,N-dimethylacetyl chloride as materials, and follow the method described in Example 180 to obtain a white solid as the target product (86%). $^1$H NMR (400 MHz, DMSO-d$_6$): 1.79 (s, 3H), 1.83 (s, 3H), 2.25 (s, 6H), 3.29 (s, 2H), 3.34 (d, J=7.6 Hz, 2H), 3.75 (s, 3H), 5.26 (t, J=7.6 Hz, 1H), 6.41 (s, 1H), 6.45 (s, 1H), 6.81 (d, J=16.0 Hz, 1H), 7.27 (d, J=16.0 Hz, 1H), 7.30 (d, J=7.6 Hz, 1H), 7.42 (d, J=7.6 Hz, 2H), 7.45 (t, J=7.6 Hz, 2H).

Example 195

Preparation of methyl 2-(1H-imidazol-2-formylox)-3-isopentenyl-4-methoxy-6-[(E)-styryl]benzoate (24p)

Use compound 8 and 1H-imidazole-2-acetyl chloride as materials, and follow the method described in Example 180 to obtain a white solid as the target product (82%). $^1$H NMR (400 MHz, DMSO-d$_6$): 1.78 (s, 3H), 1.83 (s, 3H), 32 (d, J=7.6

Hz, 2H), 3.75 (s, 3H), 3.87 (s, 3H), 5.21 (t, J=7.6 Hz, 1H), 6.72 (s, 1H), 6.82 (d, J=16.0 Hz, 1H), 76 (d, J=16.0 Hz, 1H), 7.31 (d, J=7.6 Hz, 1H), 7.43 (d, J=7.6 Hz, 2H), 7.47 (t, J=7.6 Hz, 2H), 8.06 (s, 1H), 8.34 (s, 1H), 9.21 (s, 1H).

Example 196

Preparation of 2-(1H-imidazolyl-2-formylox)-3-isopentenyl-4-methoxy-6-[(E)-styryl]benzoic acid (24q)

Use compound 1 and 1H-imidazolyl-2-acetyl chloride as materials, and follow the method described in Example 180 to obtain a white solid as the target product (85%). $^1$H NMR (400 MHz, DMSO-$d_6$): 1.79 (s, 3H), 1.83 (s, 3H), 36 (d, J=7.6 Hz, 2H), 3.75 (s, 3H), 5.23 (t, J=7.6 Hz, 1H), 6.70 (s, 1H), 6.80 (d, J=16.0 Hz, 1H), 74 (d, J=16.0 Hz, 1H), 7.30 (d, J=7.6 Hz, 1H), 7.42 (d, J=7.6 Hz, 2H), 7.45 (t, J=7.6 Hz, 2H), 8.06 (s, 1H), 8.32 (s, 1H), 8.98 (s, 1H), 12.32 (s, 1H).

Example 197

Preparation of 2-isopentenyl-3-(1H-imidazolyl-2-formyloxy)-5-[(E)-styryl]anisole (24r)

Use compound 10 and 1H-imidazolyl-2-acetyl chloride as materials, and follow the method described in Example 180 to obtain a white solid as the target product (79%). $^1$H NMR (400 MHz, DMSO-$d_6$): 1.78 (s, 3H), 1.82 (s, 3H), 3.25 (d, J=7.6 Hz, 2H), 3.73 (s, 3H), 5.20 (t, J=7.6 Hz, 1H), 6.32 (s, 1H), 6.38 (s, 1H), 6.80 (d, J=16.0 Hz, 1H), 7.25 (d, J=16.0 Hz, 1H), 7.31 (d, J=7.6 Hz, 1H), 7.43 (d, J=7.6 Hz, 2H), 7.47 (t, J=7.6 Hz, 2H), 8.07 (s, 1H), 8.35 (s, 1H), 9.02 (s, 1H).

Example 198

Preparation of methyl 2-(N-benzylaminomethoxy)-3-isopentenyl-4-methoxy-6-[(E)-styryl]benzoate (25a)

Dissolve compound 8 (1.0 g, 2.84 mmol), N-benzyl methanolamine (0.50 g, 3.70 mmol), triphenylphosphine (0.97 g, 3.70 mmol) in dry THF (40 ml), Add DEAD (0.6 g, 3.70 mmol) solution in THF dropwise at 0° C. dropwise. After completing the addition, react at room temperature for 4-6 hours, after completion of the reaction, pour the reaction mixture into saturated brine, extract with ethyl acetate, pool the organic layer and dry over anhydrous magnesium sulfate, filter and concentrate the organic solution, feed the residual solution to a silica gel column, evaporate the solvent in the eluent to obtain a white solid as the target product (1.04 g, 78%). $^1$H NMR (400 MHz, DMSO-$d_6$): 1.78 (s, 3H), 1.82 (s, 3H), 32 (d, J=7.6 Hz, 2H), 3.75 (s, 3H), 3.81 (s, 2H), 3.88 (s, 3H), 4.56 (s, 1H), 51 (t, J=7.6 Hz, 1H), 5.30 (s, 2H), 6.50 (s, 1H), 6.82 (d, J=16.0 Hz, 1H), 7.28 (d, J=16.0 Hz, 1H), 7.32 (m, 6H), 7.45 (m, 4H).

Example 199

Preparation of 2-aminomethoxy-3-isopentenyl-4-methoxy-6-[(E)-styryl]-benzoate (26a)

Dissolve compound 25a (1.0 g, 2.12 mmol) in ethanol (20 ml), add in zinc powder (0.42 g, 6.36 mmol) and ammonium formate (0.20 g, 3.18 mmol), stir the reaction mixture at room temperature for 10h, after completion of the reaction, filter out the insoluble, concentrate the filtrate, feed the filtrate to a chromatographic column, evaporate the solvent in the eluent to obtain a white solid as the product (0.73 g, 90%). $^1$H NMR (400 MHz, DMSO-$d_6$): 1.77 (s, 3H), 1.82 (s, 3H), 3.26 (d, J=7.6 Hz, 2H), 3.75 (s, 3H), 3.89 (s, 3H), 4.21 (s, 2H), 5.21 (t, J=7.6 Hz, 1H), 530 (s, 2H), 6.50 (s, 1H), 6.80 (d, J=16.0 Hz, 1H), 7.26 (d, J=16.0 Hz, 1H), 730 (t, J=7.6 Hz, 1H), 7.42 (d, J=7.6 Hz, 2H), 7.45 (t, J=7.6 Hz, 2H).

Example 200

Preparation of 2-aminomethoxy-3-isopentenyl-4-methoxy-6-[(E)-styryl]benzoic acid (26b)

Use compound 26a as material, and follow the method described in Example 8 to obtain a white solid as the target product (80%). $^1$H NMR (400 MHz, DMSO-$d_6$): 1.78 (s, 3H), 1.81 (s, 3H), 3.22 (d, J=7.6 Hz, 2H), 3.76 (s, 3H), 4.11 (s, 2H), 5.22 (t, J=7.6 Hz, 1H), 5.38 (s, 2H), 6.71 (s, 1H), 6.83 (d, J=16.0 Hz, 1H), 7.24 (d, J=16.0 Hz, 1H), 7.28 (t, J=7.6 Hz, 1H), 7.39 (d, J=7.6 Hz, 2H), 7.46 (t, J=7.6 Hz, 2H), 12.47 (s, 1H).

Example 201

Preparation of 2-isopentenyl-3-aminomethoxy-5-[(E)-styryl]anisole (26c)

Use compound 26a as material, and follow the method described in Example 111 to obtain a white solid as the target product (85%). $^1$H NMR (400 MHz, DMSO-$d_6$): 1.79 (s, 3H), 1.81 (s, 3H), 3.28 (d, J=7.6 Hz, 2H), 3.73 (s, 3H), 4.12 (s, 2H), 5.20 (t, J=7.6 Hz, 1H), 5.31 (s, 2H), 635 (s, 1H), 6.38 (s, 1H), 6.81 (d, J=16.0 Hz, 1H), 7.25 (d, J=16.0 Hz, 1H), 7.29 (t, J=7.6 Hz, 1H), 7.38 (d, J=7.6 Hz, 2H), 7.43 (t, J=7.6 Hz, 2H).

Example 202

Preparation of 2-(1,4-dibenzyl-piperazin-2-yl)methoxy-3-isopentenyl-4-methoxy-6-[(E)-styryl]benzoate (25b)

Use compound 8 and 1,4-dibenzyl-piperazin-2-ylmethanol as materials, and follow the method described in Example 199 to obtain a white solid as the target product (80%). $^1$H NMR (400 MHz, DMSO-$d_6$): 1.79 (s, 3H), 1.81 (s, 3H), 2.42 (m, 2H), 2.46 (m, 4H), 3.20 (d, J=7.6 Hz, 2H), 336 (m, 1H), 3.62 (s, 4H), 3.73 (s, 3H), 3.91 (s, 3H), 4.12 (dd, J1=7.6 Hz, J2=12.0 Hz, 2H), 5.20 (t, J=7.6 Hz, 1H), 6.70 (s, 1H), 6.81 (d, J=16.0 Hz, 1H), 7.10 (d, J=7.6 Hz, 4H), 7.25 (d, J=16.0 Hz, 1H), 7.34 (m, 6H), 7.45 (m, 5H).

Example 203

Preparation of methyl 2-(piperazin-2-yl)methoxy-3-isopentenyl-4-methoxy-6-[(E)-styryl]benzoate (26d)

Use compound 25b as material, and follow the method described in Example 200 to obtain a white solid as the target product (92%). $^1$H NMR (400 MHz, DMSO-$d_6$): 1.79 (s, 3H), 1.81 (s, 3H), 2.63 (m, 2H), 2.67 (m, 4H), 313 (d, J=7.6 Hz, 2H), 3.36 (m, 1H), 3.76 (s, 3H), 3.89 (s, 3H), 4.14 (dd, J1=7.6 Hz, J2=12.0 Hz, 2H), 433 (s, 2H), 51 (t, J=7.6 Hz, 1H), 638 (s,

Example 204

Preparation of 2-(piperazin-2-yl)methoxy-3-isopentenyl-4-methoxy-6-[(E)-styryl]benzoic acid (26e)

Use compound 26d as material, and follow the method described in Example 8 to obtain a white solid as the target product (90%). $^1$H NMR (400 MHz, DMSO-d$_6$): 1.78 (s, 3H), 1.82 (s, 3H), 2.61 (m, 2H), 2.65 (m, 4H), 3.22 (d, J=7.6 Hz, 2H), 3.37 (m, 1H), 3.78 (s, 3H), 4.12 (dd, J1=7.6 Hz, J2=12.0 Hz, 2H), 4.51 (s, 2H), 53 (t, J=7.6 Hz, 1H), 6.60 (s, 1H), 6.81 (d, J=16.0 Hz, 1H), 7.25 (d, J=16.0 Hz, 1H), 731 (t, J=7.6 Hz, 1H), 7.35 (d, J=7.6 Hz, 2H), 7.42 (t, J=7.6 Hz, 2H), 12.35 (s, 1H).

Example 205

Preparation of 2-isopentenyl-3-(piperazin-2-yl)methoxy-5-[(E)-styryl]anisole (26f)

Use compound 26d as material, and follow the method described in Example 113 to obtain a white solid as the target product (68%). $^1$H NMR (400 MHz, DMSO-d$_6$): 1.79 (s, 3H), 1.81 (s, 3H), 2.63 (m, 2H), 2.67 (m, 4H), 315 (d, J=7.6 Hz, 2H), 3.39 (m, 1H), 3.79 (s, 3H), 4.11 (dd, J1=7.6 Hz, J2=12.0 Hz, 2H), 4.48 (s, 2H), 5.21 (t, J=7.6 Hz, 1H), 69 (s, 1H), 6.35 (s, 1H), 6.79 (d, J=16.0 Hz, 1H), 7.24 (d, J=16.0 Hz, 1H), 7.28 (t, J=7.6 Hz, 1H), 737 (d, J=7.6 Hz, 2H), 7.41 (t, J=7.6 Hz, 2H).

Example 206

Preparation of 2-iso-ureido-3-isopentenyl-4-methoxy-6-[(E)-styryl]-benzoate (27a)

Dissolve compound 8 (1.0 g, 2.84 mmol) and aminocyanide (0.24 g, 5.68 mmol) in ethylether (20 ml), aerate in hydrogen chloride gas at 0° C. for 1h, then react at room temperature for 6h until completion, subsequently wash the reaction solution successively with water and saturated brine, desiccate the organic liquid over anhydrous magnesium sulfate, filter, and concentrate the liquid and redissolve the residue, feed the solution into a chromatographic column, evaporate the solvent in the eluent to obtain a white solid as the target product (0.88 g, 79%). $^1$H NMR (400 MHz, DMSO-d$_6$): 1.79 (s, 3H), 1.81 (s, 3H), 3.22 (d, J=7.6 Hz, 2H), 3.78 (s, 3H), 3.89 (s, 3H), 41 (s, 1H), 4.85 (s, 1H), 5.24 (t, J=7.6 Hz, 1H), 6.68 (s, 1H), 6.80 (d, J=16.0 Hz, 1H), 74 (d, J=16.0 Hz, 1H), 7.30 (t, J=7.6 Hz, 1H), 7.35 (d, J=7.6 Hz, 2H), 7.47 (t, J=7.6 Hz, 2H).

Example 207

Preparation of 2-iso-ureido-3-isopentenyl-4-methoxy-6-[(E)-styryl]benzoic acid (27b)

Use compound 1 as material, and follow the method described in Example 206 to obtain a white solid as the target product (75%). $^1$H NMR (400 MHz, DMSO-d$_6$): 1.80 (s, 3H), 1.83 (s, 3H), 3.29 (d, J=7.6 Hz, 2H), 3.73 (s, 3H), 4.18 (s, 1H), 4.80 (s, 1H), 5.23 (t, J=7.6 Hz, 1H), 6.60 (s, 1H), 6.75 (d, J=16.0 Hz, 1H), 7.18 (d, J=16.0 Hz, 1H), 79 (t, J=7.6 Hz, 1H), 7.38 (d, J=7.6 Hz, 2H), 7.45 (t, J=7.6 Hz, 2H), 12.21 (s, 1H).

Example 208

Preparation of 2-isopentenyl-3-isoureido-5-[(E)-styryl]anisole (27c)

Use compound 9 as material, and follow the method described in Example 206 to obtain a white solid as the target product (74%). $^1$H NMR (400 MHz, DMSO-d$_6$): 1.81 (s, 3H), 1.82 (s, 3H), 3.23 (d, J=7.6 Hz, 2H), 3.75 (s, 3H), 4.13 (s, 1H), 4.65 (s, 1H), 50 (t, J=7.6 Hz, 1H), 635 (s, 1H), 6.42 (s, 1H), 6.78 (d, J=16.0 Hz, 1H), 7.19 (d, J=16.0 Hz, 1H), 7.24 (t, J=7.6 Hz, 1H), 7.34 (d, J=7.6 Hz, 2H), 7.39 (t, J=7.6 Hz, 2H), 7.45 (t, J=7.6 Hz, 2H).

Example 209

Preparation of methyl 2-Hydrazinoformyloxy-3-isopentenyl-4-methoxy-6-[(E)-styryl]benzoate (29a)

Dissolve compound 8 (1.0 g, 2.84 mmol) and triethylamine (0.43 g, 4.26 mmol) in dichloromethane (30 ml), add dropwise chloroformyl chloride at 0° C. (0.40 g, 3.98 mmol), after finishing the addition, react at room temperature for 4h, cool the solution to 0° C., add dropwise hydrazine (0.2 g, 5.68 mmol) dichloromethane solution slowly at room temperature, after finishing the addition react at room temperature until finishing the reaction, subsequently wash the solution successively with water, dilute hydrochloric acid and saturated brine, dry the organic layer over anhydrous magnesium sulfate. Filter and concentrate the solution, and redissolve the residue, feed the solution into a chromatographic column, evaporate the solvent in the eluent to obtain a white solid as the target product (0.87 g, 75%). $^1$H NMR (400 MHz, DMSO-d$_6$): 1.78 (s, 3H), 1.81 (s, 3H), 3.24 (d, J=7.6 Hz, 2H), 3.78 (s, 3H), 3.87 (s, 3H), 45 (s, 2H), 6.73 (s, 1H), 6.79 (d, J=16.0 Hz, 1H), 7.24 (d, J=16.0 Hz, 1H), 7.34 (d, J=7.6 Hz, 2H), 7.39 (t, J=7.6 Hz, 2H), 7.42 (s, 1H), 7.45 (t, J=7.6 Hz, 2H).

Example 210

Preparation of 2-Hydrazinoformyloxy-3-isopentenyl-4-methoxy-6-[(E)-styryl]benzoic acid (29b)

Use compound 1 as material, and follow the method described in Example 209 to obtain a white solid as the target product (74%). $^1$H NMR (400 MHz, DMSO-d$_6$): 1.77 (s, 3H), 1.80 (s, 3H), 3.25 (d, J=7.6 Hz, 2H), 3.78 (s, 3H), 4.12 (s, 2H), 6.70 (s, 1H), 6.82 (d, J=16.0 Hz, 1H), 7.26 (d, J=16.0 Hz, 1H), 7.30 (d, J=7.6 Hz, 2H), 7.34 (t, J=7.6 Hz, 2H), 7.38 (s, 1H), 7.42 (t, J=7.6 Hz, 2H), 12.13 (s, 1H).

Example 211

Preparation of 2-isopentenyl-3-hydrazinoformylox-5-[(E)-styryl]anisole (29c)

Use compound 9 as material, and follow the method described in Example 209 to obtain a white solid as the target product (74%). $^1$H NMR (400 MHz, DMSO-d$_6$): 1.78 (s, 3H), 1.81 (s, 3H), 3.26 (d, J=7.6 Hz, 2H), 3.79 (s, 3H), 4.18 (s, 2H), 68 (s, 1H), 6.32 (s, 1H), 6.80 (d, J=16.0 Hz, 1H), 7.23 (d, J=16.0 Hz, 1H), 7.29 (d, J=7.6 Hz, 2H), 7.32 (t, J=7.6 Hz, 2H), 7.39 (s, 1H), 7.43 (t, J=7.6 Hz, 2H).

Example 212

Preparation of methyl 2-methoxycarbonylformyloxy-3-isopentenyl-4-methoxy-6-[(E)-styryl]benzoate (30a)

Use compound 8 and methyl 2-chloro-2-carbonyl acetate as materials, and follow the method described in Example 180 to obtain a white solid as the target product (78%). $^1$H NMR (400 MHz, DMSO-d$_6$): 1.79 (s, 3H), 1.82 (s, 3H), 3.27 (d, J=7.6 Hz, 2H), 3.67 (s, 3H), 3.74 (s, 3H), 3.87 (s, 3H), 5.23 (t, J=7.6 Hz, 1H), 6.70 (s, 1H), 6.82 (d, J=16.0 Hz, 1H), 7.28 (d, J=16.0 Hz, 1H), 7.31 (t, J=7.6 Hz, 2H), 7.38 (s, 1H), 7.42 (t, J=7.6 Hz, 2H).

Example 213

Preparation of methyl 2-carboxyformylxy-3-isopentenyl-4-methoxy-6-[(E)-styryl]benzoate (31a)

Dissolve compound 30a (1.0, 2.28 mmol) in THF (20 ml), add in 10% NaOH (10 ml) solution, stir the reaction solution at room temperature for 3h to complete the reaction, pour the reaction solution into ice-water, add in 10% hydrochloric acid to adjust the pH to less than 2, extract with ethyl acetate, desiccate the extract over anhydrous magnesium sulfate, filter and concentrate the solution, redissolve the residue, feed the solution into a chromatographic column, evaporate the solvent in the eluent to obtain a white solid as the target product (0.87 g, 90%). $^1$H NMR (400 MHz, DMSO-d$_6$): 1.79 (s, 3H), 1.82 (s, 3H), 3.24 (d, J=7.6 Hz, 2H), 3.74 (s, 3H), 3.88 (s, 3H), 51 (t, J=7.6 Hz, 1H), 6.73 (s, 1H), 6.81 (d, J=16.0 Hz, 1H), 7.26 (d, J=16.0 Hz, 1H), 7.30 (t, J=7.6 Hz, 2H), 7.39 (s, 1H), 7.45 (t, J=7.6 Hz, 2H), 12.56 (s, 1H).

Example 214

Preparation of 2-formyloxylformylox-3-isopentenyl-4-methoxy-6-[(E)-styryl]benzoic acid (30b)

Use compound 1 and methyl 2-chloro-2-carbonyl acetate as materials, and follow the method described in Example 180 to obtain a white solid as the target product (78%). $^1$H NMR (400 MHz, DMSO-d$_6$): 1.77 (s, 3H), 1.80 (s, 3H), 34 (d, J=7.6 Hz, 2H), 3.68 (s, 3H), 3.75 (s, 3H), 5.21 (t, J=7.6 Hz, 1H), 6.73 (s, 1H), 6.80 (d, J=16.0 Hz, 1H), 76 (d, J=16.0 Hz, 1H), 7.28 (t, J=7.6 Hz, 2H), 7.31 (s, 1H), 7.41 (t, J=7.6 Hz, 2H), 12.23 (s, 1H).

Example 215

Preparation of 2-carboxyformyloxy-3-isopentenyl-4-methoxy-6-[(E)-styryl]benzoic acid (31b)

Use compound 30b as material, and follow the method described in Example 213 to obtain a white solid as the target product (85%). $^1$H NMR (400 MHz, DMSO-d$_6$): 1.79 (s, 3H), 1.82 (s, 3H), 3.26 (d, J=7.6 Hz, 2H), 3.77 (s, 3H), 51 (t, J=7.6 Hz, 1H), 6.72 (s, 1H), 6.81 (d, J=16.0 Hz, 1H), 7.24 (d, J=16.0 Hz, 1H), 7.29 (t, J=7.6 Hz, 2H), 7.32 (s, 1H), 7.45 (t, J=7.6 Hz, 2H), 12.23 (s, 1H), 12.78 (s, 1H).

Example 216

Preparation of 2-isopentenyl-3-formyloxyl formyloxy-5-[(E)-styryl]anisole (30c)

Use compound 9 and methyl 2-chloro-2-carbonyl-acetate as materials, and follow the method described in Example 180 to obtain a white solid as the target product (79%). $^1$H NMR (400 MHz, DMSO-d$_6$): 1.78 (s, 3H), 1.82 (s, 3H), 3.27 (d, J=7.6 Hz, 2H), 3.67 (s, 3H), 3.75 (s, 3H), 5.21 (t, J=7.6 Hz, 1H), 637 (s, 1H), 6.42 (s, 1H), 6.81 (d, J=16.0 Hz, 1H), 7.23 (d, J=16.0 Hz, 1H), 7.29 (t, J=7.6 Hz, 2H), 7.35 (s, 1H), 7.45 (t, J=7.6 Hz, 2H).

Example 217

Preparation of 2-isopentenyl-3-carboxyformyloxy-5-[(E)-styryl]anisole (31c)

Use compound 30c as material, and follow the method described in Example 213 to obtain a white solid as the target product (85%). $^1$H NMR (400 MHz, DMSO-d$_6$): 1.78 (s, 3H), 1.82 (s, 3H), 3.26 (d, J=7.6 Hz, 2H), 3.78 (s, 3H), 5.23 (t, J=7.6 Hz, 1H), 6.34 (s, 1H), 6.41 (s, 1H), 6.80 (d, J=16.0 Hz, 1H), 7.25 (d, J=16.0 Hz, 1H), 7.29 (t, J=7.6 Hz, 2H), 7.37 (s, 1H), 7.44 (t, J=7.6 Hz, 2H), 12.54 (s, 1H).

Example 218

Preparation of 2-hydroxy-3-isopentenyl-4-methoxy-6-[(E)-styryl]benzamide (32)

Dissolve compound 8 (1.0 g, 2.84 mmol) in methanolic ammonia (10%, 10 ml), reflux to react for 4-6h, after completion, pour the solution into ice water, extract the solution with ethyl acetate, desiccate the organic layer over anhydrous magnesium sulfate. Filter and concentrate the solution, redissolve the residue, feed the solution into a chromatographic column, evaporate the solvent in the eluent to obtain a white solid as the target product (0.86 g, 92%). $^1$H NMR (400 MHz, DMSO-d$_6$): 1.79 (s, 3H), 1.81 (s, 3H), 3.25 (d, J=7.6 Hz, 2H), 3.77 (s, 3H), 5.20 (t, J=7.6 Hz, 1H), 6.68 (s, 1H), 6.80 (d, J=16.0 Hz, 1H), 7.24 (d, J=16.0 Hz, 1H), 79 (t, J=7.6 Hz, 2H), 7.36 (s, 1H), 7.44 (t, J=7.6 Hz, 2H), 7.90 (s, 2H).

Example 219

Preparation of 2,4-dihydroxy-3-isopentenyl-6-[(E)-styryl]benzoic acid (33)

Add cajanine 1 (0.1 g, 0.29 mmol) into hydroiodic acid (10 ml, 55%), reflux to react for 2 h, after completion of the reaction, cool the reactant, extract the solution with ethyl acetate (3×30 ml). Pool the organic layer, wash successively with water and saturated brine. Dry the solution over anhydrous magnesium sulfate, filter and rotary evaporate out the solvent, redissolve the residue in petroleum ether/ethyl acetate and recrystallize the solution to obtain a white solid as the target product (66 mg, 70%). $^1$H NMR (400 MHz, DMSO-d$_6$): 1.65 (s, 3H), 1.78 (s, 3H), 332 (d, J=7.6 Hz, 2H), 5.23 (t, J=7.6 Hz, 1H), 6.59 (s, 1H), 6.82 (d, J=16.0 Hz, 1H), 72 (d, J=16.0 Hz, 1H), 7.28 (t, J=7.6 Hz, 1H), 7.38 (t, J=7.6 Hz, 2H), 7.52 (d, J=7.6 Hz, 2H), 10.35 (s, 1H), 1132 (s, 1H), 12.30 (br, 1H).

Example 220

Preparation of the double bond hydrogenation product of Cajanine (34)

Dissolve cajanine (0.1 g, 0.29 mmol) in 15 ml anhydrous ethanol, add in 10 mg 5% PdC, hydrogenate at room temperature under 70 psi hydrogen pressure for 4h. After completion of the reaction, filter out the catalyst, evaporate the filtrate to dryness to obtain double bond reduction product of cajanine, i.e. the hydrogenated product 99 mg (98%). $^1$H NMR (400 MHz, CDCl$_3$): 0.95 (d, J=6.4 Hz, 6H), 1.36 (m, 2H), 1.58 (m, 1H), 2.63 (t, J=7.6 Hz, 2H), 2.92 (t, J=7.6 Hz, 2H), 3.26 (t, J=7.6 Hz, 2H), 3.78 (s, 3H), 6.19 (s, 1H), 7.20 (d, J=7.2 Hz, 2H), 7.30 (m, 3H), 10.5 (br, 1H), 11.63 (s, 1H).

Example 221

Preparation of methyl 2-hydroxy-4-methoxy-6-phenethyl benzoate (35)

Dissolve compound 7 (5.0 g, 0.0176 mol), in absolute ethanol (50 ml), add in PdC (0.25 g), hydrogenate at room temperature under 50 psi hydrogen pressure for 3h. After completion of the reaction, filter out the catalyst, evaporate the filtrate to dryness to obtain a white solid as the product (97%). $^1$H NMR (400 MHz, DMSO-d$_6$): 2.77 (m, 2H), 2.84 (m, 2H), 3.70 (s, 3H), 3.80 (s, 3H), 6.30 (d, J=2.4 Hz, 1H), 633 (d, J=2.4 Hz, 1H), 7.18 (m, 3H), 7.27 (t, J=7.6 Hz, 2H), 10.35 (s, 1H).

Example 222

Preparation of methyl 2-hydroxy-3-isopentenyl-4-methoxy-6-phenethyl benzoate (36)

Use compound 35 as material, and follow the method described in Example 7 to obtain a white solid as the target product (65%). $^1$H NMR (400 MHz, CDCl$_3$): 1.67 (s, 3H), 1.78 (s, 3H), 2.84 (t, J=8.0 Hz, 2H), 3.18 (t, J=8.0 Hz, 2H), 3.33 (d, J=7.2 Hz, 2H), 3.79 (s, 3H), 3.95 (s, 3H), 5.20 (t, J=7.2 Hz, 1H), 6.21 (s, 1H), 7.20 (m, 3H), 7.30 (t, J=7.2 Hz, 2H), 11.70 (s, 1H).

Example 223

Preparation of 2-hydroxy-3-isopentenyl-4-methoxy-6-phenethyl benzoic acid (37)

Use compound 36 as material, and follow the method described in Example 8 to obtain a white solid as the target product (87%). $^1$H NMR (400 MHz, DMSO-d$_6$): 1.59 (s, 3H), 1.69 (s, 3H), 2.80 (t, J=7.6 Hz, 2H), 3.12 (t, J=7.6 Hz, 2H), 3.21 (d, J=6.8 Hz, 2H), 3.78 (s, 3H), 5.10 (t, J=6.8 Hz, 1H), 6.45 (s, 1H), 7.17 (t, J=7.2 Hz, 1H), 7.22 (d, J=7.2 Hz, 2H), 7.28 (t, J=7.2 Hz, 2H), 12.47 (br, 1H), 13.95 (br, 1H).

Example 224

Preparation of methyl 2-oxo-4-hydroxy-6-methyl-cyclohexen-3-yl carboxylate (38)

Dissolve sodium metal (3.1 g, 0.134 mol) in dry methanol (200 ml), add in methyl acetoacetate (12.0 g, 0.103 mol) and methyl crotonate (12.4 g, 0.124 mol at room temperature), after finishing the addition, reflux to react for 6h to complete the reaction, then distill out most of the methanol, pour the residue into ice water (200 ml), extract with ethyl acetate (3×50 ml), adjust pH of the aqueous layer to less than 2 with dilute 15% hydrochloric acid, extract again with ethyl acetate (3×50 ml). Pool the organic layer, and wash with saturated brine, dry the solution over anhydrous MgSO$_4$. Filter and evaporate the solution to dryness, redissolve the residue, recrystallize the solution to obtain a white solid as the target product (13.2 g, 70%) with petroleum ether/ethyl acetate and recrystallized. $^1$H NMR (400 MHz, DMSO-d$_6$): 0.94 (d, J=6.0 Hz, 3H), 2.32 (m, 3H), 3.09 (d, J=9.2 Hz, 1H), 3.63 (s, 3H), 5.21 (s, 1H), 11.37 (s, 1H).

Example 225

Preparation of methyl 2,4-dihydroxy-3-bromo-6-methylbenzoate (39)

Dissolve compound 38 (10.0 g, 0.054 mol) in glacial acetic acid (150 ml), add in the solution of bromine (19.9 g, 0.124 mol) in acetic acid (40 ml) dropwise at room temperature, after finishing the addition, react for 12h to complete the reaction, then pour the solution into ice water to form large amount of white solid, filter out the precipitation, wash the filter cake with plenty of water, dry the cake. Dissolve the resulting solid with petroleum ether/ethyl acetate, feed the solution to a silica gel column, evaporate the solvent in the eluent to obtain a white solid as the relatively pure product (5.6 g, 40%). $^1$H NMR (400 MHz, DMSO-d$_6$): 2.21 (s, 3H), 3.86 (s, 3H), 6.41 (s, 1H), 10.98 (s, 1H), 11.72 (s, 1H).

Example 226

Preparation of methyl 2,4-dimethoxy-3-bromo-6-methylbenzoate (40)

Use compound 39 as material, and follow the method described in Example 2 to obtain a white solid as the target product (95%). $^1$H NMR (400 MHz, CDCl$_3$): 230 (s, 3H), 3.86 (s, 3H), 3.89 (s, 3H), 3.91 (s, 3H), 632 (s, 1H).

Example 227

Preparation of methyl 2,4-Dimethoxy-3-bromo-6-bromomethylbenzoate (41)

Use compound 40 as material, and follow the method described in Example 3 to obtain a white solid as the target product (82%). $^1$H NMR (400 MHz, CDCl$_3$): 3.90 (s, 3H), 3.94 (s, 3H), 3.96 (s, 3H), 433 (s, 2H), 6.73 (s, 1H).

Example 228

Preparation of methyl 2,4-Dimethoxy-3-bromo-6-(diethyl methylenephosphonite)benzoate (42)

Use compound 41 as material, and follow the method described in Example 4 to obtain a white solid as the target product (86%). ¹H NMR (400 MHz, CDCl₃): 3.90 (s, 3H), 3.94 (s, 3H), 3.96 (s, 3H), 433 (s, 2H), 6.73 (s, 1H).

Example 229

Preparation of methyl 2,4-dimethoxy-3-isopentenyl-6-(diethyl methylenephosphonite)benzoate (43)

Use compound 42 as material, and follow the method described in Example 162 to obtain a colorlessly liquid as the target product (78%). ¹H NMR (400 MHz, CDCl₃): 1.26 (t, J=7.2 Hz, 6H), 3.29 (d, J=22.4 Hz, 2H), 3.87 (s, 3H), 3.92 (s, 6H), 4.02 (q, J=7.2 Hz, 4H), 6.78 (s, 1H).

Example 230

Preparation of methyl 2,4-dimethoxy-3-isopentyl-6-(diethyl methylenephosphonite)benzoate (44)

Use compound 43 as material, and follow the method described in Example 220 to obtain a colorless oily liquid as the target product (92%). ¹H NMR (400 MHz, CDCl₃): 0.88 (d, J=6.4 Hz, 6H), 1.26 (t, J=7.2 Hz, 6H), 1.37 (m, 2H), 1.63 (m, 1H), 2.58 (t, J=8.0 Hz, 2H), 3.32 (d, J=21.6 Hz, 2H), 3.76 (s, 3H), 3.83 (s, 3H), 3.91 (s, 3H), 4.02 (q, J=7.2 Hz, 4H), 6.71 (s, 1H).

Example 231

Preparation of methyl 2,4-dimethoxy-3-isopentyl-6-[(E)-styryl]benzoate (45)

Use compound 44 as material, and follow the method described in Example 5 to obtain a colorless oily liquid as the target product (80%). ¹H NMR (400 MHz, CDCl₃): 0.94 (d, J=6.8 Hz, 6H), 1.39 (m, 2H), 1.62 (m, 1H), 2.62 (t, J=8.0 Hz, 2H), 3.87 (s, 3H), 3.90 (s, 3H), 3.94 (s, 3H), 6.82 (s, 1H), 7.04 (d, J=16.0 Hz, 1H), 7.28 (t, J=7.6 Hz, 1H), 7.39 (t, J=7.6 Hz, 2H), 7.55 (d, J=7.6 Hz, 2H), 7.64 (d, J=16.0 Hz, 1H).

Example 232

Preparation of methyl 2-hydroxy-4-methoxy-3-isopentyl-6-[(E)-styryl]benzoate (46)

Use compound 45 as material, and follow the method described in Example 6 to obtain a colorless oily liquid as the target product (86%). ¹H NMR (400 MHz, CDCl₃): 0.90 (d, J=6.8 Hz, 6H), 1.31 (m, 2H), 1.51 (m, 1H), 2.57 (t, J=8.0 Hz, 2H), 3.87 (s, 6H), 6.82 (s, 1H), 7.03 (d, J=16.0 Hz, 1H), 717 (t, J=7.6 Hz, 1H), 738 (t, J=7.6 Hz, 2H), 7.55 (d, J=7.6 Hz, 2H), 7.64 (d, J=16.0 Hz, 1H), 10.97 (s, 1H).

Example 233

Preparation of 2-hydroxy-4-methoxy-3-isopentyl-6-[(E)-styryl]benzoic acid (47)

Use compound 46 as material, and follow the method described in Example 8 to obtain a colorless oily liquid as the target product (90%). ¹H NMR (400 MHz, DMSO-d₆): 0.90 (d, J=6.4 Hz, 6H), 1.30 (q, J=7.2 Hz, 2H), 1.51 (m, 1H), 2.56 (t, J=7.2 Hz, 2H), 3.90 (s, 3H), 6.77 (s, 1H), 6.99 (d, J=16.0 Hz, 1H), 7.27 (t, J=7.6 Hz, 1H), 7.38 (t, J=7.6 Hz, 2H), 7.52 (d, J=7.6 Hz, 2H), 7.86 (d, J=16.0 Hz, 1H), 12.40 (br, 1H), 13.98 (br, 1H).

Example 234

Preparation of methyl 2,4-Dimethoxy-3-bromo-6-[(E)-styryl]benzoate (48)

Use compound 42 as material, and follow the method described in Example 5 to obtain a colorless oily liquid as the target product (80%). ¹H NMR (400 MHz, CDCl₃): 3.86 (s, 3H), 3.97 (s, 3H), 4.02 (s, 3H), 6.65 (s, 1H), 6.83 (d, J=16.0 Hz, 1H), 7.37 (t, J=8.0 Hz, 1H), 7.39 (t, J=8.0 Hz, 2H), 7.51 (d, J=8.0 Hz, 2H), 7.69 (d, J=16.0 Hz, 1H).

Example 235

Preparation of methyl 2-hydroxy-3-bromo-4-methoxy-6-[(E)-styryl]benzoate (49)

Use compound 48 as material, and follow the method described in Example 6 to obtain a colorless oily liquid as the target product (89%). ¹H NMR (400 MHz, CDCl₃): 3.99 (s, 3H), 4.01 (s, 3H), 6.70 (s, 1H), 6.85 (d, J=16.0 Hz, 1H), 7.38 (t, J=8.0 Hz, 1H), 7.41 (t, J=8.0 Hz, 2H), 7.52 (d, J=8.0 Hz, 2H), 7.71 (d, J=16.0 Hz, 1H), 12.28 (s, 1H)

Example 236

Preparation of methyl 2-hydroxy-3-isopentenyl-4-methoxy-6-[(E)-styryl]benzoate (8)

Use compound 49 as material, and follow the method described in Example 162 to obtain a white solid as the target product (78%). ¹H-NMR (400M, CDCl₃) δ (ppm): 1.61 (s, 3H), 1.71 (s, 3H), 3.24 (d, J=6.8 Hz, 2H), 3.91 (s, 3H), 3.94 (s, 3H), 5.12 (t, J=6.8 Hz, 1H), 6.78 (s, 1H), 7.00 (d, J=16 Hz, 1H), 7.27 (t, J=7.2 Hz, 1H), 738 (t, J=7.2 Hz, 2H), 7.52 (d, J=7.2 Hz, 2H), 7.84 (d, J=16 Hz, 1H), 11.66 (s, 1H).

Example 237

Preparation of 2-hydroxy-3-isopentenyl-4-methoxy-6-[(E)-styryl]benzoic acid (1, cajanine)

Use compound 8 as material, and follow the method described in Example 8 to obtain a white solid as the target product (92%). ¹H-NMR (400M, CDCl₃) δ (ppm): 1.61 (s, 3H), 1.71 (s, 3H), 3.24 (d, J=6.8 Hz, 2H), 3.91 (s, 3H), 5.12 (t, J=6.8 Hz, 1H), 6.78 (s, 1H), 7.00 (d, J=16 Hz, 1H), 7.27 (t, J=7.2 Hz, 1H), 7.38 (t, J=7.2 Hz, 2H), 732 (d, J=7.2 Hz, 2H), 7.84 (d, J=16 Hz, 1H), 12.28 (s, 1H) ESI-MS mz: 361.14318 [M+Na]⁺ (Calcd for C21H22O4Na: 361.14158).

Experimental Example 1

Determination of Anti-Influenza Virus Activity

Inoculate MDCK cells into 96-well culture plates and culture in the atmosphere of 5% CO₂, at 37° C. for 24 h. Add influenza virus (A/H1N1, A/H3N2 or B/13/79 type) to MDCK cells to ca. 100TCID₅₀, after virus adsorption at 37° C. for 2 h, discard the virus solution, add different dilutions of the solutions of the compounds proposed in the present invention, or the maintenance fluid of the positive control drug Ribavirin, meanwhile set a virus controls without addition of drugs and a cell control without virus infection. Culture all the samples at 37° C., when the cytopathic effect of the virus (CPE) reach 4+ in the virus control group, observe the cytopathic effect (CPE) of cells of each group at about 36 h. Calculate the 50% influenza virus inhibitory concentration ($IC_{50}$) of the samples. The results are shown in Table 1.

Experimental Example 2

Coxsackie (CoxaskiEs) Virus Activity Assay

After 24 h inoculation of VEro cells into 96 well plates, infect the cells with virus (Coxsackie virus B6) to about $100TCID_{50}$, 2 hours after absorption, discard the virus solution. Add in various concentrations of the solutions of compounds proposed in the present invention, as well as the maintenance fluid of the positive control drug Ribavirin, meanwhile, act a virus control without addition of drug and a cell control without virus infection, when the cytopathic effect of the virus (CPE) reach 4+ in the virus control group, observe the cytopathic effect (CPE) of cells of each group. Calculate the 50% influenza virus inhibitory concentration ($IC_{50}$) of the samples with REEd-MuEnch method. The results are shown in Table 1.

Experimental Example 3

Neuroprotective Activity Assay (Against Rotenone Injury and Serum Deprived Injury to PC12 Cells)

Discard the original culture media from confluent monolayers of PC12 cells (simulated neuronal cells), add DMEM complete medium with 5% FBS, 5% horse serum gently beat upon the cells with a pipette to completely disperse them, inoculate 100 μl cell suspension at a density of $5 \times 40^4$ cells/ml per well to 96 hole plates treated with poly-lysine (0.1 mg/ml) in advance, culture for 24h. Divide the experimenting cells into control group, model group and dosing groups. Add complete medium to the control group. Model groups includes rotenone group and serum-deprived group, add rotenone to the corresponding modules with a final concentration of 4 μM rotenone to take effect on the cells for 48 h, add serum-deprived groups with serum-free DMEM medium to take effect on the cells for 48 h. Dosing groups also includes two groups, one using rotenone module as model, another using serum-deprived module as model, and both add in 10 μM test compounds during modeling. 48h later, add 10 μl 5 mg/ml MTT, subsequently discard the supernatant 4h later and add in 150 μl DMSO, measure 570 nm absorbance to represent the numbers of surviving cells.

The protective effects of said compounds against rotenone injury and serum-deprived injury to PC12 cells are shown in Table 3.

Experimental Example 4

Anti-Hepatitis C Virus (HCV) Activity Assay

Inoculate Huh7.5 cells into 96-well plates to a density of $3 \times 10^4$ cells/cm², culture for 24h, infect the cells with 45 IU/cell HCV supernatant, meanwhile, add drug solutions or solvent control for treatment. After incubation for 72 h, discard the media, extract total cellular RNA with RNeasy Mini Kit, quantitatively detect HCV RNA expression levels by one-step real-time RT-PCR kit, thereby calculating the HCV inhibition rate of the drugs, and calculate half toxic concentrations $EC_{50}$ using the Reed-Muench method. Anti-HCV activities of said compounds are shown in Table 2.

Experimental Example 5

Anti-HIV (HIV) Activity Assay

Infect MT-4 cells with 100TCID50 HIV-1 III B virus at 37° C. 1.5h, after adsorption and infection, wash the cells twice with culture medium, prepare cell suspensions with concentrations of $2 \times 10^5$ cells/$mL^{-1}$, inoculate 100 μL of the suspensions into 96-well cell culture plate, add 3-fold dilutions of different concentrations of the drugs, or 4-fold dilutions of a solution of positive drug AZT into each well, duplicate each one of the samples, meanwhile seta cell control group. Incubate the samples in a humidified incubator with an atmosphere of 5% $CO_2$ at 37° C., after dose for 96 h pepet out 100 μL of the supernatants, determine P24 antigen contents with reagent kit, calculate $IC_{50}$. Anti-HIV activities of the compounds are shown in Table 2.

The invention claimed is:

1. A group of compounds having the structure shown in the general formula I:

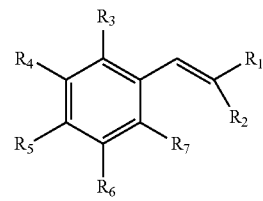

wherein $R_1$ is a substituted or unsubstituted heteroaryl, wherein said heteroaryl is pyrid-2-yl;

$R_2$ is H;

$R_3$ is selected from the group consisting of H, a carboxyl, a substituted or unsubstituted alkoxyformyl, a substituted or unsubstituted carbamoyl, and a substituted or unsubstituted formyl group;

$R_4$ is selected from the group consisting of H, hydroxy, a substituted or unsubstituted alkoxyl, a substituted or unsubstituted formyloxy, a substituted or unsubstituted amino, a halogen, and isoureido group;

$R_5$ is iso-pentenyl;

$R_6$ is selected from the group consisting of H, hydroxy, a substituted or unsubstituted alkoxy, a substituted or unsubstituted amino, a halogen, a mercapto, and an alkylthio group;

$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group.

2. The group of compounds according to claim 1 wherein the compound is one of the following:
methyl 2-hydroxyl-3-isopent-2-enyl-4-methoxy-6-[(E)-2-(pyrid-2-yl)vinyl]benzoate;
2-hydroxyl-3-isopent-2-enyl-4-methoxy-6-[(E)-2-(pyrid-2-yl)vinyl]benzoic acid;
methyl 2-hydroxyl-3-isopent-2-enyl-4-methoxy-6-[(E)-2-(4-methoxypyrid-2-yl)vinyl]benzoate;
2-hydroxyl-3-isopent-2-enyl-4-methoxy-6-[(E)-2-(4-methoxypyrid-2-yl)vinyl]benzoic acid;
2-hydroxyl-3-isopent-2-enyl-4-methoxy-6-[(E)-2-(4-hydroxypyrid-2-yl)vinyl]benzoic acid;

methyl 2-hydroxyl-3-isopent-2-enyl-4-methoxy-6-[(E)-2-(3-methoxypyrid-2-yl)vinyl]benzoate;
2-hydroxyl-3-isopent-2-enyl-4-methoxy-6-[(E)-2-(3-methoxypyrid-2-yl)vinyl]benzoic acid;
2-hydroxyl-3-isopent-2-enyl-4-methoxy-6-[(E)-2-(3-hydroxylpyrid-2-yl)vinyl]benzoic acid;
methyl 2-hydroxyl-3-isopent-2-enyl-4-methoxy-6-[(E)-2-(4,6-dimethoxypyrid-2-yl)vinyl]benzoate;
2-hydroxyl-3-isopent-2-enyl-4-methoxy-6-[(E)-2-(4,6-dimethoxypyrid-2-yl)vinyl]benzoic acid;
2-hydroxyl-3-isopent-2-enyl-4-methoxy-6-[(E)-2-(4,6-dihydroxypyrid-2-yl)vinyl]benzoic acid;
methyl 2-hydroxyl-3-isopent-2-enyl-4-methoxy-6-[(E)-2-(6-methoxypyrid-2-yl)vinyl]benzoate;
2-hydroxyl-3-isopent-2-enyl-4-methoxy-6-[(E)-2-(6-methoxypyrid-2-yl)vinyl]benzoic acid;
2-hydroxyl-3-isopent-2-enyl-4-methoxy-6-[(E)-2-(6-hydroxypyrid-2-yl)vinyl]benzoic acid;
2-isopent-2-enyl-3-methoxy-5-[(E)-2-(pyrid-2-yl)vinyl]phenol;
2-isopent-2-enyl-3-methoxy-5-[(E)-2-(4-methoxypyrid-2-yl)vinyl]phenol;
2-isopent-2-enyl-3-methoxy-5-[(E)-2-(4-hydroxypyrid-2-yl)vinyl]phenol;
2-isopent-2-enyl-3-methoxy-5-[(E)-2-(3-methoxypyrid-2-yl)vinyl]phenol;
2-isopent-2-enyl-3-methoxy-5-[(E)-2-(3-hydroxypyrid-2-yl)vinyl]phenol;
2-isopent-2-enyl-3-methoxy-5-[(E)-2-(2,4-dimethoxypyrid-6-yl)vinyl]phenol;
2-isopent-2-enyl-3-methoxy-5-[(E)-2-(2,4-dihydroxypyrid-6-yl)vinyl]phenol;
2-isopent-2-enyl-3-methoxy-5-[(E)-2-(2-methoxypyrid-6-yl)vinyl]phenol;
2 isopent-2-enyl-3-methoxy-5-[(E)-2-(2-hydroxypyrid-6-yl)vinyl]phenol.

3. A method to prepare the compounds having the structure shown by the general formula I:

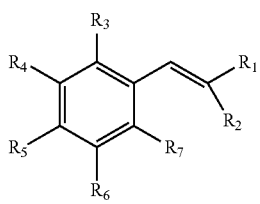

wherein $R_1$ is a substituted or unsubstituted heteroaryl, wherein said heteroaryl is pyrid-2-yl;
$R_2$ is H;
$R_3$ is carboxyl group;
$R_4$ is hydroxyl;
$R_5$ is iso-pentenyl;
$R_6$ is an alkoxy group;
$R_7$ is H,
the method according to Scheme 1:

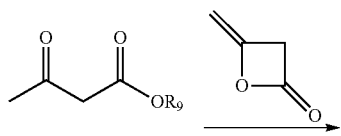

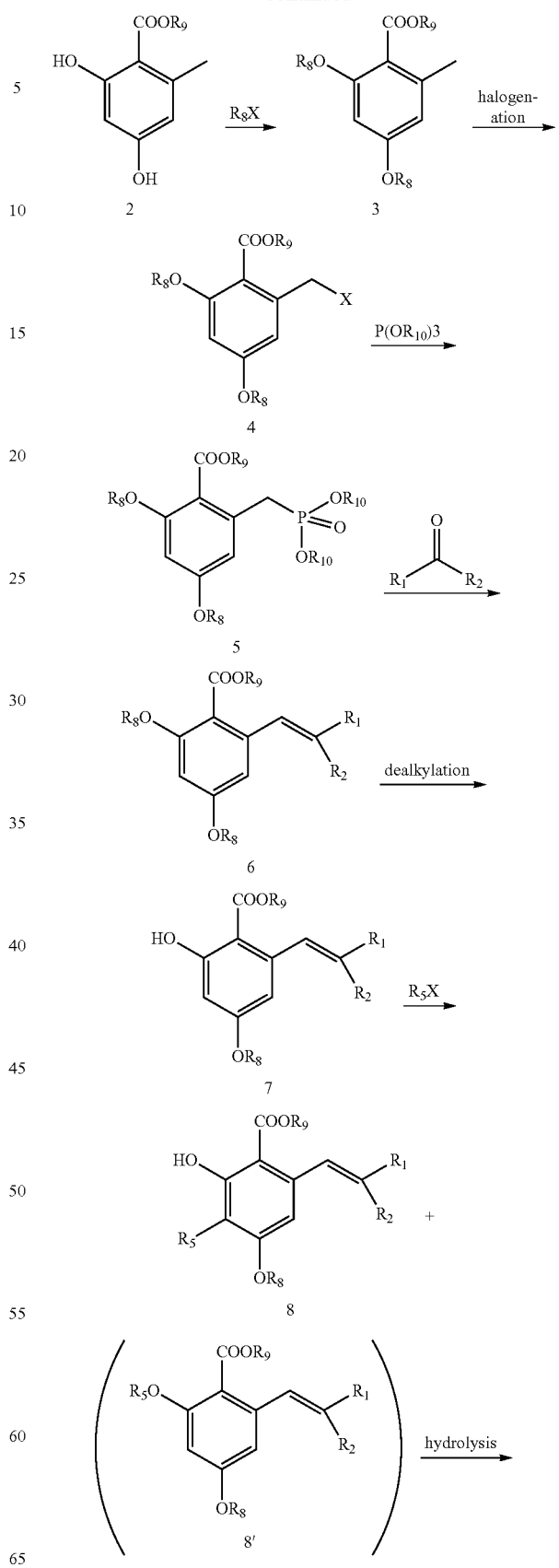

-continued

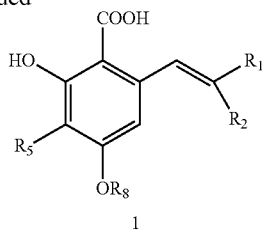
1 the method comprising:
  reacting acetoacetic ester and diethyl ketone under basic conditions to produce Compound 2;
  alkylating Compound 2 under basic conditions in a polar solvent to produce Compound 3;
  forming Compound 4 via free radical halogenation of Compound 3 in a nonpolar solvent;
  reacting Compound 4 with a phosphite triester to produce Compound 5;
  reacting Compound 5 with a ketone or aldehyde to produce Compound 6;
  dealkylating Compound 6 in the presence of a dealkylating reagent to produce Compound 7;
  reacting Compound 7 with a halogenated hydrocarbon to produce Compound 8 and an oxyalkylated Compound 8';
  hydrolyzing Compound 8 to thereby produce the compounds having the general formula I, wherein in Scheme 1, $R_8$, $R_9$, $R_{10}$ are a substituted or unsubstituted hydrocarbon alkyl with 1-18 carbons.

4. A method to prepare the compounds having the structure shown by the general formula I:

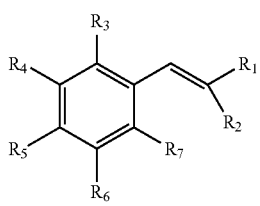

wherein $R_1$ is a substituted or unsubstituted heteroaryl, wherein said heteroaryl is pyrid-2-yl;
$R_2$ is H;
$R_3$ is selected from the group consisting of alkoxyformyl, alkylthioformyl, and a substituted carbamoyl group;
$R_4$ is selected from the group consisting of H, hydroxy, a substituted or unsubstituted alkoxyl, a substituted or unsubstituted formyloxy, a substituted or unsubstituted amino, a halogen, and isoureido group;
$R_5$ is iso-pentenyl;
$R_6$ is selected from the group consisting of H, hydroxy, a substituted or unsubstituted alkoxy, a substituted or unsubstituted amino, a halogen, a mercapto, and an alkylthio group;
$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;

the method according to Scheme 2:

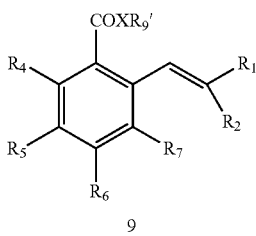

the method comprising:
  reacting a general formula I compound (i) in the presence of a condensation reagent, with $R_9$XH compounds to produce Compound 9; or (ii) with an acrylating agent to produce an acyl chloride, which in the presence of an acid binding agent condensates with $R_9$XH compounds to produce Compound 9, wherein X is selected from O, S, and N, wherein in Scheme 2, $R_9$ is a unsubstituted alkyl containing 1-18 carbons, a substituted or unsubstituted aryl or heteroaryl.

5. A method to prepare the compounds having the structure shown by the general formula I:

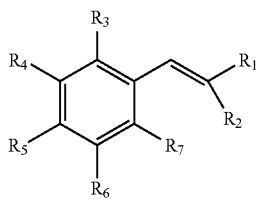

wherein $R_1$ is a substituted or unsubstituted heteroaryl, wherein said heteroaryl is pyrid-2-yl;
$R_2$ is H;
$R_3$ is carboxyl;
$R_4$ is hydroxyl;
$R_5$ is iso-pentenyl;

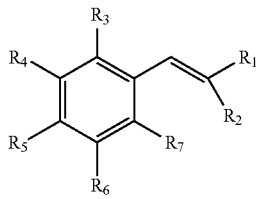

wherein $R_1$ is a substituted or unsubstituted heteroaryl, wherein said heteroaryl is pyrid-2-yl;
$R_2$ is H;

$R_3$ is selected from the group consisting of H, a carboxyl, a substituted or unsubstituted alkoxyformyl, a substituted or unsubstituted carbamoyl, and a substituted or unsubstituted formyl group;

$R_4$ is selected from the group consisting of H, hydroxy, a substituted or unsubstituted alkoxyl, a substituted or unsubstituted formyloxy, a substituted or unsubstituted amino, a halogen, and isoureido group;

$R_5$ is iso-pentenyl;

$R_6$ is an alkoxy group;

$R_7$ is a halogen;

the method according to Scheme 4:

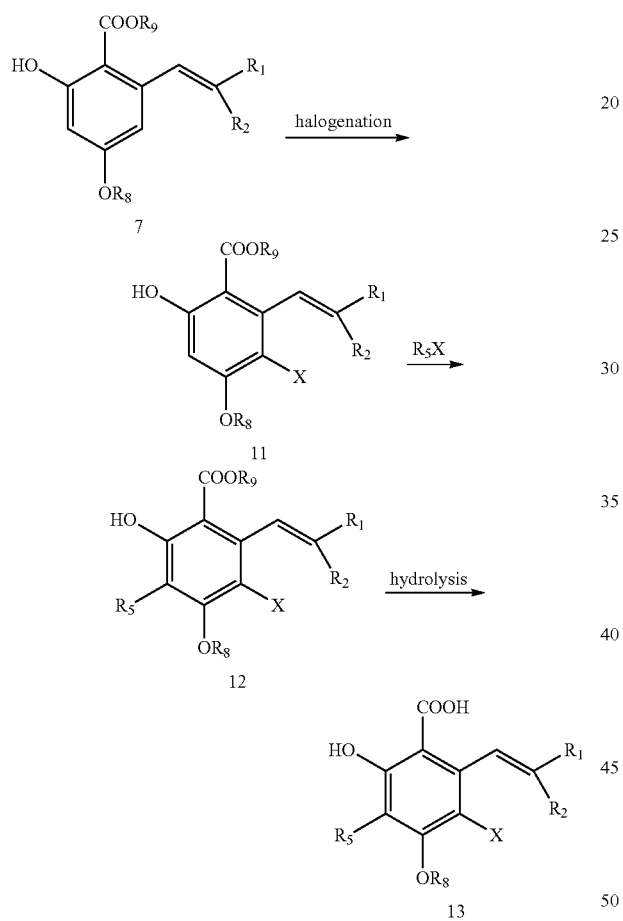

the method comprising:
  reacting Compound 7 in an organic solvent with a halogenating reagent to produce Compound 11;
  coupling Compound 11 under basic conditions with an alkylating agent to produce Compound 12;
  hydrolyzing Compound 12 under alkaline or acidic conditions to produce Compound 13, wherein in Scheme 4 X is F or Cl or Br, and $R_8$ and $R_9$ may be identical or different, and $R_8$ and $R_9$ are each selected from the group consisting of H, and an alkyl containing 1-18 carbons.

6. A method to prepare the compounds having the structure shown by the general formula I:

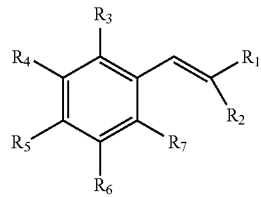

wherein $R_1$ is a substituted or unsubstituted heteroaryl, wherein said heteroaryl is pyrid-2-yl;

$R_2$ is H;

$R_3$ is carboxyl group;

$R_4$ is alkoxy group;

$R_5$ is iso-pentenyl;

$R_6$ is alkoxy group;

$R_7$ is H;

the method according to Scheme 5:

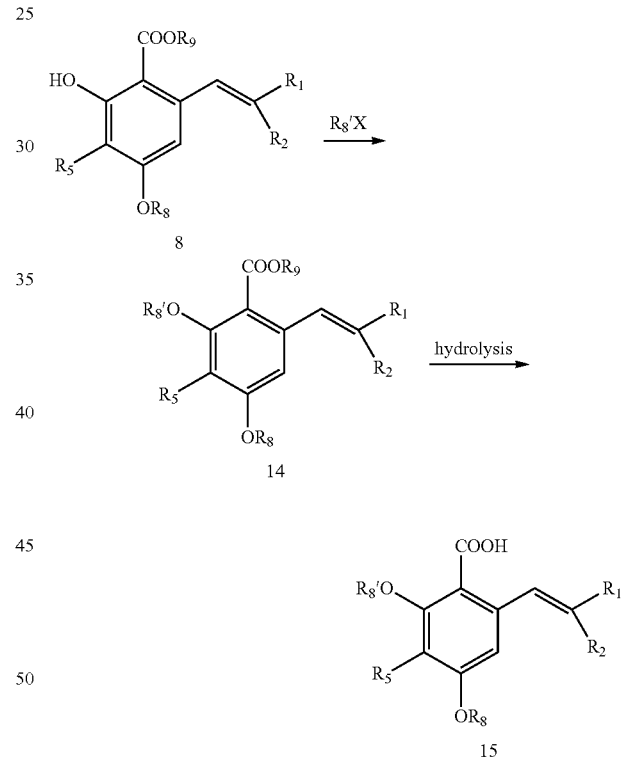

the method comprising:
  reacting Compound 8 under basic conditions with an alkylating agent to produce Compound 14;
  hydrolyzing Compound 14 under basic or acidic conditions to produce Compound 15, wherein in Scheme 5 $R_8$ and $R_8'$ may be identical or difference, and $R_8$ and $R_8'$ are each an alkyl group with 1-18 carbons, and $R_9$ is H or an alkyl group with 1-18 carbons.

7. A method to prepare the compounds having the structure shown by the general formula I:

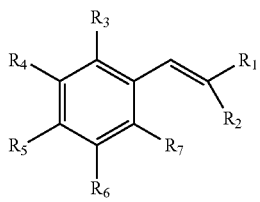

I wherein $R_1$ is a substituted or unsubstituted heteroaryl, wherein said heteroaryl is pyrid-2-yl;

$R_2$ is H;

$R_3$ is (1H-imidazol-1-yl)formyl group;

$R_4$ is selected from the group consisting of H, hydroxy, a substituted or unsubstituted alkoxyl, a substituted or unsubstituted formyloxy, a substituted or unsubstituted amino, a halogen, and isoureido group;

$R_5$ is iso-pentenyl;

$R_6$ is selected from the group consisting of H, hydroxy, a substituted or unsubstituted alkoxy, a substituted or unsubstituted amino, a halogen, a mercapto, and an alkylthio group;

$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;

the method according to Scheme 9;

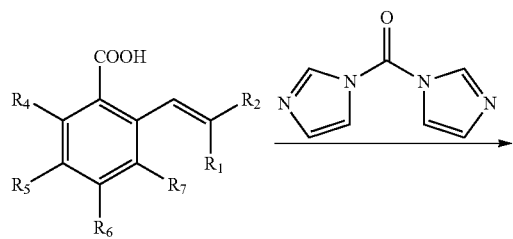

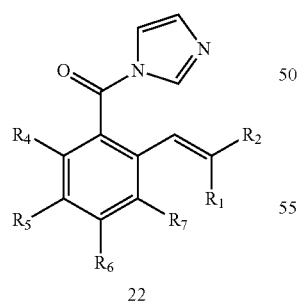

22 the method comprising:
reacting 1-carboxy substituted derivatives with carbonyl diimidazole to produce Compound 22.

8. A method to prepare the compounds having the structure shown by the general formula I:

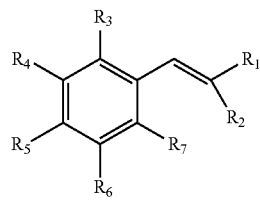

I wherein $R_1$ is a substituted or unsubstituted heteroaryl, wherein said heteroaryl is pyrid-2-yl;

$R_2$ is H;

$R_3$ is N-(carbamoyl)carbamoyl or N-(methylamidino)carbamoyl;

$R_4$ is selected from the group consisting of H, hydroxy, a substituted or unsubstituted alkoxyl, a substituted or unsubstituted formyloxy, a substituted or unsubstituted amino, a halogen, and isoureido group;

$R_5$ is iso-pentenyl;

$R_6$ is selected from the group consisting of H, hydroxy, a substituted or unsubstituted alkoxy, a substituted or unsubstituted amino, a halogen, a mercapto, and an alkylthio group;

$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;

the method according to Scheme 10:

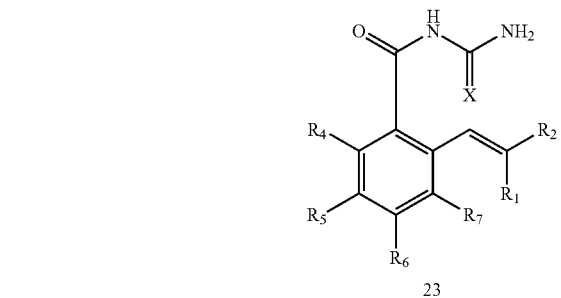

23 the method comprising:
reacting 1-carboalkoxy substituted derivatives with urea or guanidine to produce Compound 23, wherein X is O or NH.

9. A method to prepare the compounds having the structure shown by the general formula I:

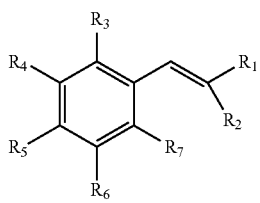

wherein $R_1$ is a substituted or unsubstituted heteroaryl, wherein said heteroaryl is pyrid-2-yl;

$R_2$ is H;

$R_3$ is selected from the group consisting of H, a carboxyl, a substituted or unsubstituted alkoxyformyl, a substituted or unsubstituted carbamoyl, and a substituted or unsubstituted formyl group;

$R_4$ is substituted formyloxy;

$R_5$ is iso-pentenyl;

$R_6$ is selected from the group consisting of H, hydroxy, a substituted or unsubstituted alkoxy, a substituted or unsubstituted amino, a halogen, a mercapto, and an alkylthio group;

$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;

the method according to Scheme 11:

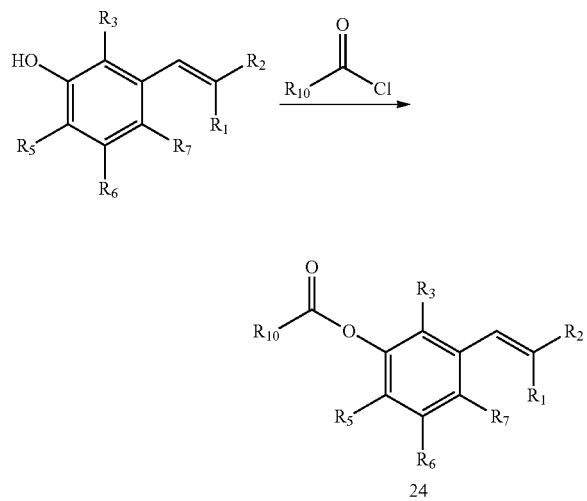

the method comprising:

reacting under basic conditions 2-hydroxyl substituted derivatives with acyl chloride to produce Compound 24, wherein $R_{10}$ is selected from the group consisting of a substituted or unsubstituted alkyl, a substituted or unsubstituted heteroaryl ring, and a substituted or unsubstituted amino group.

10. A method to prepare the compounds having the structure shown by the general formula I:

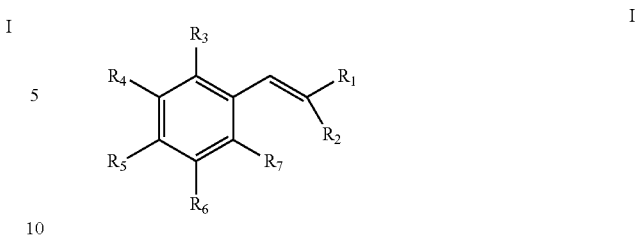

wherein $R_1$ is a substituted or unsubstituted heteroaryl, wherein said heteroaryl is pyrid-2-yl;

$R_2$ is H;

$R_3$ is selected from the group consisting H, a carboxyl group, a substituted or unsubstituted alkoxyformyl, a substituted or unsubstituted carbamoyl, and a substituted or unsubstituted formyl group;

$R_4$ is aminomethoxy group or (piperazin-2-yl)methoxy group;

$R_5$ is iso-pentenyl;

$R_6$ is selected from the group consisting of H, hydroxy, a substituted or unsubstituted alkoxy, a substituted or unsubstituted amino, a halogen, a mercapto, and an alkylthio group;

$R_7$ is selected from the group consisting of H, isopentenyl, isopentyl, 3',7'-dimethyl octadien-2',6'-yl, a substituted or unsubstituted aryl, an allyl, a halogen, and a substituted or unsubstituted amino group;

the method according to Scheme 12;

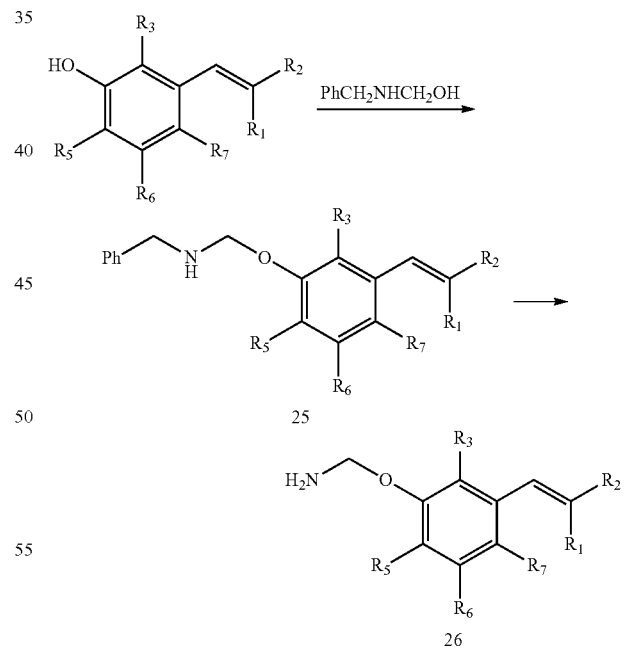

the method comprising:

reacting 2-hydroxyl substituted derivatives with N-benzyl aminomethanol to produce Compound 25;

debenzylating Compound 25 to produce Compound 26.

11. A method to prepare the compounds having the structure shown by the general formula I:

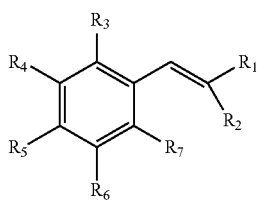

wherein $R_1$ is a substituted or unsubstituted heteroaryl, wherein said heteroaryl is pyrid-2-yl;
$R_2$ is H;
$R_3$ is selected from the group consisting of H, a carboxyl, a substituted or unsubstituted alkoxyformyl, a substituted or unsubstituted carbamoyl, and a substituted or unsubstituted formyl group;
$R_4$ is isoureido group;
$R_5$ is iso-pentenyl;
$R_6$ is selected from the group consisting of H, hydroxy, a substituted or unsubstituted alkoxy, a substituted or unsubstituted amino, a halogen, a mercapto, and an alkylthio group;
$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;
the method according to Scheme 13:

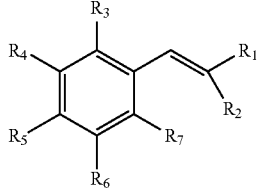

the method comprising:
reacting 2-hydroxyl substituted derivatives with aminocyanide to produce Compound 27.

12. A method to prepare the compounds having the structure shown by the general formula I:

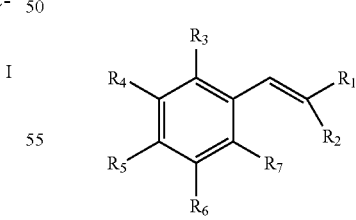

wherein $R_1$ is a substituted or unsubstituted heteroaryl, wherein said heteroaryl is pyrid-2-yl;
$R_2$ is H;
$R_3$ is selected from the group consisting of H, a carboxyl, a substituted or unsubstituted alkoxyformyl, a substituted or unsubstituted carbamoyl, and a substituted or unsubstituted formyl group;
$R_4$ is hydrazinoformyloxyl;
$R_5$ is iso-pentenyl;
$R_6$ is selected from the group consisting of H, hydroxy, a substituted or unsubstituted alkoxy, a substituted or unsubstituted amino, a halogen, a mercapto, and an alkylthio group;
$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;
the method according to Scheme 14:

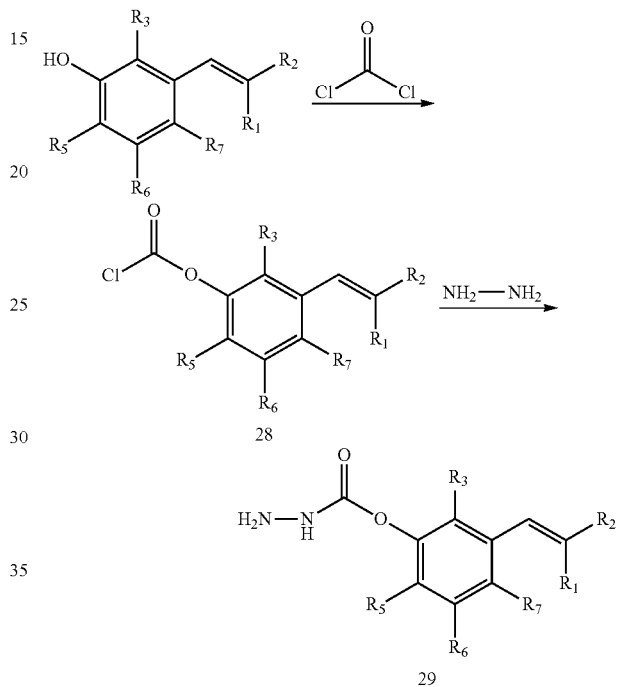

the method comprising:
reacting 2-hydroxyl substituted derivatives with carbonyl chloride to produce Compound 28;
reacting Compound 28 with hydrazine to produce Compound 29.

13. A method to prepare the compounds having the structure shown by the general formula I:

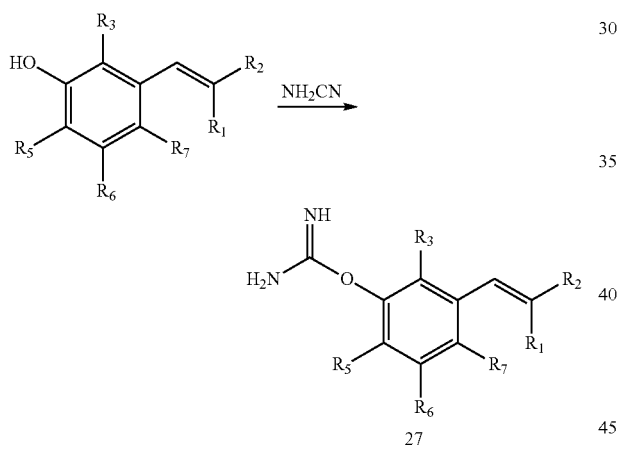

wherein $R_1$ is a substituted or unsubstituted heteroaryl, wherein said heteroaryl is pyrid-2-yl;
$R_2$ is H;
$R_3$ is selected from the group consisting of H, a carboxyl, a substituted or unsubstituted alkoxyformyl, a substituted or unsubstituted carbamoyl, and a substituted or unsubstituted formyl group;
$R_4$ is carboxyl formyloxyl;

$R_5$ is iso-pentenyl;
$R_6$ is selected from the group consisting of H, hydroxy, a substituted or unsubstituted alkoxy, a substituted or unsubstituted amino, a halogen, a mercapto, and an alkylthio group;
$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;
the method according to Scheme 15:

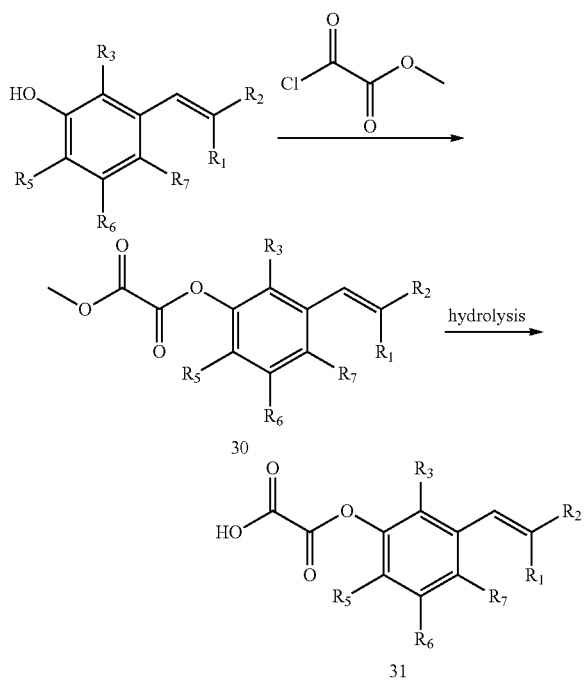

30

31 the method comprising:
reacting 2-hydroxyl substituted derivatives under basic conditions with 2-chloro-2-carbonylacetate methyl ester to produce Compound 30;
hydrolyzing Compound 30 to produce Compound 31.

14. A method to prepare the compounds having the structure shown by the general formula I:

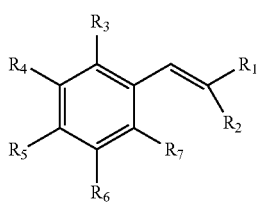

I wherein $R_1$ is a substituted or unsubstituted heteroaryl, wherein said heteroaryl is pyrid-2-yl;
$R_2$ is H;
$R_3$ is carbamoyl;
$R_4$ is selected from the group consisting of H, hydroxy, a substituted or unsubstituted alkoxyl, a substituted or unsubstituted formyloxy, a substituted or unsubstituted amino, a halogen, and isoureido group;
$R_5$ is iso-pentenyl;
$R_6$ is selected from the group consisting of H, hydroxy, a substituted or unsubstituted alkoxy, a substituted or unsubstituted amino, a halogen, a mercapto, and an alkylthio group;
$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;
the method according to Scheme 16:

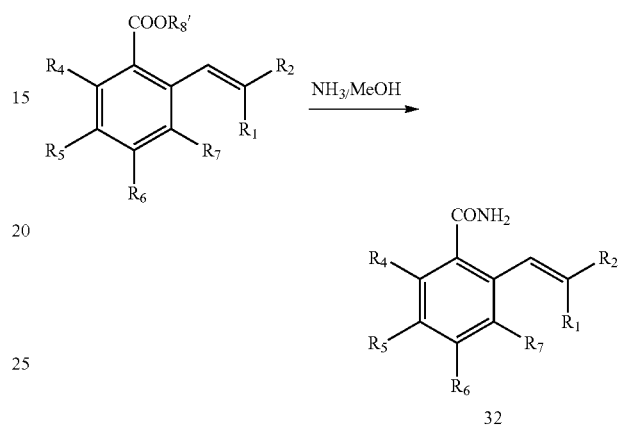

32 the method comprising:
reacting alkyloxyformyl substituted benzene derivatives via aminolysis to produce Compound 32, wherein in Scheme 16 $R_8'$ is an alkyl group with 1-18 carbons.

15. A method of treating a subject suffering from at least one of a bacterial or viral infection, and a metabolic disease, the method comprising:
administering to the subject a therapeutically effective amount of a compound or a pharmaceutically acceptable salt thereof, the compound having the structure shown in the general formula I:

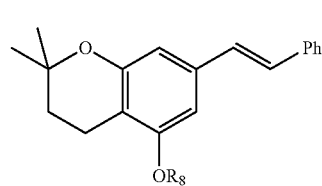

II wherein $R_1$ is a substituted or unsubstituted heteroaryl, wherein said heteroaryl is pyrid-2-yl;
$R_2$ is H;
$R_3$ is selected from the group consisting of H, a carboxyl, a substituted or unsubstituted alkoxyformyl, a substituted or unsubstituted carbamoyl, and a substituted or unsubstituted formyl group;
$R_4$ is selected from the group consisting of H, hydroxy, a substituted or unsubstituted alkoxyl, a substituted or unsubstituted formyloxy, a substituted or unsubstituted amino, a halogen, and isoureido group;
$R_5$ is iso-pentenyl;
$R_6$ is selected from the group consisting of H, hydroxy, a substituted or unsubstituted alkoxy, a substituted or unsubstituted amino, a halogen, a mercapto, and an alkylthio group;

$R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group.

16. The method of claim 15 wherein the metabolic disease is selected from the group consisting of osteoporosis, hyperlipidemia, and hyperglycemia.

17. A pharmaceutical composition for a bacterial or viral infection, neuroprotection, or a metabolic disease, the composition comprising:
   a therapeutically effective amount of a compound or a pharmaceutically acceptable salt thereof, the compound having the structure shown in the general formula I:
   $R_6$ is selected from the group consisting of H, hydroxy, a substituted or unsubstituted alkoxy, a substituted or unsubstituted amino, a halogen, a mercapto, and an alkylthio group;
   $R_7$ is selected from the group consisting of H, isopentenyl, isopentyl, 3',7'-dimethyl octadien-2',6'-yl, a substituted or unsubstituted aryl, an allyl, a halogen, and a substituted or an unsubstituted amino group;
   one or more pharmaceutically acceptable pharmaceutical adjuvants.

18. The composition of claim 17 wherein the weight proportion of the compound or salt thereof is within a range of 0.1% to 99.5%.

19. The composition of claim 18 wherein the weight proportion of the compound or salt is within a range of 0.5% to 99.5%.

* * * * *